(12) United States Patent
Stahly et al.

(10) Patent No.: US 9,968,627 B2
(45) Date of Patent: May 15, 2018

(54) SOLID FORMS COMPRISING 4-AMINO-1-β-D-RIBOFURANOSYL-1,3,5-TRIAZIN-2(1H)-ONE AND A COFORMER, COMPOSITIONS AND METHODS OF USE THEREOF

(71) Applicant: Celgene Corporation, Summit, NJ (US)

(72) Inventors: G. Patrick Stahly, West Lafayette, IN (US); David Jonaitis, Brookston, IN (US); Ho-Wah Hui, Basking Ridge, NJ (US); Kevin J. Klopfer, Flemington, NJ (US)

(73) Assignee: Celgene Corporation, Summit, NJ (US)

( * ) Notice: Subject to any disclaimer, the term of this patent is extended or adjusted under 35 U.S.C. 154(b) by 68 days.

(21) Appl. No.: 14/778,553

(22) PCT Filed: Mar. 25, 2014

(86) PCT No.: PCT/US2014/031705
§ 371 (c)(1),
(2) Date: Sep. 18, 2015

(87) PCT Pub. No.: WO2014/160698
PCT Pub. Date: Oct. 2, 2014

(65) Prior Publication Data
US 2016/0296546 A1  Oct. 13, 2016

Related U.S. Application Data

(60) Provisional application No. 61/805,459, filed on Mar. 26, 2013.

(51) Int. Cl.
*A01N 43/04* (2006.01)
*A61K 31/70* (2006.01)
*A61K 31/706* (2006.01)
*C07H 19/12* (2006.01)
*A61K 9/14* (2006.01)
*A61K 31/7052* (2006.01)
*A61K 31/7064* (2006.01)

(52) U.S. Cl.
CPC ............ *A61K 31/706* (2013.01); *A61K 9/145* (2013.01); *C07H 19/12* (2013.01); *A61K 31/7052* (2013.01); *A61K 31/7064* (2013.01)

(58) Field of Classification Search
None
See application file for complete search history.

(56) References Cited

U.S. PATENT DOCUMENTS

2006/0063735 A1* 3/2006 Redkar ................ C07H 19/12
514/49

FOREIGN PATENT DOCUMENTS

| WO | 2004/082619 A2 | 9/2004 |
| WO | 2008/088779 A2 | 7/2008 |
| WO | 2012/135405 A1 | 10/2012 |

OTHER PUBLICATIONS

Piskala et al., "Synthesis of N4-alkyl-5-azacytidines and their base-pairing with carbamoylguanidines—a contribution to explanation of the mutagenicity of 2'-deoxy-5-azacytidine," Collect. Czech. Chem. Commun., 68:711-743 (2003).
Stahly, "A survey of cycrystals reported prior to 2000," Crystal Growth & Design, 9:4212-4229 (2009).
Steed, "The role of co-crystals in pharmaceutical design," Trends in Pharmacol. Sci., 34(3):185-193 (2013).

* cited by examiner

*Primary Examiner* — Patrick T Lewis
(74) *Attorney, Agent, or Firm* — Jones Day

(57) ABSTRACT

Provided herein are solid forms comprising (a) 4-amino-1-β-D-ribofuranosyl-1,3,5-triazin-2(1H)-one and (b) a coformer. Pharmaceutical compositions comprising the solid forms (e.g., cocrystals) and methods for treating, preventing and managing various disorders are also disclosed.

21 Claims, 27 Drawing Sheets

Figure 1:
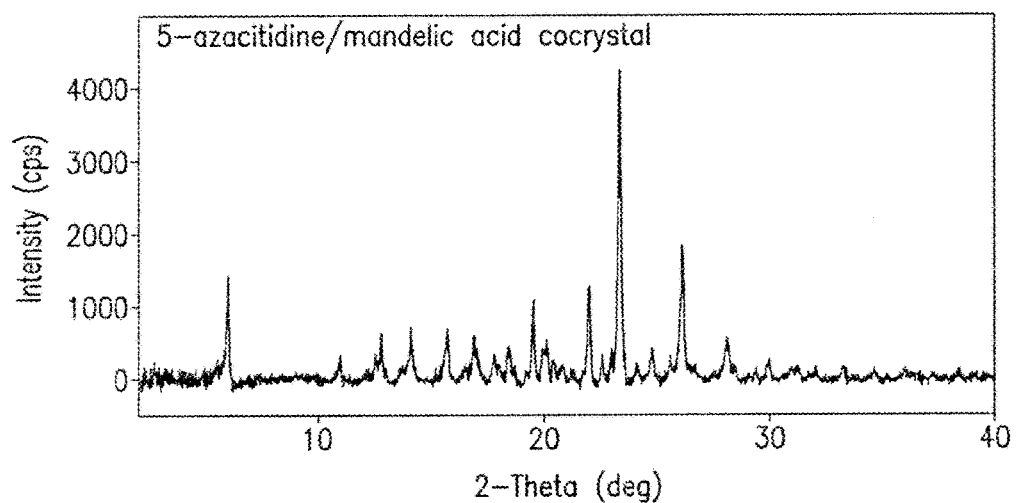

SOLID FORMS COMPRISING 4-AMINO-1-β-D-RIBOFURANOSYL-1,3,5-TRIAZIN-2(1H)-ONE AND A COFORMER, COMPOSITIONS AND METHODS OF USE THEREOF

The present application is a 371 of International Application No. PCT/US2014/031705, filed Mar. 25, 2014, which claims priority to U.S. Provisional Patent Application No. 61/805,459, filed Mar. 26, 2013, the entirety of each of which is incorporated herein by reference.

1. FIELD

This invention relates to solid forms comprising 5-azacytidine (also known as azacitidine, AZA, or 4-amino-1-β-D-ribofuranosyl-1,3,5-triazin-2(1H)-one and a coformer. Pharmaceutical compositions comprising such solid forms (e.g., cocrystals) and methods of use for treating, preventing, and managing various disorders are also provided herein.

2. BACKGROUND

2.1 Solid Forms of Pharmaceutical Compounds

The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, for example, an enhanced dissolution profile, while crystalline solids may be desirable for properties such as physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette). The importance of discovering polymorphs was underscored by the case of Ritonavir™, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species may be termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Moreover, multiple-component crystal forms may potentially be susceptible to polymorphism, wherein a given multiple-component composition may exist in more than one three-dimensional crystalline arrangement.

Cocrystals are crystalline molecular complexes of two or more non-volatile compounds bound together in a crystal lattice by non-ionic interactions. Pharmaceutical cocrystals are cocrystals of a therapeutic compound, e.g., an active pharmaceutical ingredient (API), and one or more non-volatile compound(s) (referred to herein as coformer). A coformer in a pharmaceutical cocrystal is typically selected from non-toxic pharmaceutically acceptable molecules, such as, for example, food additives, preservatives, pharmaceutical excipients, or other APIs. In recent years, pharmaceutical cocrystals have emerged as a possible alternative approach to enhance physicochemical properties of drug products.

The variety of possible solid forms creates potential diversity in physical and chemical properties for a given pharmaceutical compound. The discovery and selection of solid forms are of great importance in the development of an effective, stable and marketable pharmaceutical product.

2.2 5-Azacytidine

5-Azacytidine (National Service Center designation NSC-102816; CAS Registry Number 320-67-2), also known as azacitidine, AZA, or 4-amino-1-β-D-ribofuranosyl-1,3,5-triazin-2(1H)-one, is currently marketed as the drug product VIDAZA®. 5-Azacytidine is a nucleoside analog, more specifically a cytidine analog. 5-Azacytidine is a nucleoside metabolic inhibitor. A structural difference between 5-azacytidine and its related natural nucleoside is the presence of a nitrogen at position 5 of the cytosine ring in place of a carbon. 5-Azacytidine may be defined as having a molecular formula $C_8H_{12}N_4O_5$, a molecular weight of 244.21 grams per mole, and the following structure:

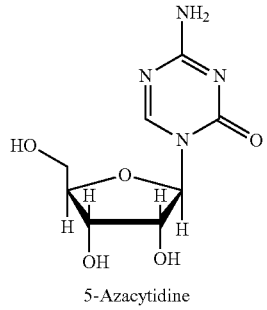

5-Azacytidine

Other members of the class of cytidine analogs include, for example: 5-aza-2'-deoxycytidine (Decitabine or 5-aza-CdR); 1-β-D-arabinofuranosylcytosine (Cytarabine or ara-C); pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxycarbonyl-5'-deoxy-5-fluorocytidine (Capecitabine); $N^4$-octadecyl-cytarabine; and elaidic acid cytarabine.

After incorporation into replicating DNA, 5-azacytidine and 5-aza-2'-deoxycytidine (decitabine) form covalent complexes with DNA methyltransferases. DNA methyltransferases are responsible for de novo DNA methylation and for reproducing established methylation patterns in daughter DNA strands of replicating DNA. Inhibition of DNA methyltransferases by 5-azacytidine or 5-aza-2'-deoxycytidine leads to DNA hypomethylation, thereby restoring normal functions to morphologically dysplastic, immature hematopoietic cells and cancer cells by re-expression of genes involved in normal cell cycle regulation, differentiation and death. The cytotoxic effects of these cytidine analogs cause the death of rapidly dividing cells, including cancer cells, that are no longer responsive to normal cell growth control mechanisms. 5-Azacytidine, unlike 5-aza-2'-deoxycytidine, also incorporates into RNA. The cytotoxic effects of 5-azacytidine may result from multiple mechanisms, including inhibition of DNA, RNA, and protein synthesis, incorporation into RNA and DNA, and activation of DNA damage pathways.

5-Azacytidine and 5-aza-2'-deoxycytidine have been tested in clinical trials and showed significant anti-tumor activity, such as, for example, in the treatment of MDS, AML, chronic myelogenous leukemia (CML), acute lymphocytic leukemia (ALL), and non Hodgkin's lymphoma (NHL). See, e.g., Aparicio et al., *Curr. Opin. Invest. Drugs* 3(4): 627-33 (2002). 5-Azacytidine has undergone NCI-sponsored clinical trials for the treatment of myelodysplastic syndromes (MDS) and has been approved for treating all FAB subtypes of MDS, several of which include: refractory anemia (RA) or refractory anemia with ringed sideroblasts (RARS) (if accompanied by neutropenia or thrombocytopenia or requiring transfusions), refractory anemia with excess blasts (RAEB), refractory anemia with excess blasts in transformation (RAEB-T), and chronic myelomonocytic leukemia (CMMoL). See, e.g., Kornblith et al., *J. Clin. Oncol.* 20(10): 2441-52 (2002); Silverman et al., *J. Clin. Oncol.* 20(10): 2429-40 (2002). 5-Azacytidine may alter the natural course of MDS by diminishing the transformation to AML through its cytotoxic activity and its inhibition of DNA methyltransferase. In a Phase III study, 5-azacytidine administered subcutaneously significantly prolonged survival and time to AML transformation or death in subjects with higher-risk MDS. See, e.g., P. Fenaux et al., *Lancet Oncol.*, 2009, 10(3):223-32. In the EU, VIDAZA® is approved for treatment of higher-risk MDS, chronic myelomonocytic leukemia (CMML, 10-29% marrow blasts without myeloproliferative disorder), and WHO-defined acute myeloid leukemia with 20% to 30% blasts and multi-lineage dysplasia.

5-Azacytidine and other cytidine analogs are approved for subcutaneous (SC) or intravenous (IV) administration to treat various proliferative disorders. The s-triazine ring of 5-azacytidine has a particular sensitivity to water. See, e.g., Beisler, *J. Med. Chem.*, 1978, 21(2), 204-08; Chan, et al., *J. Pharm. Sci.*, 1979, 68(7), 807-12. 5-Azacytidine is rapidly degraded in water. This characteristic has made the storage, handling, and administration of liquid formulations of 5-azacytidine a potential challenge. In addition, cytidine analogs may have limited aqueous solubility, for example, at a low temperature. As a result, the administration of liquid formulations of cytidine analogs may be difficult due to a combination of chemical instability and/or poor aqueous solubility.

Therefore, a great need remains for formulations and dosage forms of cytidine analogs (e.g., 5-azacytidine) and methods of preparing and using the formulations and dosage forms, to potentially permit, inter alia, convenient administration to patients, limited amount of impurities upon storage, suitable impurity profile to minimize potential toxicity, accurate delivery of intended dose, development of improved treatment regimens that maximize biologic activity, use of cytidine analogs for treating new diseases or disorders or new patient populations; and/or other potential advantageous benefits.

Citation of any references in this Section is not to be construed as an admission that such references are prior art to the present application.

3. SUMMARY

Provided herein are solid forms (e.g., crystal forms or amorphous forms, or mixtures thereof) comprising 5-azacytidine, or pharmaceutically acceptable salts, stereoisomers, solvates (including, hydrates), prodrugs, or clathrates thereof, and a coformer. Also provided are methods of preparing, isolating, and characterizing the solid forms.

Also provided herein are pharmaceutical compositions and single unit dosage forms, which comprise one or more solid forms provided herein.

Also provided herein are methods of treating and managing various diseases or disorders. The methods comprise administering to a patient in need of such treatment or management a therapeutically effective amount of a solid form provided herein.

The various diseases and disorders include but are not limited to: patho-physiological conditions manifested by abnormal cell proliferation, such as, for example, cancer, including hematological disorders and solid tumors, myelodysplastic syndromes (MDS), acute myeloid leukemia (AML), acute lymphoblastic leukemia (ALL), chronic myelogenous leukemia (CML), chronic lymphocytic leukemia (CLL), lymphoma (including non-Hodgkin's lymphoma (NHL) and Hodgkin's lymphoma), multiple myeloma (MM), sarcoma, melanoma, carcinoma, adenocarcinoma, chordoma, breast cancer, colorectal cancer, ovarian cancer, lung cancer (e.g., non-small-cell lung cancer and small-cell lung cancer), testicular cancer, renal cancer, pancreatic cancer, bone cancer, gastric cancer, head and neck cancer, and prostate cancer.

4. BRIEF DESCRIPTION OF THE DRAWINGS

FIG. 1 provides a representative X-ray Powder Diffraction (XRPD) pattern of one embodiment of a solid form comprising 5-azacytidine and mandelic acid.

Figure 2:
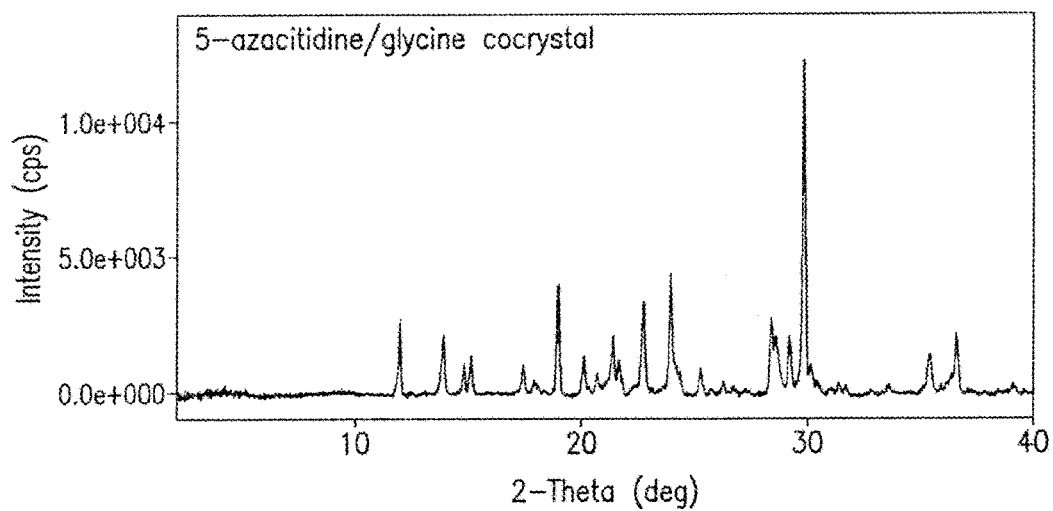

FIG. 2 provides a representative XRPD pattern of one embodiment of a solid form comprising 5-azacytidine and glycine.

Figure 3:
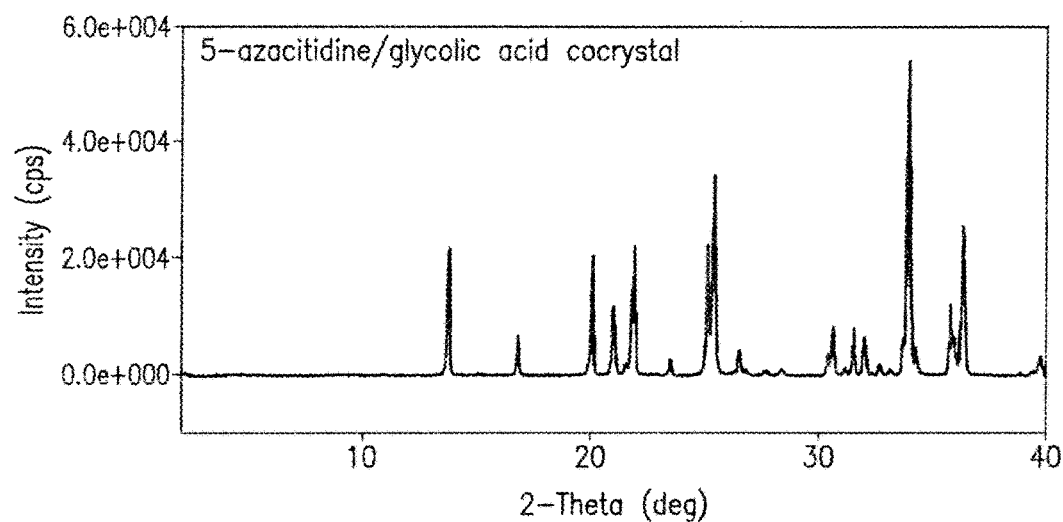

FIG. 3 provides a representative XRPD pattern of one embodiment of a solid form comprising 5-azacytidine and glycolic acid.

Figure 4:
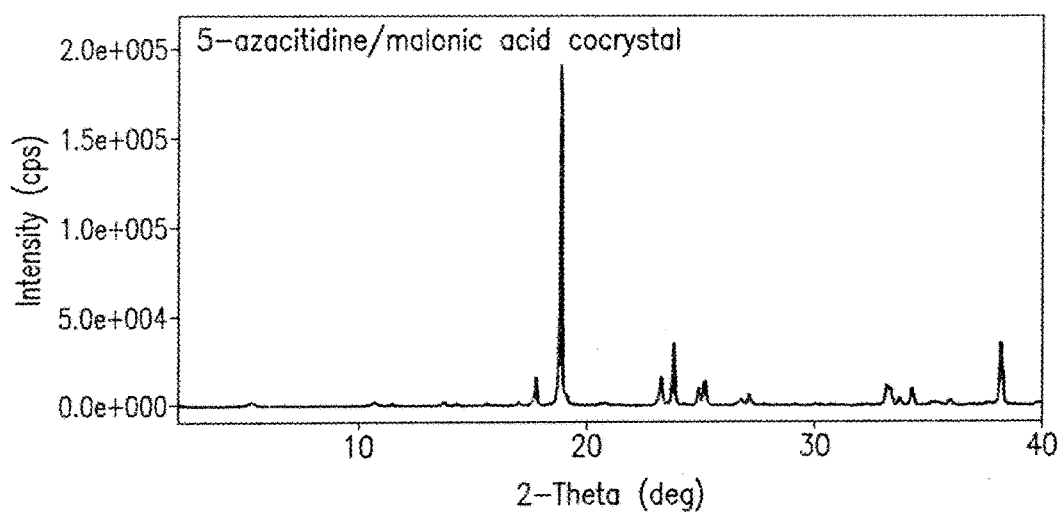

FIG. 4 provides a representative XRPD pattern of one embodiment of a solid form comprising 5-azacytidine and malonic acid.

Figure 5:
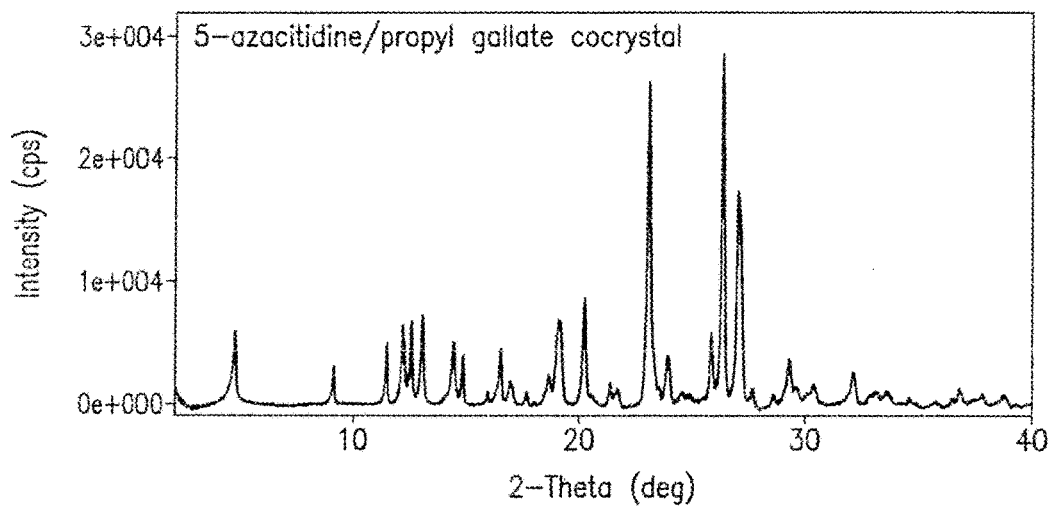

FIG. 5 provides a representative XRPD pattern of one embodiment of a solid form comprising 5-azacytidine and propyl gallate.

Figure 6:
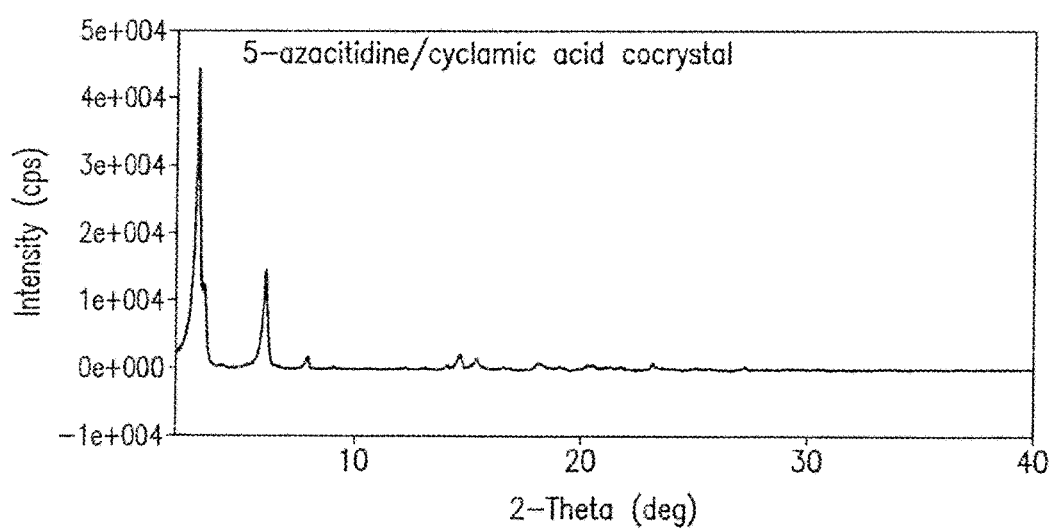

FIG. 6 provides a representative XRPD pattern of one embodiment of a solid form comprising 5-azacytidine and cyclamic acid.

Figure 7:
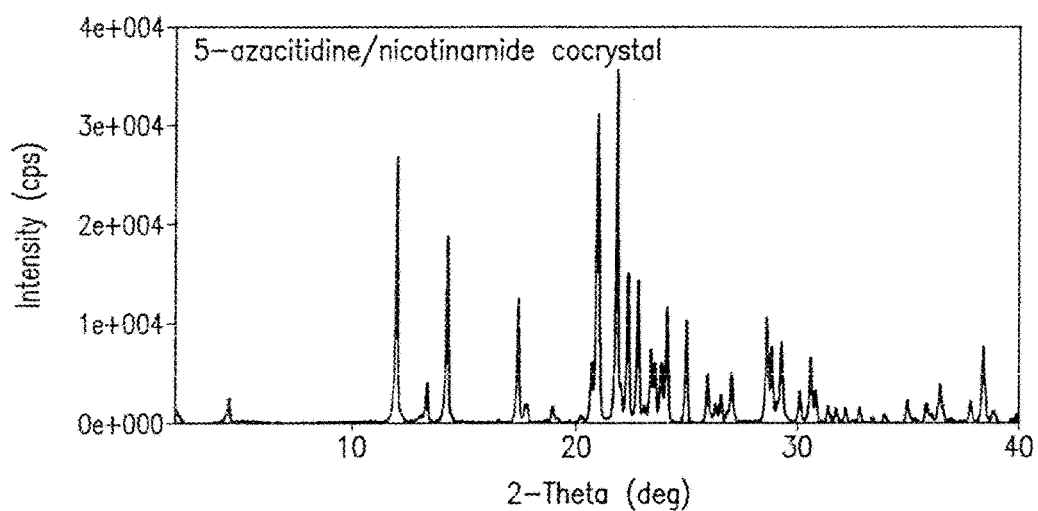

FIG. 7 provides a representative XRPD pattern of one embodiment of a solid form comprising 5-azacytidine and nicotinamide.

Figure 8:
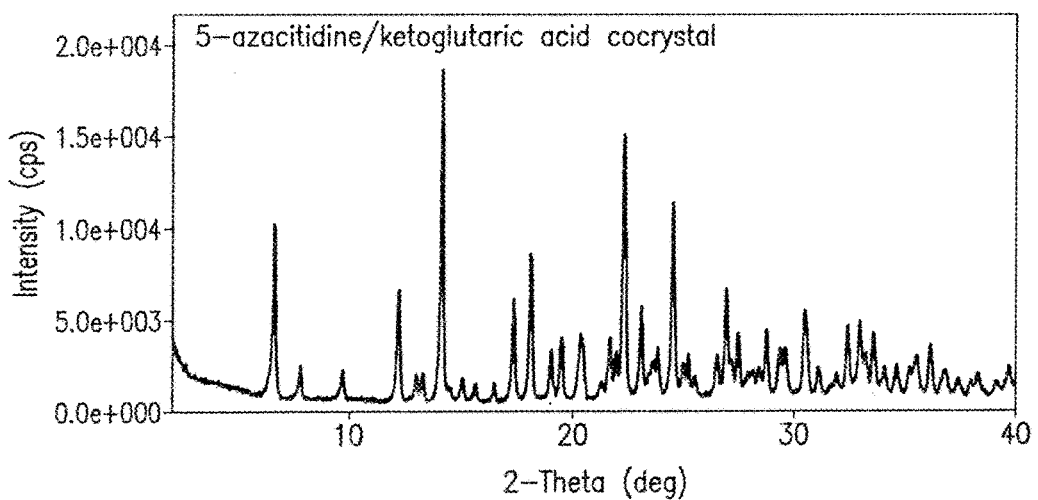

FIG. 8 provides a representative XRPD pattern of one embodiment of a solid form comprising 5-azacytidine and ketoglutaric acid.

Figure 9:
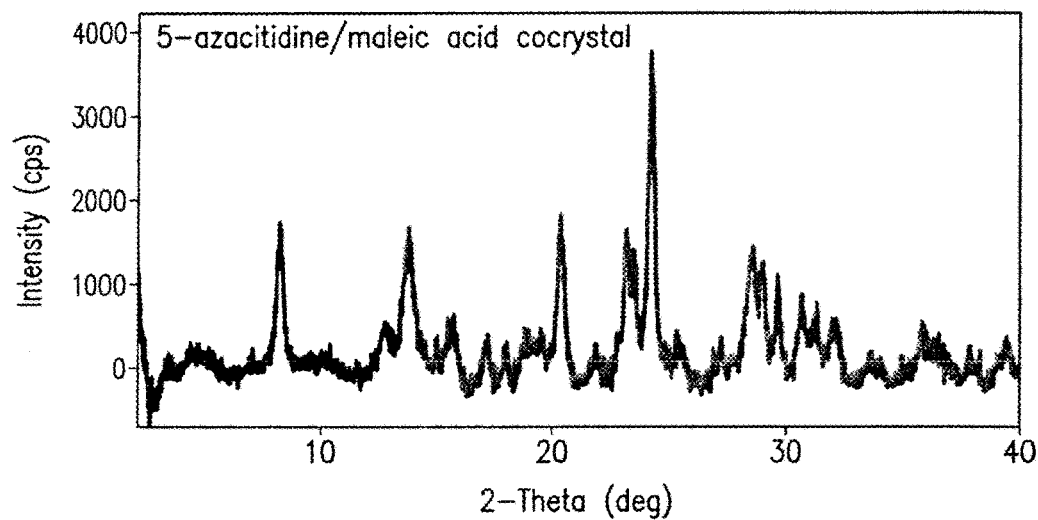

FIG. 9 provides a representative XRPD pattern of one embodiment of a solid form comprising 5-azacytidine and maleic acid.

Figure 10:
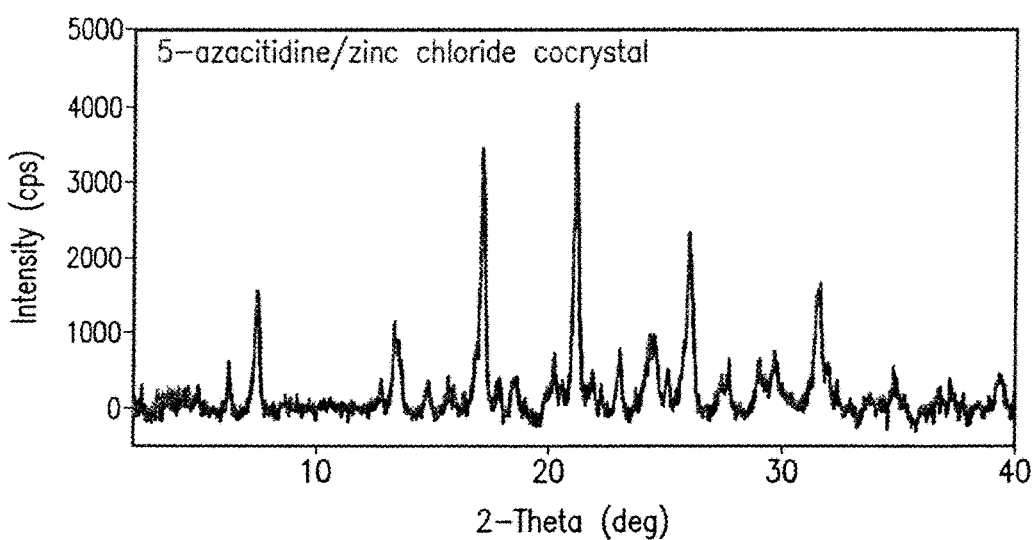

FIG. 10 provides a representative XRPD pattern of one embodiment of a solid form comprising 5-azacytidine and zinc chloride.

Figure 11:
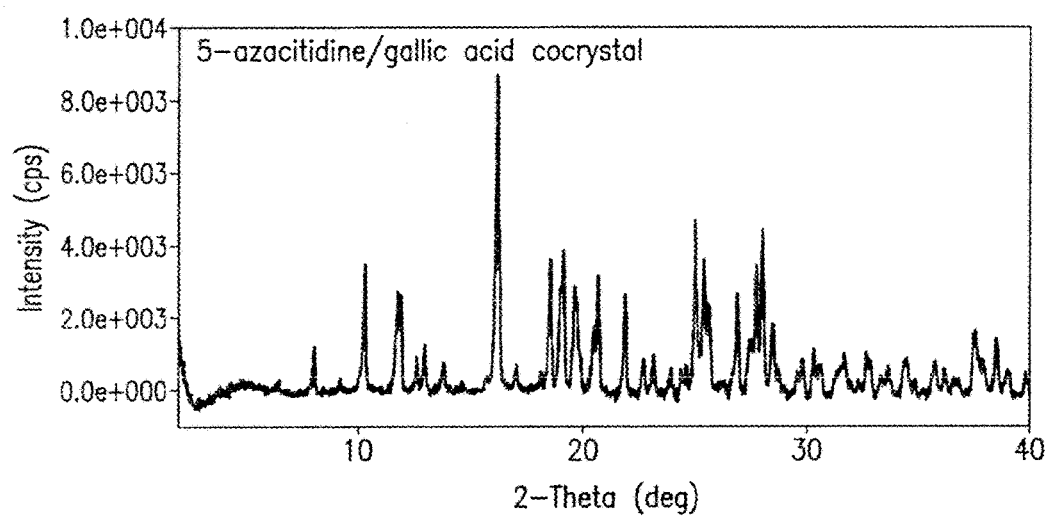
Figure 12A:
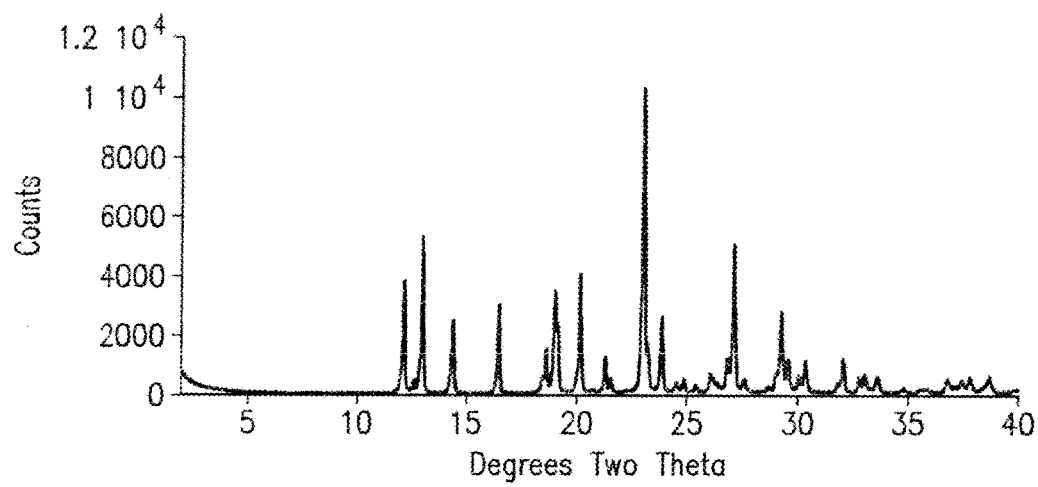
Figure 12B:
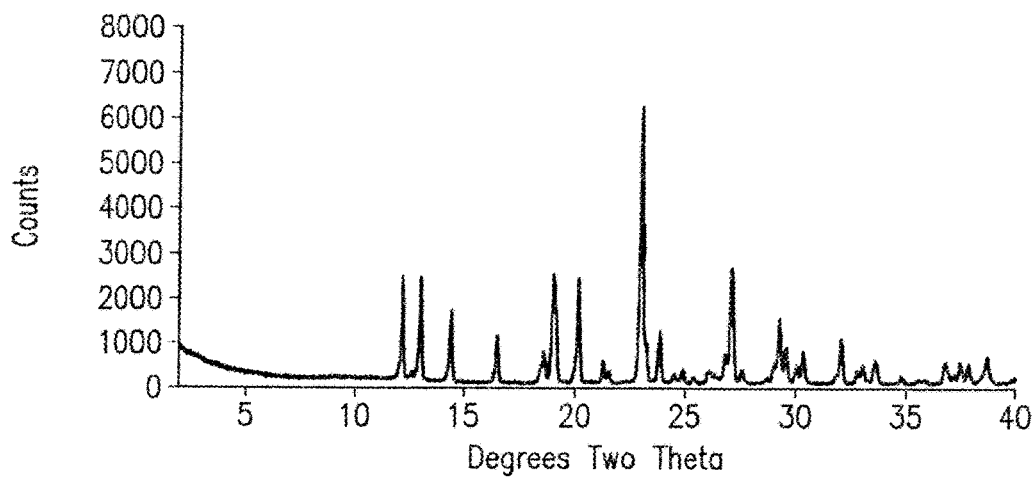
Figure 12C:
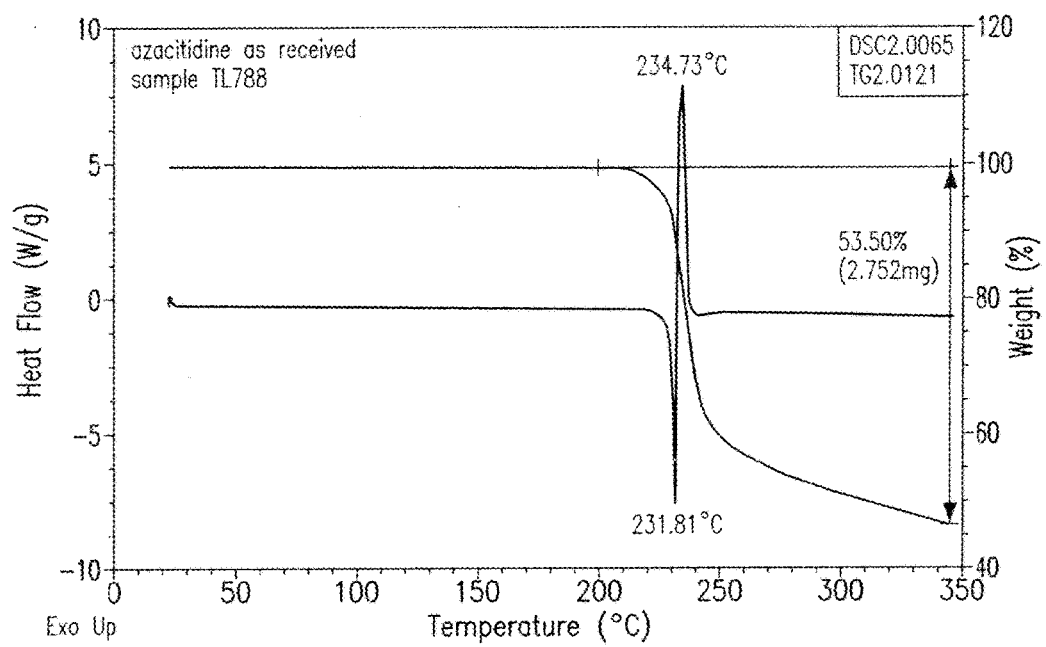
Figure 12D:
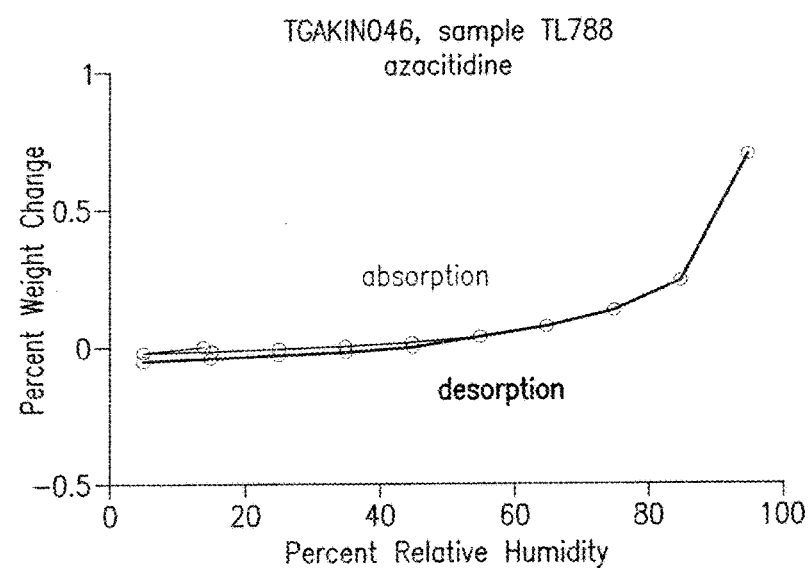

FIG. 11 provides a representative XRPD pattern of one embodiment of a solid form comprising 5-azacytidine and gallic acid.

FIG. 12 provides characterization data for 5-azacytidine. FIG. 12A provides a representative XRPD pattern of the solid form I of 5-azacytidine before dynamic vapor sorption (DVS) analysis. FIG. 12B provides a representative XRPD pattern of the solid form I of 5-azacytidine ( ) after dynamic vapor sorption (DVS) analysis. FIG. 12C provides representative differential scanning calorimetry (SC) and thermogravimetric (TG) analysis data for 5-azacytidine. FIG. 12D provides DVS analysis for 5-azacytidine.

FIG. 13 provides characterization data for 5-azacytidine/maleic acid cocrystals. FIG. 13A provides a representative XRPD pattern for products formed by a stoichiometric wet slurry process. FIG. 13B provides a representative XRPD pattern for products formed from a stoichiometric wet milling process before DVS analysis. FIG. 13C provides representative XRPD patterns for products formed from a stoichiometric wet milling process after DVS analysis FIG. 13D provides representative DSC and TG analysis data for 5-azacytidine/maleic acid cocrystals formed by stoichiometric wet milling. FIG. 13E provides DVS analysis 5-azacytidine/maleic acid cocrystals formed by stoichiometric wet milling.

FIG. 14 provides characterization data for 5-azacytidine/nicotinamide formed by a stoichiometric wet milling process. FIG. 14A provides a representative XRPD pattern for 5-azacytidine/nicotinamide acid cocrystal products before DVS analysis. FIG. 14B provides representative XRPD patterns for 5-azacytidine/nicotinamide acid cocrystal products after DVS analysis. FIG. 14C provides representative DSC and TG analysis data for 5-azacytidine/maleic acid cocrystals formed by stoichiometric wet milling. FIG. 14D provides DVS analysis 5-azacytidine/maleic acid cocrystals formed by stoichiometric wet milling.

FIG. 15 provides characterization data for 5-azacytidine/zinc chloride cocyrstal samples prepared a stoichiometric wet milling process. FIG. 15A provides representative XRPD patterns for 5-azacytidine/zinc chloride cocyrstal samples. FIG. 15B provides representative DSC and TG analysis data for 5-azacytidine/zinc chloride cocyrstal samples. FIG. 15C provides DVS analysis for 5-azacytidine/zinc chloride cocyrstal samples. FIG. 15D provides ion-selective electrode (ISE) titration data for 5-azacytidine/zinc chloride cocyrstal samples to determine the chloride ion content of the cocrystal.

Figure 16:
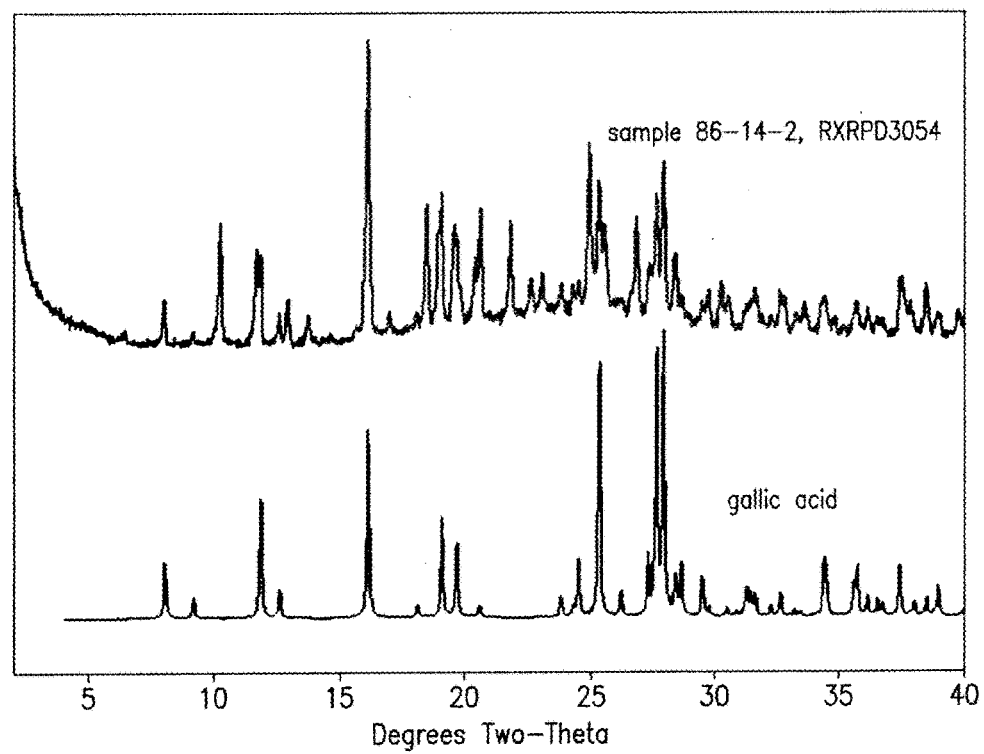

FIG. 16 provides an overlay plot of the XRPD patterns for samples of 5-azacytidine/cyclamic acid cocrystals with the XRPD pattern for cyclamic acid.

Figure 17:
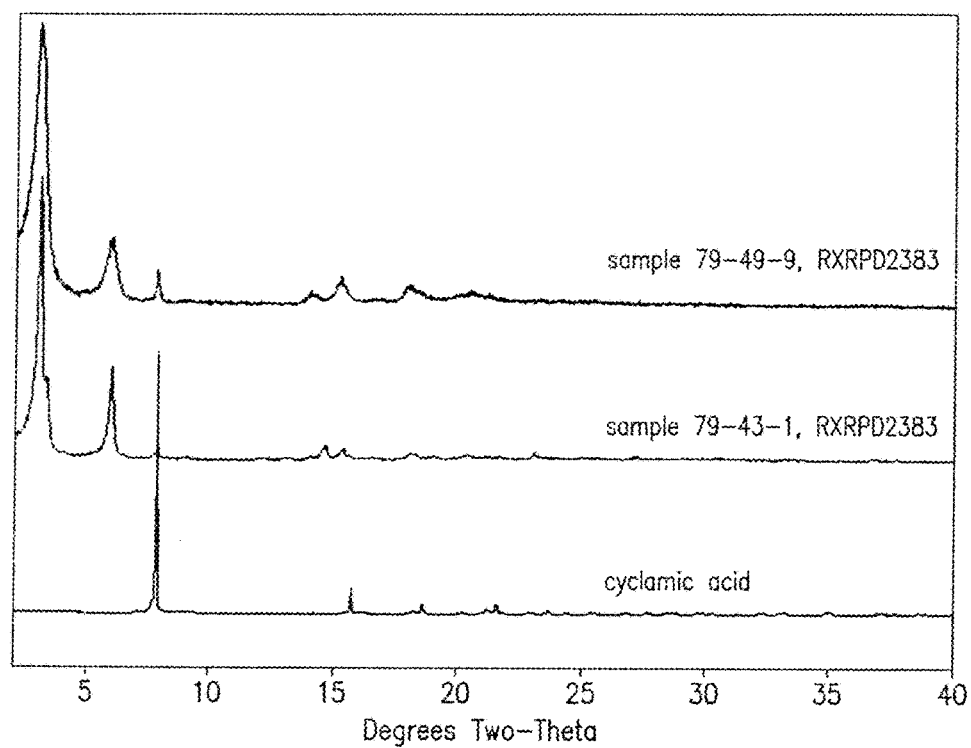

FIG. 17 provides an overlay plot of the XRPD pattern for a sample of a 5-azacytidine/gallic acid cocrystal with the XRPD pattern for gallic acid.

Figure 18:
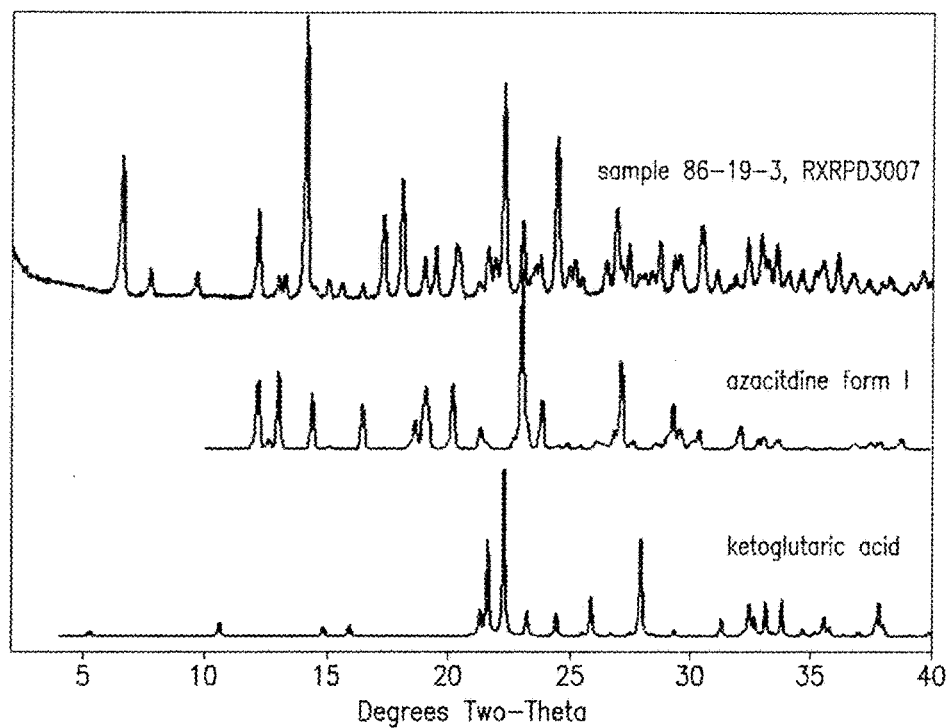

FIG. 18 provides an overlay plot of the XRPD pattern for a sample of a 5-azacytidine/ketoglutaric acid cocrystal with the XRPD pattern from 5-azacytidine form I and ketoglutaric acid.

Figure 19:
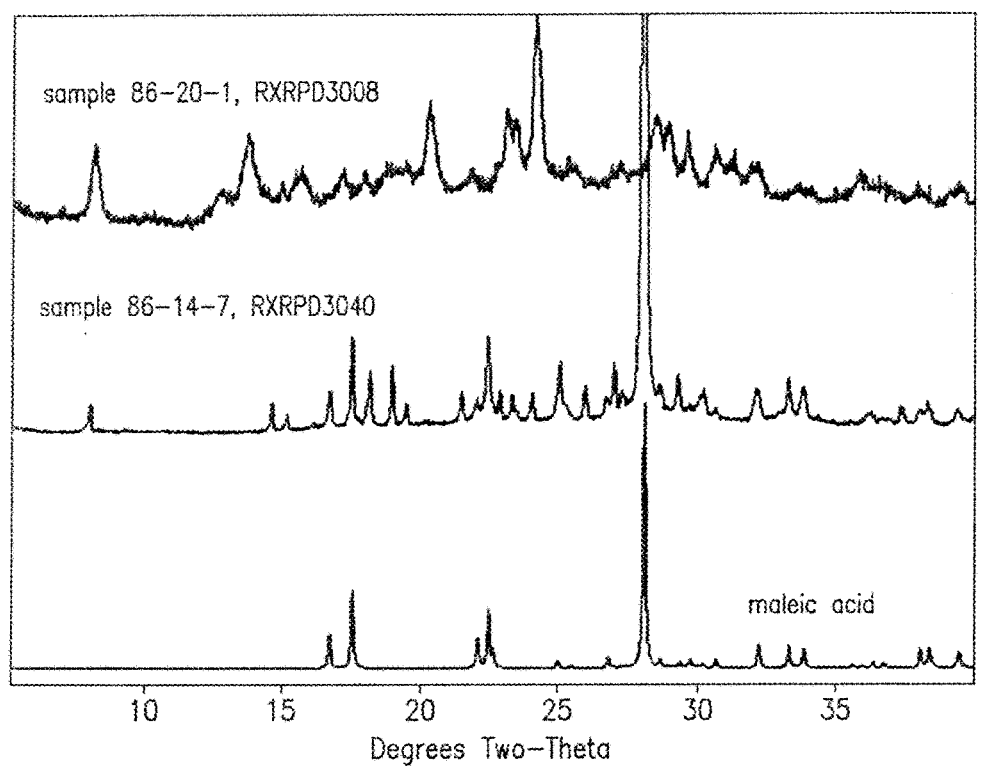

FIG. 19 provides an overlay plot of the XRPD patterns for samples of 5-azacytidine/maleic acid cocrystals with the XRPD pattern for maleic acid.

Figure 20:
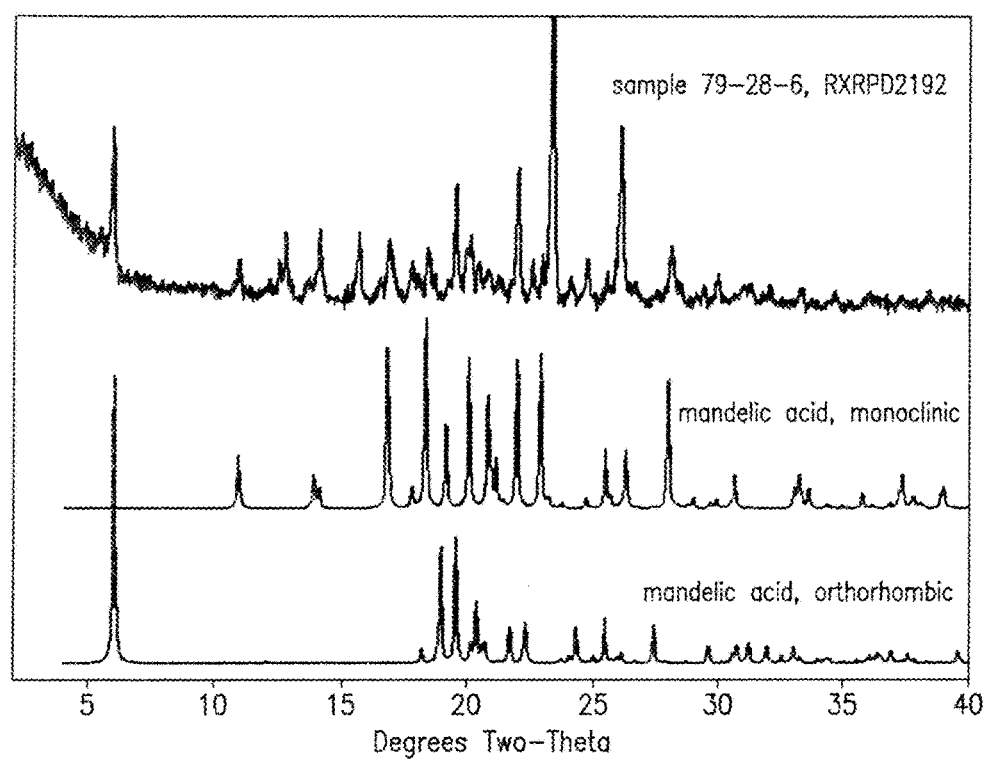

FIG. 20 provides an overlay plot of the XRPD pattern for a sample of a 5-azacytidine/mandelic cocrystal with the XRPD patterns for two polymorphs of mandelic acid.

Figure 21:
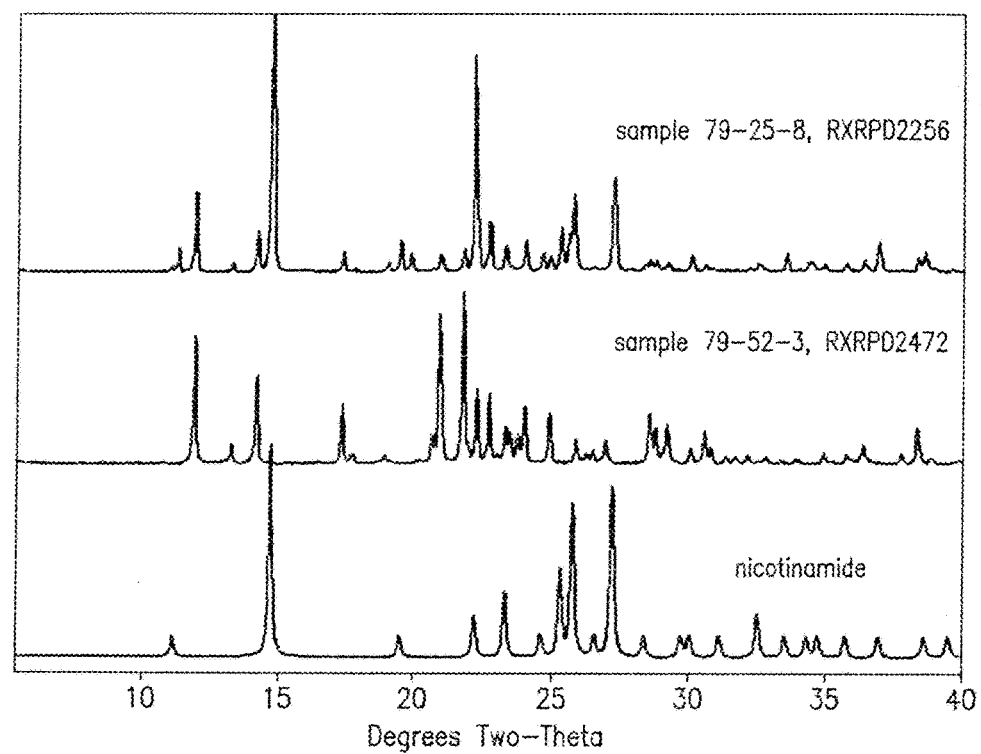

FIG. 21 provides an overlay plot of the XRPD patterns for samples of 5-azacytidine/nicotinamide cocrystals with the XRPD pattern for nicotinamide.

Figure 22:
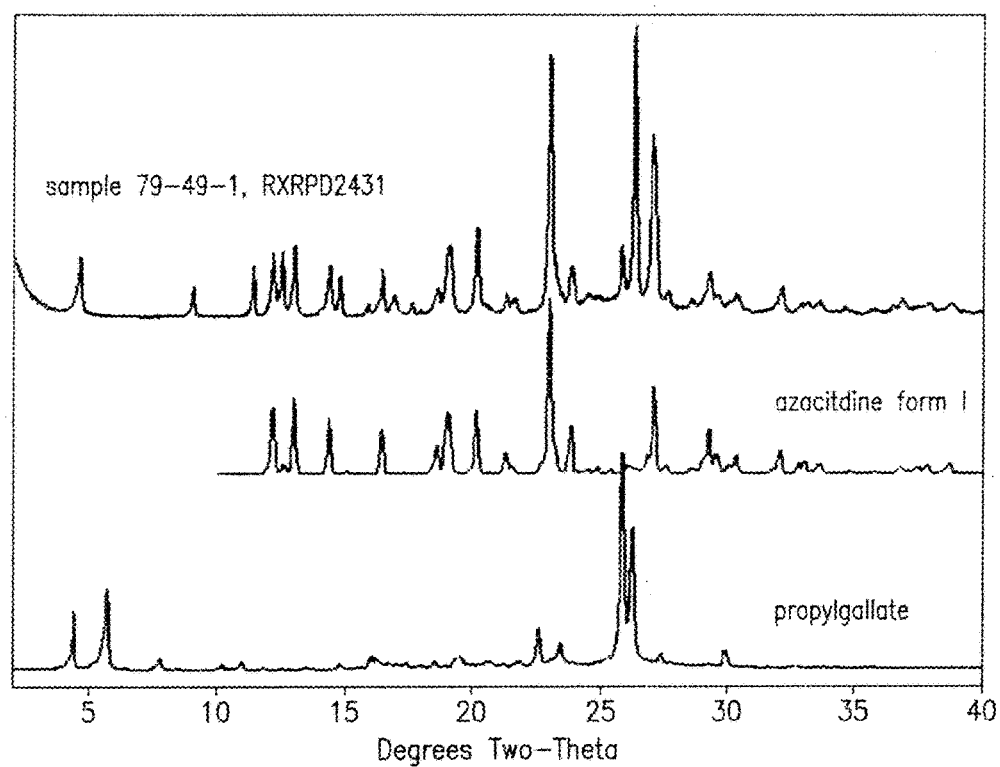

FIG. 22 provides an overlay plot of the XRPD patterns for samples of 5-azacytidine/propyl gallate cocrystals with the XRPD pattern for propyl gallate.

Figure 23:
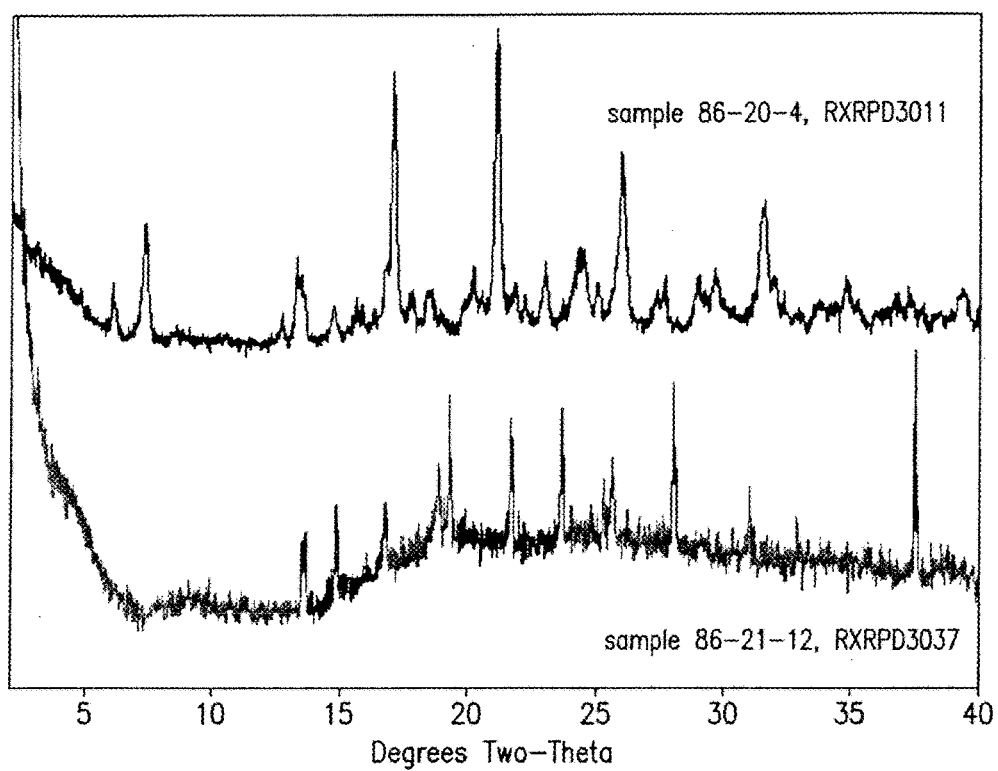
Figure 24A:
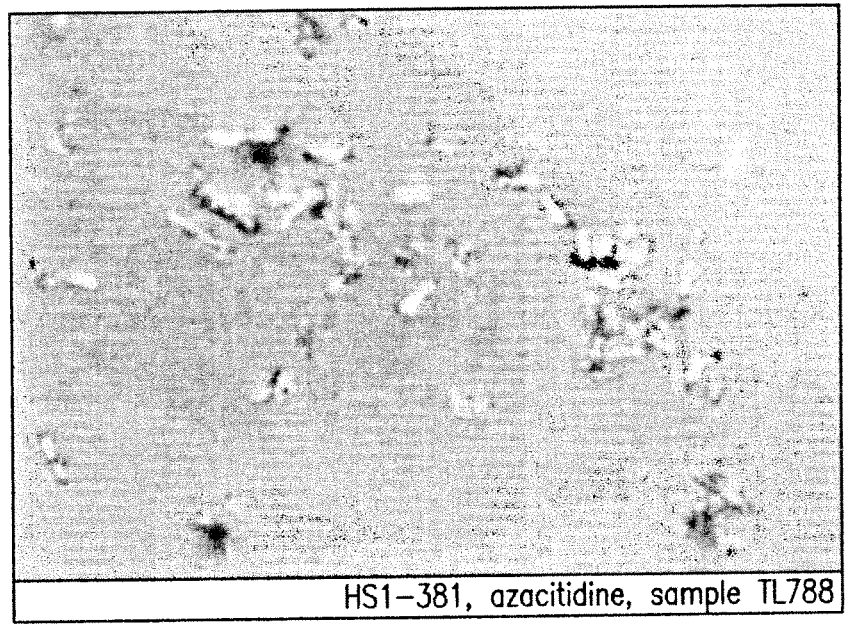
Figure 24B:
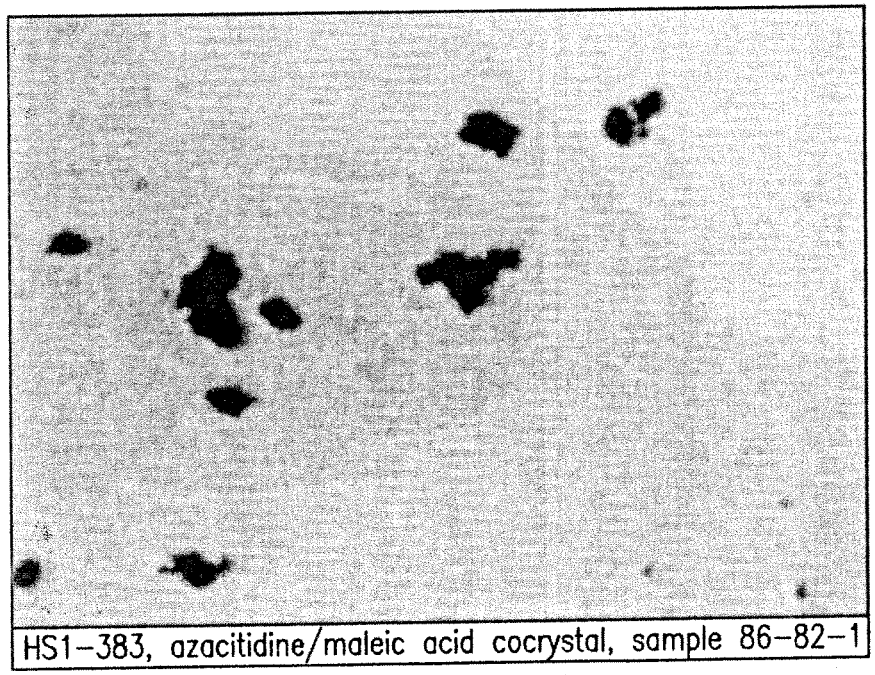
Figure 24C:
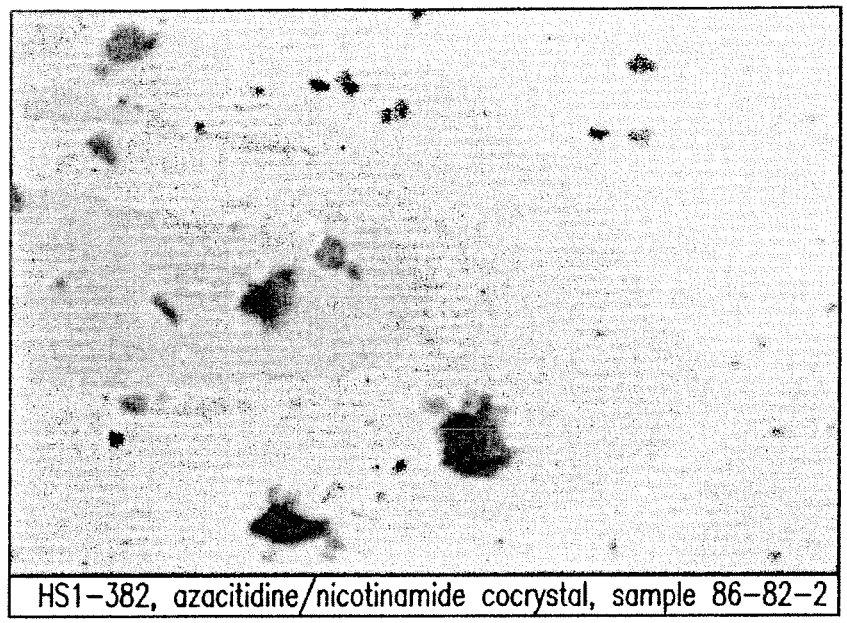
Figure 24D:
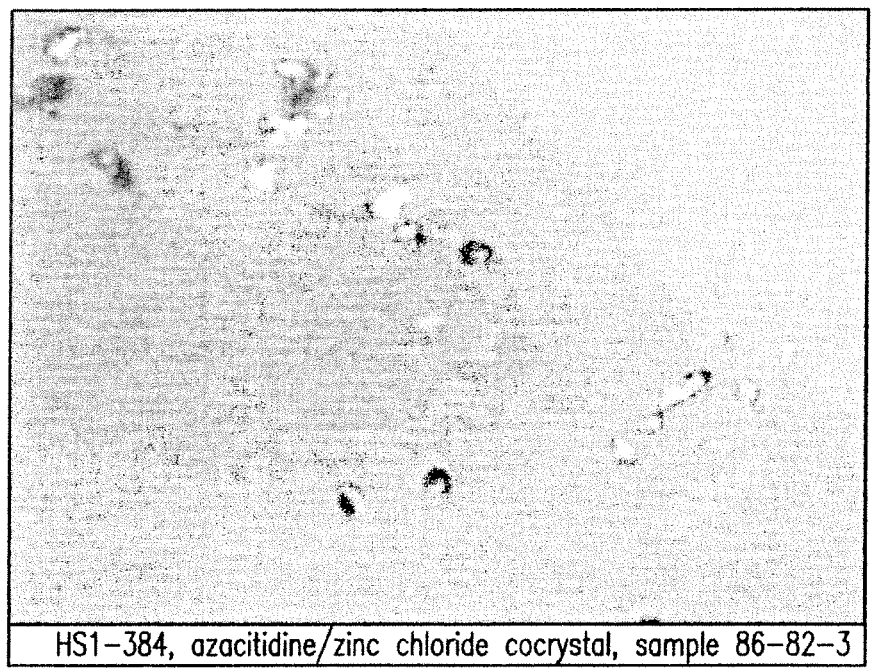

FIG. 23 provides an overlay plot of the XRPD patterns for two samples of 5-azacytidine/zinc chloride cocrystals.

FIG. 24 provides optical microscopy data for solid forms of 5-azacytidine with and without conformers. FIG. 24A provides optical microscopy data for a pure sample of 5-azacytidine. FIG. 24B provides optical microscopy data for 5-azacytidine/maleic acid cocrystals. FIG. 24C provides optical microscopy data for 5-azacytidine/nicotinamde cocrystals. FIG. 24D provides optical microscopy data for azacytidine/zinc chloride cocrystals.

5. DETAILED DESCRIPTION

5.1 Definitions

As used herein, and in the specification and the accompanying claims, the indefinite articles "a" and "an" and the definite article "the" include plural as well as single referents, unless the context clearly indicates otherwise.

As used herein, and unless otherwise specified, the compound referred to herein by the name 5-Azacytidin, azacytidine, AZA, or 4-amino-1-β-D-ribofuranosyl-1,3,5-triazin-2(1H)-one corresponds to chemical structure (I), depicted below. In certain embodiments, the term 5-Azacytidin, azacytidine, AZA, or 4-amino-1-β-D-ribofuranosyl-1,3,5-triazin-2(1H)-one may be used herein to refer to either a free base form or an ionized form of a compound of formula (I) (e.g., the molecule is protonated at one or more basic centers).

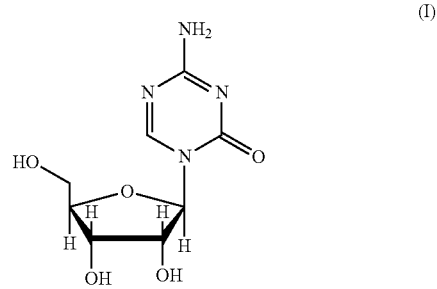

Unless otherwise specified, the terms "solid form," "solid forms," and related terms, when used herein to refer to 5-azacytidine, refer to a physical form comprising 5-azacytidine, which is not predominantly in a liquid or a gaseous state. As used herein, the terms "solid form" and "solid forms" encompass semi-solids. Solid forms may be crystalline, amorphous, partially crystalline, partially amorphous, or mixtures of forms. A "single-component" solid form comprising 5-azacytidine consists essentially of 5-azacytidine. A "multiple-component" solid form comprising 5-azacytidine comprises a significant quantity of one or more additional species, such as ions and/or molecules, within the solid form. For example, in particular embodiments, a crystalline multiple-component solid form comprising 5-azacytidine further comprises one or more species non-covalently bonded at regular positions in the crystal lattice. In one embodiment, the cytidine analogs provided herein may be prepared in a particular solid form (e.g., amorphous or crystalline form). See, e.g., U.S. patent application Ser. No. 10/390,578, filed Mar. 17, 2003 and U.S. patent application Ser. No. 10/390,530, filed Mar. 17, 2003, both of which are incorporated herein by reference in their entireties.

Unless otherwise specified, the term "crystalline" and related terms used herein, when used to describe a substance, component, product, or form, mean that the substance, component, product, or form is substantially crystalline, for example, as determined by X-ray diffraction. (see, e.g., *Remington's Pharmaceutical Sciences*, $18^{th}$ ed., Mack Publishing, Easton Pa., 173 (1990); *The United States Pharmacopeia*, $23^{rd}$ ed., 1843-1844 (1995)).

Unless otherwise specified, the term "crystal form," "crystal forms," and related terms herein refer to crystalline modifications comprising a given substance, including single-component crystal forms and multiple-component crystal forms, and including, but not limited to, polymorphs, solvates, hydrates, co-crystals, other molecular complexes, salts, solvates of salts, hydrates of salts, co-crystals of salts, and other molecular complexes of salts, and polymorphs thereof. In some embodiments, a crystal form of a substance may be substantially free of amorphous forms and/or other crystal forms. In other embodiments, a crystal form of a substance may contain less than about 1%, 2%, 3%, 4%, 5%, 10%, 15%, 20%, 25%, 30%, 35%, 40%, 45%, or 50% of one or more amorphous form(s) and/or other crystal form(s) on a weight basis. Crystal forms of a substance may be obtained by a number of methods. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, and solvent-drop grinding.

Unless otherwise specified, the terms "polymorph," "polymorphic form," "polymorphs," "polymorphic forms," and related terms herein refer to two or more crystal forms that consist essentially of the same molecule, molecules or ions. Different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

Unless otherwise specified, the term "cocrystal" or "co-crystal," as used herein, refers to a crystalline material comprised of two or more non-volatile compounds bound together in a crystal lattice by non-covalent interactions.

Unless otherwise specified, the term "pharmaceutical cocrystal" or "cocrystal" of an active pharmaceutical ingredient (API), as used herein, refers to a crystalline material comprised of an API and one or more non-volative compound(s) (referred herein as a coformer). The API and the coformer interact through non-covalent forces in a crystal lattice.

Unless otherwise specified, the term "amorphous," "amorphous form," and related terms used herein mean that the substance, component, or product referred to is not substantially crystalline as determined by X-ray diffraction. In certain embodiments, an amorphous form of a substance may be substantially free of crystal forms. In other embodiments, an amorphous form of a substance may contain less than about 1%, 2%, 3%, 4%, 5%, 10%, 15%, 20%, 25%, 30%, 35%, 40%, 45% or 50% of one or more crystal forms on a weight basis. In other embodiments, an amorphous form of a substance may comprise additional components or ingredients (for example, an additive, a polymer, or an excipient that may serve to further stabilize the amorphous form). In some embodiments, amorphous form may be a solid solution. Amorphous forms of a substance can be obtained by a number of methods. Such methods include, but are not limited to, heating, melt cooling, rapid melt cooling, solvent evaporation, rapid solvent evaporation, desolvation, sublimation, grinding, ball-milling, cryo-grinding, spray drying, and freeze drying.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an XRPD peak position may vary by up to ±0.2 degrees two theta while still describing the particular XRPD peak.

As used herein, and unless otherwise specified, a crystalline or amorphous form that is "pure," i.e., substantially free of other crystalline or amorphous forms, contains less than about 10% by weight of one or more other crystalline or amorphous forms, less than about 5% by weight of one or more other crystalline or amorphous forms, less than about 3% by weight of one or more other crystalline or amorphous forms, or less than about 1% by weight of one or more other crystalline or amorphous forms.

As used herein, and unless otherwise specified, a solid form that is "substantially physically pure" is substantially free from other solid forms. In certain embodiments, a crystal form that is substantially physically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

As used herein, and unless otherwise specified, the term "pharmaceutically acceptable salts" refers to salts prepared from pharmaceutically acceptable, relatively non-toxic acids, including inorganic acids and organic acids.

In some embodiments, suitable acids include, but are not limited to, acetic, adipic, ascorbic, benzenesulfonic, benzoic, boric, camphorsulfonic, capric, caproic, caprylic, carbonic, cinnamic, citric, cyclamic, dihydrogenphosphoric, ethenesulfonic, formic, fumaric, galactaric, galactunoric, gentisic, gluconic, glucuronic, glutamic, glucolic, glycolic, hippuric, hydrobromic, hydrochloric, hydriodic, isobutyric, isethionic, lactic, lauric, maleic, malic, malonic, mandelic, methanesulfonic, monohydrogencarbonic, monohydrogenphosphoric, monohydrogensulfuric, mucic, nicotinic, nitric, oleic, oxalic, palmitic, pamoic, pantothenic, phosphoric, phthalic, propionic, saccharic, salicylic, sebacic, stearic, succinic, sulfuric, tartaric, thiocyanic, toluenesulfonic acid (including p-toluenesulfonic, m-toluenesulfonic, and o-toluenesulfonic acids), undecylenic, valeric, and the like (see, e.g., S. M. Berge et al., *J. Pharm. Sci.*, 66:1-19 (1977); and *Handbook of Pharmaceutical Salts: Properties, Selection and Use*, P. H. Stahl and C. G. Wermuth, Eds., (2002), Wiley, Weinheim). In some embodiments, suitable acids are strong acids (e.g., with pKa less than about 1), including, but not limited to, hydrochloric, hydrobromic, sulfuric, nitric, methanesulfonic, benzene sulfonic, toluene sulfonic, naphthalene sulfonic, naphthalene disulfonic, pyridine-sulfonic, or other substituted sulfonic acids. Also included are salts of other relatively non-toxic compounds that possess acidic character, including amino acids, such as aspartic acid and the like, and other compounds, such as aspirin, ibuprofen, saccharin, and the like. Acid addition salts can be obtained by contacting the neutral form of a compound with a sufficient amount of the desired acid, either neat or in a suitable solvent. As solids, salts can exist in crystalline or amorphous forms, or mixtures thereof. Salts can also exist in polymorphic forms.

Unless otherwise specified, the terms "solvate" and "solvated," as used herein, refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, co-crystal, or molecular complex. The terms "hydrate" and "hydrated," as used herein, can also refer to a hydrate of a salt, co-crystal, or molecular complex.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of a particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of a disease or disorder provided herein. The terms encompass the inhibition or reduction of a symptom of a particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread, or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease or one or more symptoms thereof.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, that provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or one or more symptoms thereof, or prevent the recurrence of the disease or disorder, or one or more symptoms thereof. A prophylactically effective amount of a compound means an amount of therapeutic agent, alone or in combination with other agents, that provides a prophylactic benefit in the prevention of the disease or disorder. The term "prophylactically effective amount" can encompass an amount that improves overall prophylaxis or enhances the prophylactic efficacy of another prophylactic agent.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

Unless otherwise specified, the term "therapeutically and prophylactically effective amount" refers to the amount of the subject solid form that will elicit the biological or medical response of a tissue, system, animal or human that is being sought by the researcher, veterinarian, medical doctor or other clinician or that is sufficient to prevent development of or alleviate to some extent one or more of the symptoms of the disease being treated.

Unless otherwise specified, the term "subject" is defined herein to include animals, such as mammals, including, but not limited to, primates (e.g., humans), cows, sheep, goats, horses, dogs, cats, rabbits, rats, mice, and the like. In specific embodiments, the subject is a human.

Unless otherwise specified, to the extent that there is a discrepancy between a depicted chemical structure of a compound provided herein and a chemical name of a compound provided herein, the chemical structure shall control.

5.2 Solid Forms Comprising 5-Azacytidine and a Coformer

In one embodiment, provided herein are solid forms (e.g., crystal forms, amorphous forms, or mixtures thereof) comprising (a) 5-azacytidine, or a pharmaceutically acceptable salt, solvate, hydrate, stereoisomer, prodrug, or clathrate thereof; and (b) a coformer. In one embodiment, provided herein are solid forms (e.g., crystal forms, amorphous forms, or mixtures thereof) comprising (a) a free base of 5-azacytidine, or a solvate, hydrate, stereoisomer, prodrug, or clathrate thereof; and (b) a coformer. 5-azacytidine can be synthesized or obtained according to a method known in the literature or based upon the teachings herein, including the methods described in detail in the examples herein.

In one embodiment, 5-azacytidine can be prepared according to methods described in, for example, U.S. Pat. Nos. 7,038,038, 7,858,774, and 8,058,424, the entireties of which are incorporated herein by reference. Other embodiments provide 5-azacytidine in solid forms, which can be prepared, for example, according to the methods described in U.S. Pat. Nos. 6,943,249, 6,887,855 and 7,078,518, and U.S. Patent Application Publication Nos. 2005/027675 and 2006/247189, each of which is incorporated by reference herein in their entireties. In other embodiments, 5-azacytidine in solid forms can be prepared using other methods known in the art.

The coformer can be any pharmaceutically acceptable coformer known in the art. In one embodiment, the coformer is acetylsalicylic acid, D-glucose, nicotinic acid, aconitic acid, L-glutamic acid, oxalic acid, adipic acid, glutaric acid, L-proline, 4-aminosalicylic acid, glycine, propyl gallate, L-ascorbic acid, glycolic acid, L-pyroglutamic acid, benzoic acid, hippuric acid, saccharin, (+)-camphoric acid, 1-hydroxy-2-naphthoic acid, salicylic acid, capric acid, ketoglutaric acid, sebacic acid, cinnamic acid, L-lysine, sodium lauryl sulfate, citric acid, magnesium bromide, sorbic acid, cyclamic acid, maleic acid, succinic acid, ethyl maltol, L-malic acid, L-tartaric acid, ethyl paraben, malonic acid, urea, D-fructose, maltol, vanillic acid, fumaric acid, D,L-mandelic acid, vanillin, gallic acid, methyl paraben, zinc chloride, gentisic acid, or nicotinamide.

In one embodiment, the coformer is cyclamic acid, gallic acid, glycine, glycolic acid, ketoglutaric acid, maleic acid, malonic acid, mandelic acid, nicotinamide, propyl gallate or zinc chloride.

In one embodiment, solid forms provided herein may be a crystal form or an amorphous form or mixtures thereof (e.g., mixtures of crystal forms, or mixtures of crystal and amorphous forms), which comprises (a) 5-azacytidine or a pharmaceutically acceptable salt, solvate, hydrate, stereoisomer, prodrug, or clathrate thereof; and (b) a coformer. In one embodiment, provided herein is a crystal form comprising (a) 5-azacytidine or a pharmaceutically acceptable salt, solvate, hydrate, stereoisomer, prodrug, or clathrate thereof; and (b) a coformer. In one embodiment, provided herein is a cocrystal comprising (a) 5-azacytidine or a pharmaceutically acceptable salt, solvate, hydrate, stereoisomer, prodrug, or clathrate thereof; and (b) a coformer. In one embodiment, provided herein is an amorphous form comprising (a) 5-azacytidine or a pharmaceutically acceptable salt, solvate, hydrate, stereoisomer, prodrug, or clathrate thereof; and (b) a coformer. In one embodiment, provided herein is a mixture comprising (i) a cocrystal comprising (a) 5-azacytidine or a pharmaceutically acceptable salt, solvate, hydrate, stereoisomer, prodrug, or clathrate thereof; and (b) a coformer; and (ii) a crystal form of 5-azacytidine or a pharmaceutically acceptable salt, solvate, hydrate, stereoisomer, prodrug, or clathrate thereof. In one embodiment, provided herein is a mixture comprising (i) a cocrystal comprising (a) 5-azacytidine or a pharmaceutically acceptable salt, solvate, hydrate, stereoisomer, prodrug, or clathrate thereof; and (b) a coformer; and (ii) an amorphous form of 5-azacytidine or a pharmaceutically acceptable salt, solvate, hydrate, stereoisomer, prodrug, or clathrate thereof.

In one embodiment, provided herein is an unsolvated solid form comprising (a) 5-azacytidine and (b) a coformer. In one embodiment, provided herein is an anhydrous solid form comprising (a) 5-azacytidine and (b) a coformer. In one embodiment, provided herein is an unsolvated crystal form comprising (a) 5-azacytidine and (b) a coformer. In one embodiment, provided herein is an anhydrous crystal form comprising (a) 5-azacytidine and (b) a coformer. In one embodiment, provided herein is an unsolvated amorphous form comprising (a) 5-azacytidine and (b) a coformer. In one embodiment, provided herein is an anhydrous amorphous form comprising (a) 5-azacytidine and (b) a coformer. In one embodiment, provided herein is a solvated solid form comprising (a) 5-azacytidine and (b) a coformer. In one embodiment, provided herein is a hydrated solid form comprising (a) 5-azacytidine and (b) a coformer (e.g., a hydrate having a stoichiometric or non-stoichiometric amount of water). In one embodiment, provided herein is a hydrated form of (a) 5-azacytidine and (b) a coformer, including, but not limited to, a hemihydrate, a monohydrate, a dihydrate, a trihydrate, and the like. In one embodiment, the hydrated form is substantially crystalline. In one embodiment, the hydrated form is substantially amorphous. In one embodiment, the anhydrous form is substantially crystalline. In one embodiment, the anhydrous form is substantially amorphous. In one embodiment, provided herein is an unsolvated cocrystal comprising (a) 5-azacytidine and (b) a coformer. In one embodiment, provided herein is an anhydrous cocrystal comprising (a) 5-azacytidine and (b) a coformer. In one embodiment, provided herein is a hydrated cocrystal comprising (a) 5-azacytidine and (b) a coformer. In one embodiment, provided herein is a solvated cocrystal comprising (a) 5-azacytidine and (b) a coformer.

Solid forms provided herein can be prepared by the methods described herein, or by techniques, including, but not limited to, heating, cooling, freeze drying, spray drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces, such as, e.g., in nanopores or capillaries, recrystallization on surfaces or templates, such as, e.g., on polymers, recrystallization in the presence of additives, such as, e.g., co-crystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation, and precipitation from a supercritical fluid. The particle size of the resulting solid forms, which can vary (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing, or sonication.

In another embodiment, provided herein are compositions comprising one or more solid form(s) comprising (a) 5-azacytidine or a pharmaceutically acceptable salt, solvate, hydrate, stereoisomer, prodrug, or clathrate thereof; and (b) a coformer. Also provided herein are compositions comprising: (i) one or more solid form(s) provided herein (e.g., one or more crystal forms, one or more amorphous forms, and mixtures thereof), and (ii) other active ingredient(s). Also provided herein are methods of using these compositions in the treatment, prevention, or management of conditions and disorders including, but not limited to: patho-physiological conditions manifested by abnormal cell proliferation, such as, for example, cancer, including hematological disorders and solid tumors, MDS, AML, ALL, CML, chronic CLL, lymphoma (including non-Hodgkin's lymphoma and Hodgkin's lymphoma), MM, sarcoma, melanoma, carcinoma, adenocarcinoma, chordoma, breast cancer, colorectal cancer, ovarian cancer, lung cancer (e.g., non-small-cell lung cancer and small-cell lung cancer), testicular cancer, renal cancer, pancreatic cancer, bone cancer, gastric cancer, head and neck cancer, and prostate cancer.

cancer, including hematologic cancer or solid tumor, for example, multiple myeloma, leukemia, lymphoma, sarcoma, prostate cancer, or small cell lung cancer; scleroderma; amyloidosis; pain; myelofibrosis; myeloproliferative disease, e.g., MMM; myelodysplastic syndromes; diffuse systemic sclerosis; macular degeneration; a skin disease; a pulmonary disorder; an asbestos-related disorder; a parasitic disease; an immunodeficiency disorder; a CNS disorder; a CNS injury; atherosclerosis; hemoglobinopathy; anemia, e.g., sickle cell anemia; an inflammatory disease; an autoimmune disease; a viral disease; a genetic disease; an allergic disease; a bacterial disease; an ocular neovascular disease; a choroidal neovascular disease; a retina neovascular disease; and rubeosis.

While not intending to be bound by any particular theory, certain solid forms provided herein exhibit physical properties, e.g., stability, solubility and/or dissolution rate, appropriate for use in clinical and therapeutic dosage forms. Moreover, while not wishing to be bound by any particular theory, certain solid forms provided herein exhibit physical properties, e.g., crystal morphology, compressibility and/or hardness, suitable for manufacture of a solid dosage form. In some embodiments, such properties can be determined using techniques such as X-ray diffraction, microscopy, IR spectroscopy and thermal analysis, as described herein and known in the art.

Certain embodiments herein provide solid forms comprising (a) 5-azacytidine and (b) a coformer. In one embodiment, provided herein is a solid form comprising (a) 5-azacytidine and (b) a coformer that is substantially crystalline. In one embodiment, provided herein is a cocrystal comprising (a) 5-azacytidine and (b) a coformer. In one embodiment, provided herein is a solid form comprising a cocrystal comprising (a) 5-azacytidine and (b) a coformer. In one embodiment, provided herein is a solid form comprising (i) a cocrystal comprising (a) 5-azacytidine and (b) a coformer and (ii) an amorphous form of 5-azacytidine. In one embodiment, provided herein is a solid form comprising (i) a cocrystal comprising (a) 5-azacytidine and (b) a coformer and (ii) one or more additional crystal forms of 5-azacytidine.

In some embodiments, the cocrystal comprising (a) 5-azacytidine and (b) a coformer can be obtained by crystallization from certain solvent systems, for example, solvent systems comprising one or more of the following solvents: acetone, N,N-dimethylformamide (DMF), dimethyl sulfoxide (DMSO), tetrahydrofuran (THF), water and methanol. Other examples of solvent systems are provided herein elsewhere. In certain embodiments, a solid form provided herein (e.g., a cocrystal comprising (a) 5-azacytidine and (b) a coformer) can be obtained by slurry crystallization, evaporation crystallization, cooling crystallization, and precipitation crystallization.

In certain embodiments, the non-covalent forces are one or more hydrogen bonds (H-bonds). The coformer may be H-bonded directly to the API or may be H-bonded to an additional molecule which is bound to the API. The additional molecule may be H-bonded to the API or bound ionically or covalently to the API. The additional molecule could also be a different API. In certain embodiments, the co-crystals may include one or more solvate molecules in the crystalline lattice, i.e., solvates of co-crystals, or a co-crystal further comprising a solvent or compound that is a liquid at room temperature. In certain embodiments, the co-crystals may be a co-crystal between a coformer and a salt of an API. In certain embodiments, the non-covalent forces are pi-stacking, guest-host complexation and/or van der Waals interactions. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads.

In certain embodiments, the coformer is a solid under ambient temperature conditions when in its pure form. In certain embodiments, the coformer is selected from acetylsalicylic acid, D-glucose, nicotinic acid, aconitic acid, L-glutamic acid, oxalic acid, adipic acid, glutaric acid, L-proline, 4-aminosalicylic acid, glycine, propyl gallate, L-ascorbic acid, glycolic acid, L-pyroglutamic acid, benzoic acid, hippuric acid, saccharin, (+)-camphoric acid, 1-hydroxy-2-naphthoic acid, salicylic acid, capric acid, ketoglutaric acid, sebacic acid, cinnamic acid, L-lysine, sodium lauryl sulfate, citric acid, magnesium bromide, sorbic acid, cyclamic acid, maleic acid, succinic acid, ethyl maltol, L-malic acid, L-tartaric acid, ethyl paraben, malonic acid, urea, D-fructose, maltol, vanillic acid, fumaric acid, D,L-mandelic acid, vanillin, gallic acid, methyl paraben, zinc chloride, gentisic acid, and nicotinamide. In certain embodiments, the coformer is a second API.

In certain embodiments, the co-crystals include an acid addition salt or base addition salt of an API. Acid addition salts include, but are not limited to, inorganic acids such as hydrochloric acid, hydrobromic acid, sulfuric acid, nitric acid, and phosphoric acid, and organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutaric acid, hydroxynaphthoic acid, salicylic acid, stearic acid, and muconic acid. Base addition salts include, but are not limited to, inorganic bases such as sodium, potassium, lithium, ammonium, calcium and magnesium salts, and organic bases such as primary, secondary and tertiary amines (e.g., isopropylamine, trimethyl amine, diethyl amine, tri(isopropyl) amine, tri(n-propyl) amine, ethanolamine, 2-dimethylaminoethanol, tromethamine, lysine, arginine, histidine, procaine, hydrabamine, choline, betaine, ethylenediamine, glucosamine, N-alkylglucamines, theobromine, purines, piperazine, piperidine, morpholine, and N-ethylpiperidine).

The ratio of API to coformer may be stoichiometric or non-stoichiometric. In one embodiment, the ratio of API to coformer is about 5:1, 4:1, 3:1, 2.5:1, 2:1, 1.5:1, 1:1, 1:1.5, 1:2, 1:2.5, 1:3, 1:4, or 1:5. In one embodiment, the ratio of API to coformer is about 1:1. In one embodiment, the co-crystal comprises more than one coformers. In one embodiment, the co-crystal comprises two coformers.

In certain embodiments, cocrystals can be prepared using solid-state methods such as solid-state grinding and solvent-drop grinding. In certain embodiments, cocrystals can be prepared using high-throughput screening. In certain embodiments cocrystals can be prepared using solution-based crystallization.

In certain embodiments, cocrystals formation can lead to enhancement of physical properties of the resulting solid forms, such as solubility, dissolution rate, bioavailablity, physical stability, chemical stability, flowability, fractability, or compressibility. In certain embodiments, a given API may form different cocrystals with many different counter-molecules, and some of these cocrystals may exhibit enhanced solubility or stability. In certain embodiments pharmaceutical cocrystals increase the bioavailability or stability profile of a compound without the need for chemical (covalent) modification of the API.

The compounds provide herein may also contain an unnatural proportion of an atomic isotope at one or more of the atoms that constitute such a compound. For example, the compound may be radiolabeled with radioactive isotopes, such as for example tritium ($^3$H), iodine-125 ($^{125}$I) sulfur-35 ($^{35}$S), or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of the compounds provided herein, whether radioactive or not, are intended to be encompassed herein. In certain embodiments, a compound provided herein contains unnatural proportion(s) of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), ($^{14}$N), nitrogen-13 ($^{13}$N), nitrogen-14 nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, a compound provided herein contains unnatural proportion(s) of one or more isotopes in a stable form, that is, non-radioactive, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, a compound provided herein contains unnatural proportion(s) of one or more isotopes in an unstable form, that is, radioactive, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). In certain embodiments, in a compound as provided herein, any hydrogen can be $^2$H, for example, or any carbon can be $^{13}$C, for example, or any nitrogen can be $^{15}$N, for example, or any oxygen can be $^{18}$O, for example, where feasible according to the judgment of one of skill. In certain embodiments, a compound provided herein contains unnatural proportions of deuterium (D).

In certain embodiments, slurry crystallization is effected by adding solvent or solvent mixtures to a solid substrate, and the slurry is stirred, and optionally heated to various temperatures. In certain embodiments, the slurry is heated at about 25° C., about 50° C., about 80° C., or about 100° C. In certain embodiments, upon heating and cooling, the residual solvents of the slurry can be removed by wicking, or other suitable methods, such as filtration, centrifugation, or decantation, and the crystals can be dried in air or under vacuum.

In certain embodiments, evaporation crystallization is effected by adding a solvent or solvent mixture to a solid substrate, and allowing the solvent or solvent mixture to evaporate under ambient conditions. In certain embodiments, the residual solvent can be removed by wicking, or other suitable methods, such as filtration, centrifugation, or decantation, and the crystals can be dried in air or under vacuum.

In certain embodiments, precipitation crystallization is effected by adding a solvent or solvent mixture to a solid substrate, and subsequently adding an anti-solvent. In certain embodiments, the resultant mixture stands for a period of time, e.g., overnight, and under certain conditions, for example at room temperature. In certain embodiments, the residual solvent can be removed by wicking, or other suitable methods, such as filtration, centrifugation, or decantation, and the crystals can be dried in air or under vacuum.

In certain embodiments, cooling crystallization is effected by adding a solvent or solvent mixture to a solid substrate at elevated temperature, and allowing the resultant mixture to stand for a period of time at a reduced temperature. In certain embodiments, the elevated temperature is, for example, about 30° C., about 40° C., about 50° C., about 60° C., about 70° C., or about 80° C. In certain embodiments, the reduced temperature is, for example, about 15° C., about 10° C., about 5° C., about 0° C., about −5° C., about −10° C., about −15° C., or about −20° C. The residual solvent can be removed by wicking, or other suitable methods, such as filtration, centrifugation, or decantation, and the crystals can be dried in air or under vacuum.

5.2.1 Cocrystal Comprising 5-azacytidine and Mandelic Acid

Certain embodiments herein provide solid forms comprising 5-azacytidine and mandelic acid. In one embodiment, provided herein is a solid form comprising 5-azacytidine and mandelic acid that is substantially crystalline. In one embodiment, provided herein is a cocrystal comprising 5-azacytidine and mandelic acid. In one embodiment, provided herein is a solid form comprising a cocrystal comprising 5-azacytidine and mandelic acid. In one embodiment, provided herein is a solid form comprising (i) a cocrystal comprising 5-azacytidine and mandelic acid and (ii) an amorphous form of 5-azacytidine. In one embodiment, provided herein is a solid form comprising (i) a cocrystal comprising 5-azacytidine and mandelic acid and (ii) one or more additional crystal forms of 5-azacytidine. Provided herein are various embodiments, preparations, or modifications of a cocrystal comprising 5-azacytidine and mandelic acid.

In some embodiments, the cocrystal comprising 5-azacytidine and mandelic acid is obtained by mixing 5-azacytidine and mandelic acid in a solvent system. In some embodiments, the cocrystal is obtained by mixing 5-azacytidine and mandelic acid in a solvent system saturated with mandelic acid. In some embodiments, the cocrystal is obtained by mixing 5-azacytidine and mandelic acid in a solvent system saturated with mandelic acid, and subsequently stirring the mixture at room temperature for about 24 hours. In some embodiments, the cocrystal is obtained by mixing 5-azacytidine and mandelic acid in a solvent system saturated with mandelic acid, subsequently stirring the mixture at room temperature for about 24 hours, and isolating the solid by centrifugation. In some embodiments, the cocrystal is obtained by mixing approximately equal molar amount of 5-azacytidine and mandelic acid in a solvent system saturated with mandelic acid. In some embodiments, the solvent system is a mixed solvent of methanol and water with a volume ratio of methanol to water of about 1:3.

In some embodiments, the cocrystal comprising 5-azacytidine and mandelic acid is obtained by removing solvent from a solution containing 5-azacytidine and mandelic acid. In some embodiments, the cocrystal is obtained by removing solvent from a solution containing 5-azacytidine and mandelic acid on a rotary evaporator at about 80° C. In some embodiments, the cocrystal is obtained by removing solvent from a solution containing 5-azacytidine and mandelic acid, and subsequently storing the residue at about 75% relative humidity for 1 day. In some embodiments, the cocrystal is obtained by removing solvent from a solution containing 5-azacytidine and mandelic acid, and subsequently storing the residue at about 60° C. overnight. In some embodiments, the cocrystal is obtained by removing solvent from a solution containing approximately equal molar amount of 5-azacytidine and mandelic acid.

In some embodiments, provided herein is a cocrystal comprising 5-azacytidine and mandelic acid with a molar ratio of 5-azacytidine to mandelic acid of approximately 2:1 to 1:2. In some embodiments, the molar ratio of 5-azacytidine to mandelic acid is approximately 1:1.

A representative XRPD pattern of a solid form comprising 5-azacytidine and mandelic acid is provided in FIG. 1. In some embodiments, provided herein is a solid form comprising 5-azacytidine and mandelic acid characterized by one or more XRPD peaks (e.g., 1, 2, 3, 4, 5, 6, 7, 8, 9, 10, 11, 12, 13, 14, 15, 16, 17, 18, 19, 20 or more peaks) selected from peaks located at the following or approximately the following positions: 6.00, 12.51, 12.78, 14.09, 15.68, 16.85, 17.77, 18.39, 19.54, 19.94, 21.96, 22.54, 22.92, 23.27, 24.73, 25.49, 26.06, 28.02, 29.94, and 31.15 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising 5-azacytidine and mandelic acid having an XRPD pattern comprising peaks at approximately 23.27, 25.49, and 28.02 degrees 2θ. In certain embodiments, the solid form further comprises peaks at approximately 12.78, 17.77 and 22.92 degrees 2θ. In one embodiment, the solid form comprises peaks at approximately 12.51, 12.78, 15.68, 16.85, 17.77, 19.54, 21.96, 22.54, 22.92, 23.27, 24.73, 25.49, 28.02, 29.94, and 31.15 degrees 2θ.

In some embodiments, provided herein is a solid form comprising 5-azacytidine and mandelic acid having an XRPD pattern comprising peaks at approximately 16.85, 25.49, and 28.02 degrees 2θ. In some embodiments, provided herein is a solid form comprising 5-azacytidine and mandelic acid having an XRPD pattern comprising peaks at approximately 17.77, 25.49, and 28.02 degrees 2θ. In some embodiments, provided herein is a solid form comprising 5-azacytidine and gallic acid having an XRPD pattern comprising peaks at approximately 21.96, 25.49, and 28.02 degrees 2θ.

In some embodiments, provided herein is a solid form comprising 5-azacytidine and mandelic acid, wherein the solid form is characterized by an XRPD diffraction pattern which matches the XRPD pattern presented in FIG. 1.

5.2.2 Cocrystal Comprising 5-Azacytidine and Glycine

Certain embodiments herein provide solid forms comprising 5-azacytidine and glycine. In one embodiment, provided herein is a solid form comprising 5-azacytidine and glycine that is substantially crystalline. In one embodiment, provided herein is a cocrystal comprising 5-azacytidine and glycine. In one embodiment, provided herein is a solid form comprising a cocrystal comprising 5-azacytidine and glycine. In one embodiment, provided herein is a solid form comprising (i) a cocrystal comprising 5-azacytidine and glycine and (ii) an amorphous form of 5-azacytidine. In one embodiment, provided herein is a solid form comprising (i) a cocrystal comprising 5-azacytidine and glycine and (ii) one or more additional crystal forms of 5-azacytidine. Provided herein are various embodiments, preparations, or modifications of a cocrystal comprising 5-azacytidine and glycine.

In some embodiments, the cocrystal comprising 5-azacytidine and glycine is obtained by mixing 5-azacytidine and glycine in a solvent system. In some embodiments, the cocrystal is obtained by mixing 5-azacytidine and glycine in a solvent system saturated with glycine. In some embodiments, the cocrystal is obtained by mixing 5-azacytidine and glycine in a solvent system saturated with glycine, and subsequently stirring the mixture at room temperature for about 24 hours. In some embodiments, the cocrystal is obtained by mixing 5-azacytidine and glycine in a solvent system saturated with glycine, subsequently stirring the mixture at room temperature for about 24 hours, and isolating the solid by centrifugation. In some embodiments, the cocrystal is obtained by mixing approximately equal molar amount of 5-azacytidine and glycine in a solvent system saturated with glycine. In some embodiments, the solvent system is a mixed solvent of methanol and water with a volume ratio of methanol to water of about 1:2.

In some embodiments, the cocrystal comprising 5-azacytidine and glycine is obtained by removing solvent from a solution containing 5-azacytidine and glycine. In some embodiments, the cocrystal is obtained by removing solvent from a solution containing 5-azacytidine and glycine on a rotary evaporator at about 80° C. In some embodiments, the cocrystal is obtained by removing solvent from a solution containing 5-azacytidine and glycine, and subsequently storing the residue at about 75% relative humidity for 1 day. In some embodiments, the cocrystal is obtained by removing solvent from a solution containing 5-azacytidine and glycine, and subsequently storing the residue at about 60° C. overnight. In some embodiments, the cocrystal is obtained by removing solvent from a solution containing approximately equal molar amount of 5-azacytidine and glycine.

In some embodiments, provided herein is a cocrystal comprising 5-azacytidine and glycine with a molar ratio of 5-azacytidine to glycine of approximately 2:1 to 1:2. In some embodiments, the molar ratio of 5-azacytidine to glycine is approximately 1:1.

A representative XRPD pattern of a solid form comprising 5-azacytidine and glycine is provided in FIG. 2. In some embodiments, provided herein is a solid form comprising 5-azacytidine and glycine characterized by one or more XRPD peaks (e.g., 1, 2, 3, 4, 5, 6, 7, 8, 9, 10, 11, 12, 13, 14, 15, 16, 17, 18, 19, 20 21, 22, 23, 24, 25, 26, or more peaks) selected from peaks or more peaks) selected from peaks located at the following or approximately the following positions: 11.96, 13.87, 14.81, 15.10, 17.42, 17.88, 18.93, 20.10, 20.65, 21.38, 21.60, 22.62, 23.88, 25.24, 26.26, 28.39, 28.60, 29.19, 29.83, 30.14 30.45, 31.34, 35.34, 36.35, 36.56, and 39.15 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising 5-azacytidine and glycine having an XRPD pattern comprising peaks at approximately 13.87, 23.88, and 29.83 degrees 2θ. In certain embodiments, the solid form further comprises peaks at approximately 17.42, 22.62, and 35.34 degrees 2θ. In one embodiment, the solid form comprises peaks at approximately 11.96, 13.87, 14.81, 15.10, 17.42, 17.88, 18.93, 20.10, 20.65, 21.38, 21.60, 22.62, 23.88, 25.24, 26.26, 28.39, 28.60, 29.19, 29.83, 30.14 30.45, 31.34, 35.34, 36.35, 36.56, and 39.15 degrees 2θ.

In some embodiments, provided herein is a solid form comprising 5-azacytidine and glycine having an XRPD pattern comprising peaks at approximately 11.96, 23.88, and 29.83 degrees 2θ. In some embodiments, provided herein is a solid form comprising 5-azacytidine and glycine having an XRPD pattern comprising peaks at approximately 23.88, 28.39, and 29.83 degrees 2θ. In some embodiments, provided herein is a solid form comprising 5-azacytidine and gallic acid having an XRPD pattern comprising peaks at approximately 23.88, 29.83, and 35.34 degrees 2θ.

In some embodiments, provided herein is a solid form comprising 5-azacytidine and glycine, wherein the solid form is characterized by an XRPD diffraction pattern which matches the XRPD pattern presented in FIG. 2.

5.2.3 Cocrystal Comprising 5-Azacytidine and Glycolic Acid

Certain embodiments herein provide solid forms comprising 5-azacytidine and glycolic acid. In one embodiment, provided herein is a solid form comprising 5-azacytidine and glycolic acid that is substantially crystalline. In one embodiment, provided herein is a cocrystal comprising 5-azacytidine and glycolic acid. In one embodiment, provided herein is a solid form comprising a cocrystal comprising 5-azacytidine and glycolic acid. In one embodiment, provided herein is a solid form comprising (i) a cocrystal comprising 5-azacytidine and glycolic acid and (ii) an amorphous form of 5-azacytidine. In one embodiment, provided herein is a solid form comprising (i) a cocrystal comprising 5-azacytidine and glycolic acid and (ii) one or more additional crystal forms of 5-azacytidine. Provided herein are various embodiments, preparations, or modifications of a cocrystal comprising 5-azacytidine and glycolic acid.

In some embodiments, the cocrystal comprising 5-azacytidine and glycolic acid is obtained by mixing 5-azacytidine and glycolic acid in a solvent system. In some embodiments, the cocrystal is obtained by mixing 5-azacytidine and glycolic acid in a solvent system saturated with glycolic acid. In some embodiments, the cocrystal is obtained by mixing 5-azacytidine and glycolic acid in a solvent system saturated with glycolic acid, and subsequently stirring the mixture at room temperature for about 24 hours. In some embodiments, the cocrystal is obtained by mixing 5-azacytidine and glycolic acid in a solvent system saturated with glycolic acid, subsequently stirring the mixture at room temperature for about 24 hours, and isolating the solid by centrifugation. In some embodiments, the cocrystal is obtained by mixing approximately equal molar amount of 5-azacytidine and glycolic acid in a solvent system saturated with glycolic acid. In some embodiments, the solvent system is a mixed solvent of methanol and water with a volume ratio of methanol to water of about 1:3.

In some embodiments, the cocrystal comprising 5-azacytidine and glycolic acid is obtained by removing solvent from a solution containing 5-azacytidine and glycolic acid. In some embodiments, the cocrystal is obtained by removing solvent from a solution containing 5-azacytidine and glycolic acid on a rotary evaporator at about 80° C. In some embodiments, the cocrystal is obtained by removing solvent from a solution containing 5-azacytidine and glycolic acid, and subsequently storing the residue at about 75% relative humidity for 1 day. In some embodiments, the cocrystal is obtained by removing solvent from a solution containing 5-azacytidine and glycolic acid, and subsequently storing the residue at about 60° C. overnight. In some embodiments, the cocrystal is obtained by removing solvent from a solution containing approximately equal molar amount of 5-azacytidine and glycolic acid.

In some embodiments, provided herein is a cocrystal comprising 5-azacytidine and glycolic acid with a molar ratio of 5-azacytidine to glycolic acid of approximately 2:1 to 1:2. In some embodiments, the molar ratio of 5-azacytidine to glycolic acid is approximately 1:1.

A representative XRPD pattern of a solid form comprising 5-azacytidine and glycolic acid is provided in FIG. 3. In some embodiments, provided herein is a solid form comprising 5-azacytidine and glycolic acid characterized by one or more XRPD peaks (e.g., 1, 2, 3, 4, 5, 6, 7, 8, 9, 10, 11, 12, 13, 14, 15, 16, 17, 18, 19, 20, 21, 22, 23, 24, 25, or more peaks) selected from peaks located at the following or approximately the following positions: 13.69, 13.78, 16.81, 20.08, 20.96, 21.80, 21.91, 23.49, 25.11, 25.30, 25.41, 26.47, 30.39, 30.62, 31.44, 31.50, 31.99, 33.65, 33.82, 33.98, 34.19, 35.77, 35.92, 36.31, and 39.73 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by all of the peaks.

In some embodiments, provided herein is a solid form comprising 5-azacytidine and glycolic acid having an XRPD pattern comprising peaks at approximately 25.41, 30.62, and 35.77 degrees 2θ. In certain embodiments, the solid form further comprises peaks at approximately 21.91, 30.62, and 35.77 degrees 2θ. In one embodiment, the solid form comprises peaks at approximately 13.69, 13.78, 16.81, 20.08, 20.96, 21.80, 21.91, 23.49, 25.11, 25.30, 25.41, 26.47, 30.39, 30.62, 31.44, 31.50, 31.99, 33.65, 33.82, 33.98, 34.19, 35.77, 35.92, 36.31, and 39.73 degrees 2θ.

In some embodiments, provided herein is a solid form comprising 5-azacytidine and glycolic acid having an XRPD pattern comprising peaks at approximately 16.81, 30.62, and 35.77 degrees 2θ. In some embodiments, provided herein is a solid form comprising 5-azacytidine and glycolic acid having an XRPD pattern comprising peaks at approximately 20.08, 30.62, and 35.77 degrees 2θ. In some embodiments, provided herein is a solid form comprising 5-azacytidine and gallic acid having an XRPD pattern comprising peaks at approximately 30.62, 35.77 and 36.31 degrees 2θ.

In some embodiments, provided herein is a solid form comprising 5-azacytidine and glycolic acid, wherein the solid form is characterized by an XRPD diffraction pattern which matches the XRPD pattern presented in FIG. 3.

5.2.4 Cocrystal Comprising 5-Azacytidine and Malonic Acid

Certain embodiments herein provide solid forms comprising 5-azacytidine and malonic acid. In one embodiment, provided herein is a solid form comprising 5-azacytidine and malonic acid that is substantially crystalline. In one embodiment, provided herein is a cocrystal comprising 5-azacytidine and malonic acid. In one embodiment, provided herein is a solid form comprising a cocrystal comprising 5-azacytidine and malonic acid. In one embodiment, provided herein is a solid form comprising (i) a cocrystal comprising 5-azacytidine and malonic acid and (ii) an amorphous form of 5-azacytidine. In one embodiment, provided herein is a solid form comprising (i) a cocrystal comprising 5-azacytidine and malonic acid and (ii) one or more additional crystal forms of 5-azacytidine. Provided herein are various embodiments, preparations, or modifications of a cocrystal comprising 5-azacytidine and malonic acid.

In some embodiments, the cocrystal comprising 5-azacytidine and malonic acid is obtained by mixing 5-azacytidine and malonic acid in a solvent system. In some embodiments, the cocrystal is obtained by mixing 5-azacytidine and malonic acid in a solvent system saturated with malonic acid. In some embodiments, the cocrystal is obtained by mixing 5-azacytidine and malonic acid in a solvent system saturated with malonic acid, and subsequently stirring the mixture at room temperature for about 24 hours. In some embodiments, the cocrystal is obtained by mixing 5-azacytidine and malonic acid in a solvent system saturated with malonic acid, subsequently stirring the mixture at room temperature for about 24 hours, and isolating the solid by centrifugation. In some embodiments, the cocrystal is obtained by mixing approximately equal molar amount of 5-azacytidine and malonic acid in a solvent system saturated with malonic acid. In some embodiments, the solvent system is a mixed solvent of methanol and water with a volume ratio of methanol to water of about 1:3.

In some embodiments, the cocrystal comprising 5-azacytidine and malonic acid is obtained by removing solvent from a solution containing 5-azacytidine and malonic acid. In some embodiments, the cocrystal is obtained by removing solvent from a solution containing 5-azacytidine and malonic acid on a rotary evaporator at about 80° C. In some embodiments, the cocrystal is obtained by removing solvent from a solution containing 5-azacytidine and malonic acid, and subsequently storing the residue at about 75% relative humidity for 1 day. In some embodiments, the cocrystal is obtained by removing solvent from a solution containing 5-azacytidine and malonic acid, and subsequently storing the residue at about 60° C. overnight. In some embodiments, the cocrystal is obtained by removing solvent from a solution containing approximately equal molar amount of 5-azacytidine and malonic acid.

In some embodiments, provided herein is a cocrystal comprising 5-azacytidine and malonic acid with a molar ratio of 5-azacytidine to malonic acid of approximately 2:1 to 1:2. In some embodiments, the molar ratio of 5-azacytidine to malonic acid is approximately 1:1.

A representative XRPD pattern of a solid form comprising 5-azacytidine and malonic acid is provided in FIG. 4. In some embodiments, provided herein is a solid form comprising 5-azacytidine and malonic acid characterized by one or more XRPD peaks (e.g., 1, 2, 3, 4, 5, 6, 7, 8, 9, 10, 11, 12, 13, 14, 15, or more peaks) selected from peaks located at the following or approximately the following positions: 17.71, 18.79, 19.02, 23.17, 23.74, 24.86, 25.13, 26.72, 27.08, 33.09, 33.26, 33.66, 34.20, 35.82, and 38.12 degrees 2θ. In some embodiments, the solid form is characterized by 3 of the peaks. In some embodiments, the solid form is characterized by 5 of the peaks. In some embodiments, the solid form is characterized by 7 of the peaks. In some of the embodiments, the solid form is characterized by 10 of the peaks. In some embodiments, the solid form is characterized by all of the peaks.

In some embodiments, provided herein is a solid form comprising 5-azacytidine and malonic acid having an XRPD pattern comprising peaks at approximately 17.71, 33.09, and 38.12 degrees 2θ. In certain embodiments, the solid form further comprises peaks at approximately 18.79, 24.86, and 25.13 degrees 2θ. In one embodiment, the solid form comprises peaks at approximately 17.71, 18.79, 19.02, 23.17, 23.74, 24.86, 25.13, 26.72, 27.08, 33.09, 33.26, 33.66, 34.20, 35.82, and 38.12 degrees 2θ.

In some embodiments, provided herein is a solid form comprising 5-azacytidine and malonic acid having an XRPD pattern comprising peaks at approximately 18.79, 33.09, and 38.12 degrees 2θ. In some embodiments, provided herein is a solid form comprising 5-azacytidine and malonic acid having an XRPD pattern comprising peaks at approximately 23.74, 33.09, and 38.12 degrees 2θ. In some embodiments, provided herein is a solid form comprising 5-azacytidine and gallic acid having an XRPD pattern comprising peaks at approximately 25.13, 33.09, and 38.12 degrees 2θ.

In some embodiments, provided herein is a solid form comprising 5-azacytidine and malonic acid, wherein the solid form is characterized by an XRPD diffraction pattern which matches the XRPD pattern presented in FIG. 4.

5.2.5 Cocrystal Comprising 5-Azacytidine and Propyl Gallate

Certain embodiments herein provide solid forms comprising 5-azacytidine and propyl gallate. In one embodiment, provided herein is a solid form comprising 5-azacytidine and propyl gallate that is substantially crystalline. In one embodiment, provided herein is a cocrystal comprising 5-azacytidine and propyl gallate. In one embodiment, provided herein is a solid form comprising a cocrystal comprising 5-azacytidine and propyl gallate. In one embodiment, provided herein is a solid form comprising (i) a cocrystal comprising 5-azacytidine and propyl gallate and (ii) an amorphous form of 5-azacytidine. In one embodiment, provided herein is a solid form comprising (i) a cocrystal comprising 5-azacytidine and propyl gallate and (ii) one or more additional crystal forms of 5-azacytidine. Provided herein are various embodiments, preparations, or modifications of a cocrystal comprising 5-azacytidine and propyl gallate.

In some embodiments, the cocrystal comprising 5-azacytidine and propyl gallate is obtained by mixing 5-azacytidine and propyl gallate in a solvent system. In some embodiments, the cocrystal is obtained by mixing 5-azacytidine and propyl gallate in a solvent system saturated with propyl gallate. In some embodiments, the cocrystal is obtained by mixing 5-azacytidine and propyl gallate in a solvent system saturated with propyl gallate, and subsequently stirring the mixture at room temperature for about 24 hours. In some embodiments, the cocrystal is obtained by mixing 5-azacytidine and propyl gallate in a solvent system saturated with propyl gallate, subsequently stirring the mixture at room temperature for about 24 hours, and isolating the solid by centrifugation. In some embodiments, the cocrystal is obtained by mixing approximately equal molar amount of 5-azacytidine and propyl gallate in a solvent system saturated with propyl gallate. In some embodiments, the solvent system is a mixed solvent of methanol and water with a volume ratio of methanol to water of about 1:2.

In some embodiments, provided herein is a cocrystal comprising 5-azacytidine and propyl gallate with a molar ratio of 5-azacytidine to propyl gallate of approximately 2:1 to 1:2. In some embodiments, the molar ratio of 5-azacytidine to propyl gallate is approximately 1:1.

A representative XRPD pattern of a solid form comprising 5-azacytidine and propyl gallate is provided in FIG. 5. In some embodiments, provided herein is a solid form comprising 5-azacytidine and propyl gallate characterized by one or more XRPD peaks (e.g., 1, 2, 3, 4, 5, 6, 7, 8, 9, 10, 11, 12, 13, 14, 15, 16, 17, 18, 19 or more peaks) selected from peaks located at the following or approximately the following positions: 4.68, 9.07, 11.41, 12.18, 12.54, 13.05, 14.39, 14.79, 16.47, 19.10, 20.18, 23.05, 23.91, 25.83, 26.36, 27.03, 27.13, 29.32, and 32.09 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by all of the peaks.

In some embodiments, provided herein is a solid form comprising 5-azacytidine and propyl gallate having an XRPD pattern comprising peaks at approximately 11.41, 26.36, and 27.13 degrees 2θ. In certain embodiments, the solid form further comprises peaks at approximately 14.79 and 20.18 degrees 2θ. In certain embodiments, the solid form further comprises peaks at approximately 16.47 and 23.05 degrees 2θ. In one embodiment, the solid form comprises peaks at approximately 4.68, 9.07, 11.41, 12.18, 12.54, 13.05, 14.39, 14.79, 16.47, 19.10, 20.18, 23.05, 23.91, 25.83, 26.36, 27.03, 27.13, 29.32, and 32.09 degrees 2θ.

In some embodiments, provided herein is a solid form comprising 5-azacytidine and propyl gallate having an XRPD pattern comprising peaks at 14.79, 26.36, and 27.13 degrees 2θ. In some embodiments, provided herein is a solid form comprising 5-azacytidine and propyl gallate having an XRPD pattern comprising peaks at approximately 16.47, 26.36, and 27.13 degrees 2θ. In some embodiments, provided herein is a solid form comprising 5-azacytidine and propyl gallate having an XRPD pattern comprising peaks at approximately 20.18, 26.36, and 27.13 degrees 2θ. In some embodiments, provided herein is a solid form comprising 5-azacytidine and propyl gallate having an XRPD pattern comprising peaks at approximately 23.05 degrees 2θ.

In some embodiments, provided herein is a solid form comprising 5-azacytidine and propyl gallate, wherein the solid form is characterized by an XRPD diffraction pattern which matches the XRPD pattern presented in FIG. 5.

5.2.6 Cocrystal Comprising 5-Azacytidine and Cyclamic Acid

Certain embodiments herein provide solid forms comprising 5-azacytidine and cyclamic acid. In one embodiment, provided herein is a solid form comprising 5-azacytidine and cyclamic acid that is substantially crystalline. In one embodiment, provided herein is a cocrystal comprising 5-azacytidine and cyclamic acid. In one embodiment, provided herein is a solid form comprising a cocrystal comprising 5-azacytidine and cyclamic acid. In one embodiment, provided herein is a solid form comprising (i) a cocrystal comprising 5-azacytidine and cyclamic acid and (ii) an amorphous form of 5-azacytidine. In one embodiment, provided herein is a solid form comprising (i) a cocrystal comprising 5-azacytidine and cyclamic acid and (ii) one or more additional crystal forms of 5-azacytidine. Provided herein are various embodiments, preparations, or modifications of a cocrystal comprising 5-azacytidine and cyclamic acid.

In some embodiments, the cocrystal comprising 5-azacytidine and cyclamic acid is obtained by mixing 5-azacytidine and cyclamic acid in a solvent system. In some embodiments, the cocrystal is obtained by mixing 5-azacytidine and cyclamic acid in a solvent system saturated with cyclamic acid. In some embodiments, the cocrystal is obtained by mixing 5-azacytidine and cyclamic acid in a solvent system saturated with cyclamic acid, and subsequently stirring the mixture at room temperature for about 24 hours. In some embodiments, the cocrystal is obtained by mixing 5-azacytidine and cyclamic acid in a solvent system saturated with cyclamic acid, subsequently stirring the mixture at room temperature for about 24 hours, and isolating the solid by centrifugation. In some embodiments, the cocrystal is obtained by mixing approximately equal molar amount of 5-azacytidine and cyclamic acid in a solvent system saturated with cyclamic acid. In some embodiments, the solvent system is a mixed solvent of methanol and water with a volume ratio of methanol to water of about 1:3.

In some embodiments, provided herein is a cocrystal comprising 5-azacytidine and cyclamic acid with a molar ratio of 5-azacytidine to cyclamic acid of approximately 2:1 to 1:2. In some embodiments, the molar ratio of 5-azacytidine to cyclamic acid is approximately 1:1.

A representative XRPD pattern of a solid form comprising 5-azacytidine and cyclamic acid is provided in FIG. 6. In some embodiments, provided herein is a solid form comprising 5-azacytidine and cyclamic acid characterized by one or more XRPD peaks (e.g., 1, 2, 3, 4, 5, 6, 7, 8, 9, 10, 11, 12, 13, 14, 15, 16, 17, 18, 19, or more peaks) selected from peaks located at the following or approximately the following positions: 3.04, 3.34, 4.04, 6.03, 7.90, 9.02, 12.24, 13.07, 14.07, 14.68, 15.41, 16.56, 18.14, 19.08, 20.27, 21.19, 21.68, 23.07, and 25.05 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising 5-azacytidine and cyclamic acid having an XRPD pattern comprising peaks at approximately 3.34, 6.03, and 14.68 degrees 2θ. In certain embodiments, the solid form further comprises peaks at approximately 7.90 and 14.07 degrees 2θ. In certain embodiments, the solid form further comprises peaks at approximately 3.04 and 23.07 degrees 2θ. In one embodiment, the solid form comprises peaks at approximately 3.04, 3.34, 4.04, 6.03, 7.90, 9.02, 12.24, 13.07, 14.07, 14.68, 15.41, 16.56, 18.14, 19.08, 20.27, 21.19, 21.68, 23.07, and 25.05 degrees 2θ.

In some embodiments, provided herein is a solid form comprising 5-azacytidine and cyclamic acid having an XRPD pattern comprising peaks at approximately 3.34, 7.90, and 14.68 degrees 2θ. In some embodiments, provided herein is a solid form comprising 5-azacytidine and cyclamic acid having an XRPD pattern comprising peaks at approximately 3.34, 14.07, and 14.68 degrees 2θ. In some embodiments, provided herein is a solid form comprising 5-azacytidine and cyclamic acid having an XRPD pattern comprising peaks at approximately 3.04, 3.34, and 14.68 degrees 2θ. In some embodiments, provided herein is a solid form comprising 5-azacytidine and cyclamic acid having an XRPD pattern comprising peaks at approximately 3.34, 14.68, and 23.07 degrees 2θ.

In some embodiments, provided herein is a solid form comprising 5-azacytidine and cyclamic acid, wherein the solid form is characterized by an XRPD diffraction pattern which matches the XRPD pattern presented in FIG. 6.

5.2.7 Cocrystal Comprising 5-Azacytidine and Nicotinamide

Certain embodiments herein provide solid forms comprising 5-azacytidine and nicotinamide. In one embodiment, provided herein is a solid form comprising 5-azacytidine and nicotinamide that is substantially crystalline. In one embodiment, provided herein is a cocrystal comprising 5-azacytidine and nicotinamide. In one embodiment, provided herein is a solid form comprising a cocrystal comprising 5-azacytidine and nicotinamide. In one embodiment, provided herein is a solid form comprising (i) a cocrystal comprising 5-azacytidine and nicotinamide and (ii) an amorphous form of 5-azacytidine. In one embodiment, provided herein is a solid form comprising (i) a cocrystal comprising 5-azacytidine and nicotinamide and (ii) one or more additional crystal forms of 5-azacytidine. Provided herein are various embodiments, preparations, or modifications of a cocrystal comprising 5-azacytidine and nicotinamide.

In some embodiments, the cocrystal comprising 5-azacytidine and nicotinamide is obtained by grinding 5-azacytidine and nicotinamide together in the presence of a minor quantity of a solvent system. In some embodiments, the cocrystal comprising 5-azacytidine and nicotinamide is obtained by grinding approximately equal molar amount of 5-azacytidine and nicotinamide together in the presence of a minor quantity of a solvent system. In some embodiments, the solvent system is a mixed solvent of methanol and water with a volume ratio of methanol to water of about 2:1.

In some embodiments, provided herein is a cocrystal comprising 5-azacytidine and nicotinamide with a molar ratio of 5-azacytidine to nicotinamide of approximately 2:1 to 1:2. In some embodiments, the molar ratio of 5-azacytidine to nicotinamide is approximately 1:1.

A representative XRPD pattern of a solid form comprising 5-azacytidine and nicotinamide is provided in FIG. 7. In some embodiments, provided herein is a solid form comprising 5-azacytidine and nicotinamide characterized by one or more XRPD peaks (e.g., 1, 2, 3, 4, 5, 6, 7, 8, 9, 10, 11, 12, 13, 14, 15, 16, 17, 18, 19, 20, 21, 22 or more peaks) selected from peaks located at the following or approximately the following positions: 11.97, 13.34, 14.22, 17.35, 20.64, 20.93, 21.80, 22.31, 22.77, 23.35, 23.52, 23.80, 24.07, 24.97, 25.91, 27.00, 28.62, 28.84, 29.27, 30.60, 30.82, and 38.38 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising 5-azacytidine and nicotinamide having an XRPD pattern comprising peaks at approximately 17.35, 24.07, and 28.62 degrees 2θ. In certain embodiments, the solid form further comprises peaks at approximately 14.22 and 23.35 degrees 2θ. In certain embodiments, the solid form further comprises peaks at approximately 22.31 and 30.60 degrees 2θ. In one embodiment, the solid form comprises peaks at approximately 11.97, 13.34, 14.22, 17.35, 20.64, 20.93, 21.80, 22.31, 22.77, 23.35, 23.52, 23.80, 24.07, 24.97, 25.91, 27.00, 28.62, 28.84, 29.27, 30.60, 30.82, and 38.38 degrees 2θ.

In some embodiments, provided herein is a solid form comprising 5-azacytidine and nicotinamide having an XRPD pattern comprising peaks at approximately 14.22, 24.07, and 28.62 degrees 2θ. In some embodiments, provided herein is a solid form comprising 5-azacytidine and nicotinamide having an XRPD pattern comprising peaks at approximately 22.31, 24.07, and 28.62 degrees 2θ. In some embodiments, provided herein is a solid form comprising 5-azacytidine and nicotinamide having an XRPD pattern comprising peaks at approximately 23.35, 24.07, and 28.62 degrees 2θ. In some embodiments, provided herein is a solid form comprising 5-azacytidine and nicotinamide having an XRPD pattern comprising peaks at approximately 24.07, 28.62 and 3060 degrees 2θ.

In some embodiments, provided herein is a solid form comprising 5-azacytidine and nicotinamide, wherein the solid form is characterized by an XRPD diffraction pattern which matches the XRPD pattern presented in FIG. 7.

5.2.8 Cocrystal Comprising 5-Azacytidine and Ketoglutaric Acid

Certain embodiments herein provide solid forms comprising 5-azacytidine and ketoglutaric acid. In one embodiment, provided herein is a solid form comprising 5-azacytidine and ketoglutaric acid that is substantially crystalline. In one embodiment, provided herein is a cocrystal comprising 5-azacytidine and ketoglutaric acid. In one embodiment, provided herein is a solid form comprising a cocrystal comprising 5-azacytidine and ketoglutaric acid. In one embodiment, provided herein is a solid form comprising (i) a cocrystal comprising 5-azacytidine and ketoglutaric acid and (ii) an amorphous form of 5-azacytidine. In one embodiment, provided herein is a solid form comprising (i) a cocrystal comprising 5-azacytidine and ketoglutaric acid and (ii) one or more additional crystal forms of 5-azacytidine. Provided herein are various embodiments, preparations, or modifications of a cocrystal comprising 5-azacytidine and ketoglutaric acid.

In some embodiments, the cocrystal comprising 5-azacytidine and ketoglutaric acid is obtained by removing solvent from a solution containing 5-azacytidine and ketoglutaric acid. In some embodiments, the cocrystal is obtained by removing solvent from a solution containing 5-azacytidine and ketoglutaric acid on a rotary evaporator at about 80° C. In some embodiments, the cocrystal is obtained by removing solvent from a solution containing 5-azacytidine and ketoglutaric acid, and subsequently storing the residue at about 75% relative humidity for 1 day. In some embodiments, the cocrystal is obtained by removing solvent from a solution containing 5-azacytidine and ketoglutaric acid, and subsequently storing the residue at about 60° C. overnight. In some embodiments, the cocrystal is obtained by removing solvent from a solution containing approximately equal molar amount of 5-azacytidine and ketoglutaric acid.

In some embodiments, provided herein is a cocrystal comprising 5-azacytidine and ketoglutaric acid with a molar ratio of 5-azacytidine to ketoglutaric acid of approximately 2:1 to 1:2. In some embodiments, the molar ratio of 5-azacytidine to ketoglutaric acid is approximately 1:1.

A representative XRPD pattern of a solid form comprising 5-azacytidine and ketoglutaric acid is provided in FIG. 8. In some embodiments, provided herein is a solid form comprising 5-azacytidine and ketoglutaric acid characterized by one or more XRPD peaks (e.g., 1, 2, 3, 4, 5, 6, 7, 8, 9, 10, 11, 12, 13, 14, 15, 16, 17, 18 19, 20, 21, 22, 23, 24, 24, 25, 26, 27, 28, 29, 30, 31, 32, 33, 34, 35, 36 or more peaks) selected from peaks located at the following or approximately the following positions: 6.60, 7.76, 9.68, 12.20, 12.98, 13.26, 14.13, 15.60, 16.43, 17.34, 18.07, 18.97, 19.44, 20.32, 21.60, 22.26, 23.03, 23.58, 23.75, 24.44, 24.90, 25.16, 26.87, 28.07, 28.36, 28.70, 29.24, 29.52, 30.42, 32.89, 33.48, 34.00, 34.54, 35.08, 35.42, and 36.49 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising 5-azacytidine and ketoglutaric acid having an XRPD pattern comprising peaks at approximately 6.60, 12.20, and 14.13 degrees 2θ. In certain embodiments, the solid form further comprises peaks at approximately 10.60 and 12.34 degrees 2θ. In certain embodiments, the solid form further comprises peaks at approximately 20.32 and 23.58 degrees 2θ. In one embodiment, the solid form comprises peaks at approximately 6.60, 7.76, 9.68, 12.20, 12.98, 13.26, 14.13, 15.60, 16.43, 17.34, 18.07, 18.97, 19.44, 20.32, 21.60, 22.26, 23.03, 23.58, 23.75, 24.44, 24.90, 25.16, 26.87, 28.07, 28.36, 28.70, 29.24, 29.52, 30.42, 32.89, 33.48, 34.00, 34.54, 35.08, 35.42, and 36.49 degrees 2θ.

In some embodiments, provided herein is a solid form comprising 5-azacytidine and ketoglutaric acid having an XRPD pattern comprising peaks at approximately 10.60, 13.46, and 20.77, degrees 2θ. In some embodiments, provided herein is a solid form comprising 5-azacytidine and ketoglutaric acid having an XRPD pattern comprising peaks at approximately 6.60, 12.20, and 14.13, degrees 2θ. In some embodiments, provided herein is a solid form comprising 5-azacytidine and ketoglutaric acid having an XRPD pattern comprising peaks at approximately 14.23, 20.32 and 23.58, degrees 2θ. In some embodiments, provided herein is a solid form comprising 5-azacytidine and ketoglutaric acid having an XRPD pattern comprising peaks at approximately 12.34, 25.16, and 30.42 degrees 2θ.

In some embodiments, provided herein is a solid form comprising 5-azacytidine and ketoglutaric acid, wherein the solid form is characterized by an XRPD diffraction pattern which matches the XRPD pattern presented in FIG. 8.

5.2.9 Cocrystal Comprising 5-azacytidine and Maleic Acid

Certain embodiments herein provide solid forms comprising 5-azacytidine and maleic acid. In one embodiment, provided herein is a solid form comprising 5-azacytidine and maleic acid that is substantially crystalline. In one embodiment, provided herein is a cocrystal comprising 5-azacytidine and maleic acid. In one embodiment, provided herein is a solid form comprising a cocrystal comprising 5-azacytidine and maleic acid. In one embodiment, provided herein is a solid form comprising (i) a cocrystal comprising 5-azacytidine and maleic acid and (ii) an amorphous form of 5-azacytidine. In one embodiment, provided herein is a solid form comprising (i) a cocrystal comprising 5-azacytidine and maleic acid and (ii) one or more additional crystal forms of 5-azacytidine. Provided herein are various embodiments, preparations, or modifications of a cocrystal comprising 5-azacytidine and maleic acid.

In some embodiments, the cocrystal comprising 5-azacytidine and maleic acid is obtained by removing solvent from a solution containing 5-azacytidine and maleic acid. In some embodiments, the cocrystal is obtained by removing solvent from a solution containing 5-azacytidine and maleic acid on a rotary evaporator at about 80° C. In some embodiments, the cocrystal is obtained by removing solvent from a solution containing 5-azacytidine and maleic acid, and subsequently storing the residue at about 75% relative humidity for 1 day. In some embodiments, the cocrystal is obtained by removing solvent from a solution containing 5-azacytidine and maleic acid, and subsequently storing the residue at about 60° C. overnight. In some embodiments, the cocrystal is obtained by removing solvent from a solution containing approximately equal molar amount of 5-azacytidine and maleic acid.

In some embodiments, provided herein is a cocrystal comprising 5-azacytidine and maleic acid with a molar ratio of 5-azacytidine to maleic acid of approximately 2:1 to 1:2. In some embodiments, the molar ratio of 5-azacytidine to maleic acid is approximately 1:1.

A representative XRPD pattern of a solid form comprising 5-azacytidine and maleic acid is provided in FIG. 9. In some embodiments, provided herein is a solid form comprising 5-azacytidine and maleic acid characterized by one or more XRPD peaks (e.g., 1, 2, 3, 4, 5, 6, 7, 8, 9, 10, 11, 12, or more peaks) selected from peaks located at the following or approximately the following positions: 8.20, 12.74, 13.77, 15.63, 20.33, 23.13, 23.46, 24.20, 28.48, 28.93, 29.61, and 30.59 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by all of the peaks.

In some embodiments, provided herein is a solid form comprising 5-azacytidine and maleic acid having an XRPD pattern comprising peaks at approximately 13.77, 23.13, and 28.48 degrees 2θ. In certain embodiments, the solid form further comprises peaks at approximately 8.20, 20.33, and 29.61 degrees 2θ. In one embodiment, the solid form comprises peaks at approximately 8.20, 12.74, 13.77, 15.63, 20.33, 23.13, 23.46, 24.20, 28.48, 28.93, 29.61, and 30.59 degrees 2θ.

In some embodiments, provided herein is a solid form comprising 5-azacytidine and maleic acid having an XRPD pattern comprising peaks at approximately 8.20, 23.13, and 28.48 degrees 2θ. In some embodiments, provided herein is a solid form comprising 5-azacytidine and maleic acid having an XRPD pattern comprising peaks at approximately 20.33, 23.13, and 28.48 degrees 2θ. In some embodiments, provided herein is a solid form comprising 5-azacytidine and maleic acid having an XRPD pattern comprising peaks at approximately 23.13, 28.48, and 29.61 degrees 2θ.

In some embodiments, provided herein is a solid form comprising 5-azacytidine and maleic acid, wherein the solid form is characterized by an XRPD diffraction pattern which matches the XRPD pattern presented in FIG. 9.

5.2.10 Cocrystal Comprising 5-Azacytidine and Zinc Chloride

Certain embodiments herein provide solid forms comprising 5-azacytidine and zinc chloride. In one embodiment, provided herein is a solid form comprising 5-azacytidine and zinc chloride that is substantially crystalline. In one embodiment, provided herein is a cocrystal comprising 5-azacytidine and zinc chloride. In one embodiment, provided herein is a solid form comprising a cocrystal comprising 5-azacytidine and zinc chloride. In one embodiment, provided herein is a solid form comprising (i) a cocrystal comprising 5-azacytidine and zinc chloride and (ii) an amorphous form of 5-azacytidine. In one embodiment, provided herein is a solid form comprising (i) a cocrystal comprising 5-azacytidine and zinc chloride and (ii) one or more additional crystal forms of 5-azacytidine. Provided herein are various embodiments, preparations, or modifications of a cocrystal comprising 5-azacytidine and zinc chloride.

In some embodiments, the cocrystal comprising 5-azacytidine and zinc chloride is obtained by removing solvent from a solution containing 5-azacytidine and zinc chloride. In some embodiments, the cocrystal is obtained by removing solvent from a solution containing 5-azacytidine and zinc chloride on a rotary evaporator at about 80° C. In some embodiments, the cocrystal is obtained by removing solvent from a solution containing 5-azacytidine and zinc chloride, and subsequently storing the residue at about 75% relative humidity for 1 day. In some embodiments, the cocrystal is obtained by removing solvent from a solution containing 5-azacytidine and zinc chloride, and subsequently storing the residue at about 60° C. overnight. In some embodiments, the cocrystal is obtained by removing solvent from a solution containing approximately equal molar amount of 5-azacytidine and zinc chloride.

In some embodiments, provided herein is a cocrystal comprising 5-azacytidine and zinc chloride with a molar ratio of 5-azacytidine to zinc chloride of approximately 2:1 to 1:2. In some embodiments, the molar ratio of 5-azacytidine to zinc chloride is approximately 1:1.

A representative XRPD pattern of a solid form comprising 5-azacytidine and zinc chloride is provided in FIG. 10. In some embodiments, provided herein is a solid form comprising 5-azacytidine and zinc chloride characterized by one or more XRPD peaks (e.g., 1, 2, 3, 4, 5, 6, 7, 8, 9, 10, 11, 12, 13, 14, 15, 16, 17, 18 or more peaks) selected from peaks located at the following or approximately the following positions: 4.24, 7.38, 12.70, 13.38, 17.09, 17.81, 20.16, 21.13, 21.84, 22.98, 24.41, 25.07, 26.01, 27.58, 28.93, 29.65, 31.53, and 39.41 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising 5-azacytidine and zinc chloride having an XRPD pattern comprising peaks at approximately 13.38, 17.09, and 26.01 degrees 2θ. In certain embodiments, the solid form further comprises peaks at approximately 7.38 and 12.70 degrees 2θ. In certain embodiments, the solid form further comprises peaks at approximately 28.93 and 31.53 degrees 2θ. In one embodiment, the solid form comprises peaks at approximately 4.24, 7.38, 12.70, 13.38, 17.09, 17.81, 20.16, 21.13, 21.84, 22.98, 24.41, 25.07, 26.01, 27.58, 28.93, 29.65, 31.53, and 39.41 degrees 2θ.

In some embodiments, provided herein is a solid form comprising 5-azacytidine and zinc chloride having an XRPD pattern comprising peaks at approximately 7.38, 17.09, and 26.01 degrees 2θ. In some embodiments, provided herein is a solid form comprising 5-azacytidine and zinc chloride having an XRPD pattern comprising peaks at approximately 12.70, 17.09, and 26.01 degrees 2θ. In some embodiments, provided herein is a solid form comprising 5-azacytidine and zinc chloride having an XRPD pattern comprising peaks at approximately 17.09, 26.01, and 28.93 degrees 2θ. In some embodiments, provided herein is a solid form comprising 5-azacytidine and zinc chloride having an XRPD pattern comprising peaks at approximately 17.09, 26.01, 31.53 degrees 2θ.

In some embodiments, provided herein is a solid form comprising 5-azacytidine and zinc chloride, wherein the solid form is characterized by an XRPD diffraction pattern which matches the XRPD pattern presented in FIG. 10.

5.2.11 Cocrystal Comprising 5-Azacytidine and Gallic Acid

Certain embodiments herein provide solid forms comprising 5-azacytidine and gallic acid. In one embodiment, provided herein is a solid form comprising 5-azacytidine and gallic acid that is substantially crystalline. In one embodiment, provided herein is a cocrystal comprising 5-azacytidine and gallic acid. In one embodiment, provided herein is a solid form comprising a cocrystal comprising 5-azacytidine and gallic acid. In one embodiment, provided herein is a solid form comprising (i) a cocrystal comprising 5-azacytidine and gallic acid and (ii) an amorphous form of 5-azacytidine. In one embodiment, provided herein is a solid form comprising (i) a cocrystal comprising 5-azacytidine and gallic acid and (ii) one or more additional crystal forms of 5-azacytidine. Provided herein are various embodiments, preparations, or modifications of a cocrystal comprising 5-azacytidine and gallic acid.

In some embodiments, the cocrystal comprising 5-azacytidine and gallic acid is obtained by removing solvent from a solution containing 5-azacytidine and gallic acid. In some embodiments, the cocrystal is obtained by removing solvent from a solution containing 5-azacytidine and gallic acid on a rotary evaporator at about 80° C. In some embodiments, the cocrystal is obtained by removing solvent from a solution containing 5-azacytidine and gallic acid, and subsequently storing the residue at about 75% relative humidity for 1 day. In some embodiments, the cocrystal is obtained by removing solvent from a solution containing 5-azacytidine and gallic acid, and subsequently storing the residue at about 60° C. overnight. In some embodiments, the cocrystal is obtained by removing solvent from a solution containing approximately equal molar amount of 5-azacytidine and gallic acid.

In some embodiments, provided herein is a cocrystal comprising 5-azacytidine and gallic acid with a molar ratio of 5-azacytidine to gallic acid of approximately 2:1 to 1:2. In some embodiments, the molar ratio of 5-azacytidine to gallic acid is approximately 1:1.

A representative XRPD pattern of a solid form comprising 5-azacytidine and gallic acid is provided in FIG. 11. In some embodiments, provided herein is a solid form comprising 5-azacytidine and gallic acid characterized by one or more XRPD peaks (e.g., 1, 2, 3, 4, 5, 6, 7, 8, 9, 10, 11, 12, 13, 14, 15, 16, 17, 18, 19, 20, 21, 22, 23, 24 or more peaks) selected from peaks located at the following or approximately the following positions: 8.04, 10.26, 11.73, 11.87, 16.15, 18.51, 18.94, 19.11, 19.59, 20.38, 20.62, 21.83, 24.96, 25.34, 26.84, 27.36, 27.67, 27.97, 28.43, 30.23, 31.65, 32.60, 37.38, and 38.44 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising 5-azacytidine and gallic acid having an XRPD pattern comprising peaks at approximately 16.15, 20.62, and 25.34 degrees 2θ. In certain embodiments, the solid form further comprises peaks at approximately 10.26 and 11.87 degrees 2θ. In certain embodiments, the solid form further comprises peaks at approximately 27.97 and 37.38 degrees 2θ. In one embodiment, the solid form comprises peaks at approximately 8.04, 10.26, 11.73, 11.87, 16.15, 18.51, 18.94, 19.11, 19.59, 20.38, 20.62, 21.83, 24.96, 25.34, 26.84, 27.36, 27.67, 27.97, 28.43, 30.23, 31.65, 32.60, 37.38, and 38.44 degrees 2θ.

In some embodiments, provided herein is a solid form comprising 5-azacytidine and gallic acid having an XRPD pattern comprising peaks at approximately 10.26, 20.62, and 25.34 degrees 2θ. In some embodiments, provided herein is a solid form comprising 5-azacytidine and gallic acid having an XRPD pattern comprising peaks at approximately 11.87, 20.62, and 25.34 degrees 2θ. In some embodiments, provided herein is a solid form comprising 5-azacytidine and gallic acid having an XRPD pattern comprising peaks at approximately 20.62, 25.34, and 27.97 degrees 2θ. In some embodiments, provided herein is a solid form comprising 5-azacytidine and gallic acid having an XRPD pattern comprising peaks at approximately 20.62, 25.34, and 37.38 degrees 2θ.

In some embodiments, provided herein is a solid form comprising 5-azacytidine and gallic acid, wherein the solid form is characterized by an XRPD diffraction pattern which matches the XRPD pattern presented in FIG. 11.

5.3 Methods of Treatment, Prevention and Management

In one embodiment, provided herein is a method of using the pharmaceutical composition provided herein to treat, prevent, or manage a disease or disorder, including cancer, disorders related to abnormal cell proliferation, and hematologic disorders (e.g., MDS). In certain embodiments, provided herein is a method of using the pharmaceutical composition provided herein to treat one or more symptoms of a disease or disorder, including cancer, disorders related to abnormal cell proliferation, and hematologic disorders (e.g., MDS). In one embodiment, the pharmaceutical composition provided herein is prepared for use to treat, prevent, or manage a disease or disorder, including cancer, disorders related to abnormal cell proliferation, and hematologic disorders (e.g., MDS).

Certain embodiments herein provide methods of using the pharmaceutical compositions provided herein to treat diseases or disorders including, e.g., cancer, disorders related to abnormal cell proliferation, hematologic disorders, or immune disorders, among others. In certain embodiments, the pharmaceutical compositions of cytidine analogs are parenterally administered to subjects in need thereof to treat a cancer or a hematological disorder, such as, for example, MDS, AML, ALL, CML, NHL, leukemia, or lymphoma; or a solid tumor, such as, for example, sarcoma, carcinoma, melanoma, or cancer of the colon, breast, ovary, gastrointestinal system, kidney, lung (e.g., non-small-cell lung cancer and small-cell lung cancer), testicle, prostate, pancreas, lymphatic system, or bone. In certain embodiments, the pharmaceutical compositions of cytidine analogs are parenterally administered to subjects in need thereof to treat an immune disorder. In certain embodiments, the pharmaceutical compositions provided herein are co-administered with one or more therapeutic agents to provide a synergistic therapeutic effect in subjects in need thereof. In certain embodiments, the pharmaceutical compositions provided herein are co-administered with one or more therapeutic agents to provide a resensitization effect in subjects in need thereof. The co-administered agents may be a cancer therapeutic agent, as described herein. In certain embodiments, the co-administered agent(s) may be dosed, e.g., orally or by injection.

Specific embodiments herein provide, inter alia, methods for treating a subject having a disease associated with abnormal cell proliferation (e.g., MDS), comprising parenterally administering to the subject a pharmaceutical composition comprising a therapeutically effective amount of 5-azacytidine. Specific embodiments herein provide, inter alia, methods for treating a subject having a disease associated with abnormal cell proliferation (e.g., MDS), comprising parenterally administering to the subject a pharmaceutical composition comprising a therapeutically effective amount of decitabine. Further embodiments herein provide the aforementioned methods, in which: the composition accurately delivers an intended dose to the subject; the disease is myelodysplastic syndrome; the disease is acute myelogenous leukemia; the method further comprises co-administering to the subject in need thereof an additional therapeutic agent selected from any additional therapeutic agent disclosed herein; the composition is a liquid formulation prepared from cold sterile water (e.g., at a temperature of about 0° C., about 1° C., about 2° C., about 3° C., about 4° C., about 5° C., about 6° C., or about 8° C.); the composition is a liquid formulation prepared from cold sterile water, stored at a temperature of below about 8° C., below about 5° C., below about 2° C., about 0° C., about −10° C., or about −20° C., and warmed to about room temperature prior to parenteral administration; the composition is a single unit dosage form; the composition is a pre-packaged lyophilized powder in a vial; the composition is a liquid formulation (e.g., a suspension or a solution) in a vial, syringe, or I.V. bag; the composition is a solution for intravenous administration; the composition further comprises an excipient selected from any excipient disclosed herein; the amount of 5-azacytidine (or decitabine) is about 25 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg; and/or the amount of 5-azacytidine (or decitabine) is at least about 25 mg, at least about 50 mg; at least about 75 mg, at least about 100 mg, or at least about 125 mg.

Specific embodiments herein provide, inter alia, pharmaceutical compositions comprising a therapeutically effective amount of 5-azacytidine, for treating a disease or disorder associated with abnormal cell proliferation (e.g., MDS), wherein the compositions are prepared for parenteral administration. Specific embodiments herein provide, inter alia, pharmaceutical compositions comprising a therapeutically effective amount of decitabine, for treating a disease or disorder associated with abnormal cell proliferation (e.g., MDS), wherein the compositions are prepared for parenteral administration. Further embodiments herein provide the aforementioned compositions, in which: the composition accurately delivers an intended dose to the subject; the disease is myelodysplastic syndrome; the disease is acute myelogenous leukemia; the composition is a liquid formulation prepared from cold sterile water (e.g., at a temperature of about 0° C., about 1° C., about 2° C., about 3° C., about 4° C., about 5° C., about 6° C., or about 8° C.); the composition is a liquid formulation prepared from cold sterile water, stored at a temperature of below about 8° C., below about 5° C., below about 2° C., about 0° C., about −10° C., or about −20° C., and warmed to about room temperature prior to parenteral administration; the composition is a single unit dosage form; the composition is a pre-packaged lyophilized powder in a vial; the composition is a liquid formulation (e.g., a suspension or a solution) in a vial, syringe, or I.V. bag; the composition is a solution for intravenous administration; the composition further comprises an excipient selected from any excipient disclosed herein; the amount of 5-azacytidine (or decitabine) is about 25 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg; the amount of 5-azacytidine (or decitabine) is at least about 25 mg, at least about 50 mg; at least about 75 mg, at least about 100 mg, or at least about 125 mg; the composition is prepared to achieve a daily dose of about 30 mg/m$^2$ following parenteral administration; the composition is prepared to achieve a daily dose of about 40 mg/m$^2$ following parenteral administration; the composition is prepared to achieve a daily dose of about 50 mg/m$^2$ following parenteral administration; the composition is prepared to achieve a daily dose of about 75 mg/m$^2$ following parenteral administration; the composition is prepared to achieve a daily dose of about 100 mg/m$^2$ following parenteral administration; the composition is prepared to achieve a daily dose of about 125 mg/m$^2$ following parenteral administration; the composition is prepared to achieve a daily dose of about 150 mg/m$^2$ following parenteral administration; the composition is prepared to achieve a daily dose of between about 50 mg/m$^2$ and about 100 mg/m$^2$ following parenteral administration; the composition is prepared for parenteral administration in combination with an additional therapeutic agent selected from any additional therapeutic agent disclosed herein; the composition is prepared for treating myelodysplastic syndrome or acute myelogenous leukemia; the composition is a single unit dosage form; and/or the composition further comprises an excipient selected from any excipient disclosed herein.

Specific embodiments herein provide, inter alia, uses of 5-azacytidine for the preparation of a pharmaceutical composition for treating a disease associated with abnormal cell proliferation (e.g., MDS), wherein the composition is prepared for parenteral administration, and wherein the composition is prepared from cold sterile water (e.g., having a temperature of about 0° C., about 2° C., about 4° C., about 6° C., about 8° C., or about 10° C.). Further embodiments herein provide the aforementioned uses, in which: the disease is myelodysplastic syndrome or acute myelogenous leukemia; the amount of 5-azacytidine is selected from any amount disclosed herein; and/or the composition is prepared for immediate parenteral use or for parenteral use after storage for a certain period of time. Further embodiments provide, inter alia, methods for treating a subject having a disease or disorder provided herein by administering a pharmaceutical compositions provided herein, wherein the treatment results in improved survival of the subject.

In particular embodiments, the pharmaceutical compositions comprising the cytidine analogs, such as, for example, 5-azacytidine or decitabine, comprise a therapeutically or prophylactically effective amount of the cytidine analog (and, optionally, one or more excipients). In particular embodiments, the pharmaceutical compositions comprising the cytidine analogs, such as, for example, 5-azacytidine or decitabine, is prepared to deliver a therapeutically or prophylactically effective amount of the cytidine analog to a subject in need thereof.

In one embodiment, provided herein are methods of treating patho-physiological conditions manifested by abnormal cell proliferation, such as, for example, cancer, including hematological disorders and solid tumors, by parenterally administering a pharmaceutical formulation comprising a cytidine analog, such as, for example, 5-azacytidine or decitabine. Other embodiments herein provide methods of treating immune disorders. In certain embodiments, the cytidine analog and one or more therapeutic agents are co-administered to subjects to yield a synergistic therapeutic effect. The co-administered agent may be a cancer therapeutic agent dosed orally or by injection.

In certain embodiments, methods provided herein for treating disorders related to abnormal cell proliferation comprise parenterally administering a formulation comprising a therapeutically effective amount of a cytidine analog. Particular therapeutic indications relating to the methods provided herein are disclosed herein. In certain embodiments, the therapeutically effective amount of the cytidine analog in the pharmaceutical formulation is an amount as disclosed herein. In certain embodiments, the precise therapeutically effective amount of the cytidine analog in the pharmaceutical formulation will vary depending on, e.g., the age, weight, disease and/or condition of the subject.

In particular embodiments, the disorders related to abnormal cell proliferation include, but are not limited to, MDS, AML, ALL, CML, leukemia, chronic lymphocytic leukemia (CLL), lymphoma (including non-Hodgkin's lymphoma (NHL) and Hodgkin's lymphoma), multiple myeloma (MM), sarcoma, melanoma, carcinoma, adenocarcinoma, chordoma, breast cancer, colorectal cancer, ovarian cancer, lung cancer (e.g., non-small-cell lung cancer and small-cell lung cancer), testicular cancer, renal cancer, pancreatic cancer, bone cancer, gastric cancer, head and neck cancer, and prostate cancer. In particular embodiment, the disorder related to abnormal cell proliferation is MDS. In particular embodiments, the disorder related to abnormal cell proliferation is AML.

In certain embodiments, methods provided herein comprise treating a disorder provided herein, including a hematologic disorder, by administering a parenteral dosage form comprising a cytidine analog to a subject in need thereof. In particular embodiments, parenteral dosage forms provided herein comprising 5-azacytidine are used to treat subjects having hematologic disorders. In particular embodiments, parenteral dosage forms provided herein comprising decitabine are used to treat subjects having hematologic disorders. Hematologic disorders include, e.g., abnormal growth of blood cells which can lead to dysplastic changes in blood cells and hematologic malignancies such as various leukemias. Examples of hematologic disorders include, but are not limited to, acute myeloid leukemia (AML), acute promyelocytic leukemia (APML), acute lymphoblastic leukemia (ALL), chronic myelogenous leukemia (CML), chronic lymphocytic leukemia (CLL), myelodysplastic syndromes (MDS), and sickle cell anemia, among others. Other disorders that can be treated using the methods provided herein include, e.g., multiple myeloma (MM) and non-Hodgkin's lymphoma (NHL).

In certain embodiments, methods provided herein comprise treating AML by administering a parenteral dosage form comprising a cytidine analog to a subject in need thereof. AML is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia.

In certain embodiments, methods provided herein comprise treating APML by administering a parenteral dosage form comprising a cytidine analog to a subject in need thereof. APML represents a distinct subgroup of AML. This subtype is characterized by promyelocytic blasts containing the 15; 17 chromosomal translocation. This translocation leads to the generation of the fusion transcript comprised of the retinoic acid receptor and a sequence PML.

In certain embodiments, methods provided herein comprise treating ALL by administering a parenteral dosage form comprising a cytidine analog to a subject in need thereof. ALL is a heterogenerous disease with distinct clinical features displayed by various subtypes. Reoccurring cytogenetic abnormalities have been demonstrated in ALL. The most common cytogenetic abnormality is the 9; 22 translocation. The resultant Philadelphia chromosome represents poor prognosis of the subject.

In certain embodiments, methods provided herein comprise treating CML by administering a parenteral dosage form comprising a cytidine analog to a subject in need thereof. CML is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

In certain embodiments, methods provided herein comprise treating MDS by administering a parenteral dosage form comprising a cytidine analog to a subject in need thereof. In certain embodiments, MDS includes one or more of the following myelodysplastic syndrome subtypes:

refractory anemia, refractory anemia with ringed sideroblasts (if accompanied by neutropenia or thrombocytopenia or requiring transfusions), refractory anemia with excess blasts, refractory anemia with excess blasts in transformation, and chronic myelomonocytic leukemia. In certain embodiments, the MDS is higher-risk MDS. See, e.g., U.S. patent application Ser. No. 12/740,636, which is incorporated by reference herein in its entirety. In certain embodiments, the methods provided herein comprise administering a parenteral dosage form comprising a cytidine analog to a subject in need thereof to increase the survival (e.g., prolong the life) of a subject with MDS.

In certain embodiments, methods provided herein comprise treating NHL by administering a parenteral dosage form comprising a cytidine analog to a subject in need thereof. Non-Hodgkin's Lymphomas (NHL) represent a heterogeneous group of malignancies of the lymphoid system. According to the WHO classification of hematological and lymphoid tumors, these diseases are classified as B-cell and T-cell neoplasms. B-cell lymphomas account for about 90% of all lymphomas, and the two most common histological disease entities are follicular lymphoma and diffuse large B-cell lymphoma. Approximately 55,000 to 60,000 new cases of NHL are diagnosed annually in the U.S. See, e.g., Ansell, S. M., et al., *Mayo Clin. Proc.*, 2005, 80(8): 1087-97.

In certain embodiments, methods provided herein comprise treating MM by administering a parenteral dosage form comprising a cytidine analog to a subject in need thereof. Multiple myeloma is one of the most commonly diagnosed hematologic malignancies. In 2007, in the U.S. alone, there were roughly 20,000 new MM cases and 10,000 deaths due to MM. The disease is characterized by, inter alia, an accumulation of malignant plasma cells in the bone marrow, which can lead to the overproduction of an immunoglobulin, e.g., a monoclonal immunoglobulin G or A. These immunoglobulins, also known as paraproteins, can be detected in the urine and blood of patients with MM. Consequences of MM include anemia, the development of destructive bony lesions, and renal insufficiency. See, e.g., Rao, K. V., *American Journal of Health-System Pharmacy*, 2007, 64(17):1799-1807.

In certain embodiments, methods provided herein comprise treating CLL by administering a parenteral dosage form comprising a cytidine analog to a subject in need thereof. Chronic lymphocytic lymphoma (CLL) is a malignancy of mature B lymphocytes and is the most prevalent lymphoid malignancy in the U.S. The WHO classification of B lymphocytic neoplasms groups B cell malignancies according to the presumed normal counterpart of the malignant cells. CLL is diagnosed by immunophenotype analysis of lymphocytes from the blood, bone marrow, or lymph nodes. See, e.g., Zent, C. S., et al., *Current Oncology Reports*, 2007, 9:345-52.

Certain embodiments herein provide methods of treating a condition involving undesirable or uncontrolled cell proliferation by administering a parenteral formulation comprising a cytidine analog (e.g., 5-azacytidine or decitabine) as provided herein. Such conditions include, e.g., benign tumors, various types of cancers such as primary tumors and tumor metastasis, hematological disorders (e.g. leukemia, myelodysplastic syndrome and sickle cell anemia), restenosis (e.g. coronary, carotid, and cerebral lesions), abnormal stimulation of endothelial cells (arteriosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

In certain embodiments, cells in a benign tumor retain their differentiated features and do not divide in a completely uncontrolled manner. A benign tumor may be localized and/or nonmetastatic. Specific types of benign tumors that can be treated using the methods, compositions, and formulations provided herein include, e.g., hemangiomas, hepatocellular adenoma, cavernous hemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In certain embodiments, cells in a malignant tumor become undifferentiated, do not respond to the body's growth control signals, and/or multiply in an uncontrolled manner. The malignant tumor may be invasive and capable of spreading to distant sites (metastasizing). Malignant tumors may be divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.).

Methylation can lead to the silencing of genes critical to cellular control (i.e., epigenetic gene silencing), and can be an early event in the development of malignant tumors including, e.g., colorectal cancer or lung cancer. See, e.g., M. V. Brock et al., *N. Engl. J. Med.*, 2008, 358(11):1118-28; P. M. Das et al., *Mol. Cancer*, 2006, 5(28); G. Gifford et al., *Clin. Cancer Res.*, 2004, 10:4420-26; J. G. Herman et al., *N. Engl. J. Med.*, 2003, 349:2042-54; A. M. Jubb et al., *J. Pathology*, 2001, 195:111-34. Accordingly, in certain embodiments, methods herein provide using parenteral formulations provided herein to prevent or reverse epigenetic gene silencing, e.g., by reversing abnormal DNA methylation. In specific embodiments, parenteral formulations provided herein are used for early intervention to prevent the development of cancer in patients at risk of developing cancer, e.g., familial polyposis or lung cancer, wherein a cause of the cancer is epigenetic gene silencing. In specific embodiments, the formulations provided herein are used for early intervention to prevent the recurrence of cancer in patients at risk for early relapse, e.g., colorectal cancer or non-small-cell lung cancer. In certain embodiments, the early intervention is achieved via prolonged dosing schedules, using formulations and/or methods as described herein. Certain embodiments provide methods for administering the formulations provided herein to reverse the effect of gene silencing, e.g., in patients at risk of gene silencing due to epigenetic changes. In particular embodiments, methods provided herein further comprise administering an HDAC inhibitor compound (e.g., to restore chromatin to a transcriptionally active configuration after reversing abnormal DNA methylation). In particular embodiments, the HDAC inhibitor compound is entinostat (SNDX-275; formerly MS-275), an oral HDAC inhibitor that acts synergistically with targeted therapies and is selective for cancer-relevant HDAC isoforms 1, 2, and 3. In particular embodiments, a synergistic effect is achieved by co-administering 5-azacytidine and an HDAC inhibitor (e.g., entinostat) for the treatment of solid tumors (e.g., NSCLC) or hematological malignancies (e.g., MDS, CMMoL, or AML).

In certain embodiments, specific types of cancers or malignant tumors, either primary or secondary, that can be treated using the methods, compositions, and formulations provided herein include, e.g., leukemia, breast cancer, skin cancer, bone cancer, prostate cancer, liver cancer, lung cancer (e.g., non-small-cell lung cancer and small-cell lung cancer), brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronmas, intestinal ganglioneuromas, hyperplastic corneal nerve tumor, marfanoid habitus tumor, Wilm's tumor, seminoma, ovarian tumor, leiomyoma tumor, cervical dysplasia and in situ carcinoma, neuroblastoma, retinoblastoma, medulloblastoma, soft tissue sarcoma, malignant carcinoid, topical skin lesion, mycosis fungoides, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Particular embodiments herein provide using the methods, compositions, and formulations provided herein to treat abnormal cell proliferation due to, e.g., insults to body tissue during surgery for a variety of surgical procedures, including, e.g., joint surgery, bowel surgery, and cheloid scarring. Proliferative responses associated with organ transplantation that may be treated using the methods, compositions, and formulations provided herein include those proliferative responses contributing to potential organ rejections or associated complications. Specifically, these proliferative responses may occur during transplantation of the heart, lung (e.g., non-small-cell lung cancer and small-cell lung cancer), liver, kidney, and other body organs or organ systems.

In certain embodiments, the amount of the cytidine analog in the formulations provided herein, the methods of administration thereof, or the methods of treatment as set forth herein, is a specific dosage amount as provided herein. In certain embodiments, the 5-azacytidine or decitabine dosages, methods of administration thereof, or methods of treatment of at least one condition, including but not limited to MDS and AML, may range, e.g., between about 50 mg/m$^2$/day and about 2,000 mg/m$^2$/day, between about 50 mg/m$^2$/day and about 1,000 mg/m$^2$/day, between about 50 mg/m$^2$/day and about 500 mg/m$^2$/day, or between about 50 mg/m$^2$/day and about 100 mg/m$^2$/day. In certain embodiments, particular dosages are, e.g., about 20 mg/m$^2$/day, about 40 mg/m$^2$/day, about 50 mg/m$^2$/day, about 60 mg/m$^2$/day, about 70 mg/m$^2$/day, about 80 mg/m$^2$/day, about 90 mg/m$^2$/day, about 100 mg/m$^2$/day, about 110 mg/m$^2$/day, about 120 mg/m$^2$/day, about 140 mg/m$^2$/day, about 150 mg/m$^2$/day, about 160 mg/m$^2$/day, about 180 mg/m$^2$/day, about 200 mg/m$^2$/day, about 220 mg/m$^2$/day, about 250 mg/m$^2$/day, about 280 mg/m$^2$/day, or about 300 mg/m$^2$/day.

In certain embodiments, appropriate biomarkers may be used to determine or predict the effect of the pharmaceutical compositions comprising cytidine analogs on the disease state and to provide guidance to the dosing schedule. For example, particular embodiments herein provide a method of determining whether a patient diagnosed with MDS has an increased probability of obtaining a greater benefit from treatment with a pharmaceutical composition comprising a cytidine analog by assessing the patient's nucleic acid methylation status. In particular embodiments, the cytidine analog is 5-azacytidine. In particular embodiments, the cytidine analog is decitabine. In particular embodiments, the nucleic acid is DNA or RNA. In particular embodiments, the greater benefit is an overall survival benefit. In particular embodiments, the methylation status is examined in one or more genes, e.g., genes associated with MDS or AML. Specific embodiments involve methods for determining whether baseline DNA methylation levels influence overall survival in patients with MDS (e.g., higher risk MDS) treated with 5-azacytidine or decitabine. Specific embodiments provide methods for determining whether gene promoter methylation levels influence overall survival in patients with MDS (e.g., higher risk MDS).

For example, specific embodiments herein provide methods for evaluating the influence of gene methylation on prolonged survival in patients with MDS (e.g., higher risk MDS). In particular embodiments, such evaluation is used to predict overall survival in patients with MDS (e.g., higher risk MDS), e.g., upon treatment with a pharmaceutical composition comprising a cytidine analog, as provided herein. In particular embodiments, such evaluation is used for therapeutic decision-making. In specific embodiments, such therapeutic decision-making includes planning or adjusting a patient's treatment, e.g., the dosing regimen, amount, and/or duration of administration of the cytidine analogue.

Certain embodiments provide methods of identifying individual patients diagnosed with MDS having an increased probability of obtaining an overall survival benefit from cytidine analog treatment, using analysis of methylation levels, e.g., in particular genes. In specific embodiments, lower levels of nucleic acid methylation are associated with an increased probability of obtaining improved overall survival following 5-azacytidine treatment. In particular embodiments, the increased probability of obtaining improved overall survival following treatment is at least a 5% greater probability, at least a 10% greater probability, at least a 20% greater probability, at least a 30% greater probability, at least a 40% greater probability, at least a 50% greater probability, at least a 60% greater probability, at least a 70% greater probability, at least an 80% greater probability, at least a 90% greater probability, at least at least a 100% greater probability, at least a 125% greater probability, at least a 150% greater probability, at least a 175% greater probability, at least a 200% greater probability, at least a 250% greater probability, at least a 300% greater probability, at least a 400% greater probability, or at least a 500% greater probability of obtaining improved overall survival following treatment, e.g., using a pharmaceutical composition comprising a cytidine analog as provided herein. In particular embodiments, the greater probability of obtaining improved overall survival following treatment is a greater probability as compared to the average probability of a particular comparison population of patients diagnosed with MDS. In specific embodiments, the comparison population is a group of patients classified with a particular myelodysplastic subtype, as described herein. In one embodiment, the comparison population consists of patients having higher risk MDS. In particular embodiments, the comparison population consists of a particular IPSS cytogenetic subgroup.

In particular embodiments, nucleic acid (e.g., DNA or RNA) hypermethylation status may be determined by any method known in the art. In certain embodiments, DNA hypermethylation status may be determined using the bone marrow aspirates of patients diagnosed with MDS, e.g., by using quantitative real-time methylation specific PCR ("qMSP"). In certain embodiments, the methylation analysis may involve bisulfite conversion of genomic DNA. For example, in certain embodiments, bisulfite treatment of DNA is used to convert non-methylated CpG sites to UpG, leaving methylated CpG sites intact. See, e.g., Frommer, M., et al., *Proc. Nat'l Acad. Sci. USA* 1992, 89:1827-31. Commercially available kits may be used for such bisulfite treatment. In certain embodiments, to facilitate methylation PCR, primers are designed as known in the art, e.g., outer primers which amplify DNA regardless of methylation status, and nested primers which bind to methylated or non-methylated sequences within the region amplified by the first PCR. See, e.g., Li et al., *Bioinformatics* 2002, 18:1427-31. In certain embodiments, probes are designed, e.g., probes which bind to the bisulfite-treated DNA regardless of methylation status. In certain embodiments, CpG methylation is detected, e.g., following PCR amplification of bisulfite-treated DNA using outer primers. In certain embodiments, amplified product from the initial PCR reaction serves as a template for the nested PCR reaction using methylation-specific primers or non-methylation-specific primers. In certain embodiments, a standard curve is established to determine the percentage of methylated molecules in a particular sample. Methods for detecting nucleic acid methylation (e.g., RNA or DNA methylation) are known in art. See, e.g., Laird, P. W., *Nature Rev. Cancer* 2003, 3:253-66; Belinsky, S. A., *Nature Rev. Cancer* 2004, 4:1-11.

In certain embodiments, statistical analyses are performed to assess the influence of particular methylation levels with the potential benefit of treatment with a particular pharmaceutical composition comprising a cytidine analog. In certain embodiments, the influence of methylation on overall survival is assessed, e.g., using Cox proportional hazards models and Kaplan-Meier (KM) methodology.

In certain embodiments, any gene associated with MDS and/or AML may be examined for its methylation status in a patient. Particular genes include, but are not limited to, CKDN2B (p15), SOCS1, CDH1 (E-cadherin), TP73, and CTNNA1 (alpha-catenin). Particular genes associated with MDS and/or AML, which would be suitable for use in the methods disclosed here, are known in the art.

Certain embodiments herein provide methods for delivering a cytidine analog to a subject comprising administering to the subject in need thereof a parenteral formulation comprising a cytidine analog. In certain embodiments, provided herein is a method of accurately deliver an intended dose of a cytidine analog to a subject comprising administering to the subject in need thereof a parenteral formulation comprising a cytidine analog as provided herein.

In some embodiments, methods provided herein for treating disorders of abnormal cell proliferation comprise administering a cytidine analog using at least one of IV, SC and oral administration methods. For example, particular embodiments herein provide administering an initial treatment cycle of a cytidine analog, such as, for example, 5-azacytidine or decitabine, administered either SC or IV, followed by subsequent SC, IV, or orally administered treatment cycles of the cytidine analog. In certain embodiments, treatment cycles comprise multiple doses administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, or greater than 21 days). Particular embodiments herein provide a treatment schedule comprising SC and/or IV administration for one, two, three, four, five, or more initial cycles, followed by SC, IV, and/or oral administration for subsequent cycles. For example, particular embodiments herein provide a treatment schedule comprising SC or IV administration for cycle 1, followed by SC, IV, or oral administration for subsequent cycles. Suitable dosage ranges and amounts for the methods provided herein are provided throughout the specification. For example, in certain embodiments, the SC or IV dose is about 50 mg/m$^2$, about 75 mg/m$^2$, or about 100 mg/m$^2$. In certain embodiments, the oral dose is about 60 mg, about 80 mg, about 120 mg, about 180 mg, about 240 mg, about 300 mg, about 360 mg, about 480 mg, or greater than about 480 mg. In certain embodiments, oral doses are calculated to achieve 80%, 100%, or 120% of SC AUC. Certain oral formulations or oral administration methods are described in U.S. patent application Ser. No. 12/466,213, which is incorporated by reference herein in its entirety.

In certain embodiments, methods of treating disorders of abnormal cell proliferation comprises parenterally administering a formulation comprising a cytidine analog (e.g., 5-azacytidine or decitabine) as single or multiple daily doses. In particular embodiments, the formulation(s) comprising the cytidine analog is/are parenterally administered once per day, twice per day, three times per day, four times per day, or more than four times per day. For example, in certain embodiments, the formulation comprising the cytidine analog is administered using a treatment cycle comprising administration of about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg of the cytidine analog once, twice, three, or four times per day for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

In certain embodiments, the method of treating comprises continuous low-dose administration. Certain embodiments herein provide methods comprising administering the formulations of cytidine analogs provided herein comprising delivering the cytidine analog (e.g., 5-azacytidine or decitabine) at a lower dose over a more prolonged period of time. In particular embodiments, such methods comprise managing dose-related cytopenias (including, e.g., dose-related cytopenias associated with 5-azacytidine) by administering a formulation provided herein. In particular embodiments, certain methods herein provide administering the formulations provided herein at lower doses for more prolonged periods of time, leading to improved demethylation.

In certain embodiments, methods provided herein comprise administering a formulation comprising a cytidine analog using one or more of the cycles provided herein, and repeating one or more of the cycles for a period of, e.g., 1, 2, 3, 4, 5, 6, 7, 8, 9, 10, 11, 12, or greater than 12 months.

Particular embodiments herein provide methods for treating a subject having a disease or disorder provided herein by parenterally administering a pharmaceutical composition provided herein, wherein the treatment results in improved survival of the subject. In certain embodiments, the improved survival is measured as compared to one or more conventional care regimens. Particular embodiments herein provide methods for treating a subject having a disease or disorder provided herein by parenterally administering a pharmaceutical composition provided herein, wherein the treatment provides improved effectiveness. In particular embodiments, the improved effectiveness is measured using one or more endpoints for cancer clinical trials, as recommended by the U.S. Food and Drug Administration (FDA). For example, FDA provides Guidance for Industry on Clinical Trial Endpoints for the Approval of Cancer Drugs and Biologics (http://www.fda.gov/CbER/gdlns/clintrialend.htm). The FDA endpoints include, but are not limited to, Overall Survival, Endpoints Based on Tumor Assessments such as (i) Disease-Free Survival (ii) Objective Response Rate, (iii) Time to Progression and Progression-Free Survival and (iv) Time-to-Treatment Failure. Endpoints Involving Symptom Endpoints may include Specific Symptom Endpoints such as (i) Time to progression of cancer symptoms and (ii) A composite symptom endpoint. Biomarkers assayed from blood or body fluids may also be useful to determine the management of the disease.

Particular embodiments herein provide a method of treating a disease or disorder, including cancer, disorders related to abnormal cell proliferation, and hematologic disorders (e.g., MDS), using a pharmaceutical composition comprising 5-azacytidine, as provided herein elsewhere, wherein the method comprises administering about 75 mg/m$^2$ of 5-azacytidine per day for 7 days. In one embodiment, the pharmaceutical composition comprising 5-azacytidine is administered parenterally. In one embodiment, the pharmaceutical composition comprising 5-azacytidine is administered subcutaneously or intravenously. In certain embodiments, the subject may be premedicated for nausea and/or vomiting prior to treatment. In certain embodiments, the daily dose is about 50 mg/m$^2$, about 75 mg/m$^2$, or about 100 mg/m$^2$. In certain embodiments, the daily dose is between about 50 mg/m$^2$ and about 100 mg/m$^2$. In certain embodiments, the average daily dose is between about 50 mg/m$^2$ and about 100 mg/m$^2$.

In certain embodiments, provide herein is a method of treating a disease or disorder, including cancer, disorders related to abnormal cell proliferation, and hematologic disorders (e.g., MDS), using a pharmaceutical composition comprising 5-azacytidine, as provided herein elsewhere, wherein the method comprises carrying out the treatment in cycles, wherein the first treatment cycle comprises administering about 75 mg/m$^2$ of 5-azacytidine per day for 7 days, followed by a 21-day break. In certain embodiments, the treatment cycle is repeated every 4 weeks (e.g., treatment for 7 days, followed by a 21-day break).

In certain embodiments, after the first two treatment cycles, the dose is increased to about 100 mg/m$^2$ of 5-azacytidine per day for 7 days, followed by a 21-day break, for example, when no toxicity other than nausea and vomiting has occurred during the first two treatment cycles and if appropriate for the treated subject. In other embodiments, the dose is maintained at about 75 mg/m$^2$ of 5-azacytidine per day for 7 days, followed by a 21-day break, and the treatment cycle is repeated as provided herein.

In certain embodiments, the treatment is continued for at least 4 to 6 cycles. In certain embodiments, the treatment cycle is continued until a complete or partial response is observed in the treated subject. In certain embodiments, the treatment cycle is continued as long as the treated subject continues to benefit. In certain embodiments, the treated subjects are monitored for hematologic response and renal toxicities, and the dosage is delayed or reduced (e.g., by about 33%, about 50%, about 67%, or about 75%, in the next cycle), as appropriate.

In certain embodiments, the cytidine analog, e.g., 5-azacytidine or decitabine, is not co-administered with a cytidine deaminase inhibitor. In certain embodiments, the formulation comprising a cytidine analog as provided herein is not co-administered with THU. Certain embodiments herein provide methods of treating a disease or disorder provided herein (e.g., a disease associated with abnormal cell proliferation) comprising parenterally administering a cytidine analog provided herein (e.g., 5-azacytidine or decitabine), wherein the methods comprise not co-administering a cytidine deaminase inhibitor with the cytidine analog. Certain embodiments herein provide methods of treating a disease or disorder provided herein (e.g., a disease associated with abnormal cell proliferation) comprising parenterally administering a cytidine analog provided herein (e.g., 5-azacytidine or decitabine), wherein the methods avoid adverse effects associated with administering a cytidine deaminase inhibitor (e.g., THU) by not co-administering the cytidine deaminase inhibitor with the cytidine analog. In particular embodiments, a cytidine deaminase inhibitor (e.g., THU) is co-administered with the cytidine analog in an amount of, e.g., less than about 500 mg/d, less than about 200 mg/d, less than about 150 mg/d, less than about 100 mg/d, less than about 50 mg/d, less than about 25 mg/d, less than about 10 mg/d, less than about 5 mg/d, less than about 1 mg/d, or less than about 0.1 mg/d.

Certain embodiments herein provide methods of treating diseases or disorders disclosed herein (e.g., diseases or disorders involving abnormal cell proliferation), wherein the methods comprise co-administering a parenteral formulation disclosed herein (such as, for example, a formulation comprising 5-azacytidine, or a formulation comprising decitabine) with one or more additional therapeutic agents (such as, for example, a cancer therapeutic agent) to yield a synergistic therapeutic effect. In certain embodiments, the additional therapeutic agent is co-administered concurrently with a parenteral formulation provided herein. In certain embodiments, the additional therapeutic agent is co-administered sequentially (e.g., prior to or following the administration of a parenteral formulation provided herein). Particular co-administered therapeutic agents useful in the methods disclosed herein are disclosed throughout the specification. In particular embodiments, the additional therapeutic agent is co-administered in an amount that is a therapeutically effective amount. In particular embodiments, the additional therapeutic agent is co-administered in a separate dosage form from the cytidine analog dosage form with which it is co-administered. In particular embodiments, the additional therapeutic agent is co-administered in a dosage form (e.g., a single unit dosage form) together with the cytidine analog with which it is co-administered. In such cases, the cytidine analog (e.g., 5-azacytidine or decitabine) and the additional therapeutic agent may be co-formulated together in the same dosage form using methods of co-formulating active pharmaceutical ingredients, including methods disclosed herein and methods known in the art.

In particular embodiments, the cytidine analog formulations provided herein further comprise one, two, three, or more other pharmacologically active substances (also termed herein "additional therapeutic agents," "second active agents," or the like). In particular embodiments, the formulations provided herein comprise the additional therapeutic agent(s) in a therapeutically effective amount. In particular embodiments, the cytidine analog (e.g., 5-azacytidine or decitabine) and the additional therapeutic agent(s) are co-formulated together in the same dosage form using methods of co-formulating active pharmaceutical ingredients, including methods disclosed herein and methods known in the art. In other embodiments, the cytidine analog and the additional therapeutic agent(s) are co-administered in separate dosage forms. It is believed that certain combinations work synergistically in the treatment of particular diseases or disorders, including, e.g., types of cancer and certain diseases and conditions associated with, or characterized by, undesired angiogenesis or abnormal cell proliferation. Cytidine analog dosage forms provided herein can also work to alleviate adverse effects associated with certain second active agents, and some second active agents can be used to alleviate adverse effects associated with cytidine analog dosage forms provided herein. In certain embodiments, the formulations provided herein are co-administered with one or more therapeutic agents to provide a resensitization effect in subjects in need thereof. Additional therapeutic agents can be, e.g., large molecules (e.g., proteins) or small molecules (e.g., synthetic inorganic, organometallic, or organic molecules).

Examples of particular additional therapeutic agents useful in the compositions and methods disclosed herein include, but are not limited to, e.g., cytotoxic agents, antimetabolites, antifolates, HDAC inhibitors (e.g., entinostat, also known as SNDX-275 or MS-275; or vorinostat, also known as suberoylanilide hydroxamic acid (SAHA) or N-hydroxy-N-phenyl-octanediamide), DNA intercalating agents, DNA cross-linking agents, DNA alkylating agents, DNA cleaving agents, topoisomerase inhibitors, CDK inhibitors, JAK inhibitors, anti-angiogenic agents, Bcr-Abl inhibitors, HER2 inhibitors, EGFR inhibitors, VEGFR inhibitors, PDGFR inhibitors, HGFR inhibitors, IGFR inhibitors, c-Kit inhibitors, Ras pathway inhibitors, PI3K inhibitors, multi-targeted kinase inhibitors, mTOR inhibitors, anti-estrogens, anti-androgens, aromatase inhibitors, somatostatin analogs, ER modulators, anti-tubulin agents, vinca alkaloids, taxanes, HSP inhibitors, Smoothened antagonists, telomerase inhibitors, COX-2 inhibitors, anti-metastatic agents, immunosuppressants, biologics such as antibodies, and hormonal therapies. In particular embodiments, the co-administered therapeutic agent is an immunomodulatory compound, e.g., thalidomide, lenalidomide, or pomalidomide. The co-administered agent may be dosed, e.g., orally or by injection.

Other examples of additional therapeutic agents include, but are not limited to, hematopoietic growth factor, a cytokine, an anti-cancer agent, granulocyte colony-stimulating factor (G-CSF), granulocyte-macrophage colony-stimulating factor (GM-CSF), erythropoietin (EPO), interleukin (IL), interferon (IFN), oblimersen, melphalan, topotecan, pentoxifylline, taxotere, paclitaxel (e.g., Abraxane®), docetaxel, irinotecan, ciprofloxacin, doxorubicin, vincristine, dacarbazine, Ara-C, vinorelbine, prednisone, cyclophosphamide, bortezomib, arsenic trioxide. Such additional therapeutic agents are particularly useful in methods and compositions disclosed herein including, but not limited to, those relating to treatment of multiple myeloma.

Other examples of additional therapeutic agents include, but are not limited to, an antibody (e.g., rituximab, anti-CD33), hematopoietic growth factor, cytokine, anti-cancer agent, antibiotic, COX-2 inhibitor, immunomodulatory agent, immunosuppressive agent, corticosteroid, or a pharmacologically active mutant or derivative thereof. See, e.g., S. N and et al., *Leukemia and Lymphoma*, 2008, 49(11): 2141-47 (describing a Phase II study involving the administration of a combination of hydroxyurea, 5-azacytidine and low dose gemtuzumab ozogamicin to elderly patients with AML and high-risk MDS, and concluding that this combination appears to be a safe and effective regimen in the treatment of AML and high risk MDS in this group of patients). Such additional therapeutic agents are particularly useful in methods and compositions disclosed herein including, but not limited to, those relating to treatment of the diseases and disorders disclosed herein.

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions provided herein include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Embodiments herein encompass the use of native, naturally occurring, and recombinant proteins. Particular embodiments encompass mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with the formulations comprising cytidine analogs disclosed herein include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. Formulations comprising cytidine analogs disclosed herein can also comprise, be combined with, or used in combination with anti-TNF-α antibodies.

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits provided herein. See, e.g., Emens, L. A., et al., *Curr. Opinion Mol. Ther.* 3(1):77-84 (2001).

In one embodiment, the additional therapeutic agent (e.g., large-molecule compound or small-molecule compound) reduces, eliminates, or prevents an adverse effect associated with the administration of a cytidine analog provided herein. Depending on the particular cytidine analog and the disease or disorder begin treated, adverse effects can include, but are not limited to, anemia, neutropenia, febrile neutropenia, thrombocytopenia, hepatotoxicity (e.g., including, but not limited to, hepatotoxicity in patients with preexisting hepatic impairment), elevated serum creatinine, renal failure, renal tubular acidosis, hypokalemia, hepatic coma, nausea, vomiting, dyspepsia, abdominal pain, pyrexia, leukopenia, diarrhea, constipation, ecchymosis, petechiae, rigors, weakness, pneumonia, anxiety, insomnia, lethargy, and decrease in weight, among others known in the art to be associated with particular cytidine analogs.

Like some large molecules, many small-molecule compounds are believed to be capable of providing a synergistic effect when administered with (e.g., before, after or simultaneously) a cytidine analog formulation disclosed herein. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; 5-azacytidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®), imiquimod; immunostimulant peptides; insulin-like growth factor-1 receptor inhibitor;

interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In other embodiments, specific additional therapeutic agents include, but are not limited to, lenalidomide, pomalidomide, and thalidomide. In yet another embodiment, specific additional therapeutic agents include, but are not limited to, taxane, paclitaxel, docetaxel, paclitaxel protein-bound particles (e.g., Abraxane®), or docetaxel protein-bound particles. In yet another embodiment, specific additional therapeutic agents include, but are not limited to, a platinum agent (e.g., carboplatin).

Specific additional therapeutic agents include, but are not limited to, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

5.4 Cycling Therapy

In certain embodiments, the prophylactic or therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a compound provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a compound provided herein is administered daily and continuously for three or four weeks at a dose of from about 0.1 mg to about 5 mg per day, followed by a rest of one or two weeks. In other embodiments, the dose can be from about 1 mg to about 5 mg per day (e.g., 1, 2, 3, or 4 mg/day), given on Days 1-21 of each 28-day cycle until disease progression, followed by a rest of 7 days on Days 22-28 of each 28-day cycle, for example, in patients with relapsed and refractory multiple myeloma who are refractory to their last myeloma therapy and have received at least 2 prior therapies that included lenalidomide and bortezomib.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

In one embodiment, a compound provided herein is administered at a dose of about 4 mg per day given on Days 1-21, followed by a rest of 7 days on Days 22-28 of each 28-day cycle, alone or in combination with low dose dexamethasone (e.g., 40 mg/day given on Days 1, 8, 15 and 22 of each 28-day cycle), for example, in patients with relapsed and refractory multiple myeloma who are refractory to their last myeloma therapy and have received at least 2 prior therapies that included lenalidomide and bortezomib.

5.5 Pharmaceutical Compositions and Dosage Forms

Pharmaceutical compositions can be used in the preparation of single unit dosage forms comprising one or more solid forms provided herein. In one embodiment, provided herein are pharmaceutical compositions and dosage forms comprising one or more solid forms comprising a compound provided herein, or a pharmaceutically acceptable salt, solvate (e.g., hydrate), stereoisomer, co-crystal, clathrate, or prodrug thereof. Pharmaceutical compositions and dosage forms provided herein can further comprise one or more pharmaceutically acceptable excipients or carriers.

In some embodiments, pharmaceutical compositions and dosage forms provided herein can also comprise one or more additional active ingredients. Examples of optional second, or additional, active ingredients are disclosed herein elsewhere.

In one embodiment, single unit dosage forms provided herein are suitable for oral, parenteral (e.g., subcutaneous, intravenous, bolus injection, intramuscular, or intraarterial), topical (e.g., eye drops or other ophthalmic preparations), mucosal (e.g., nasal, sublingual, vaginal, buccal, or rectal), or transdermal administration to a patient. Examples of dosage forms include, but are not limited to: tablets; caplets; capsules, such as soft elastic gelatin capsules or hard gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient. In one embodiment, the single dosage forms provided herein are tablets, caplets, or capsules comprising one or more solid forms provided herein. In one embodiment, the single dosage forms provided herein are tablets or capsules comprising one or more solid forms provided herein.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences,* 18th ed., Mack Publishing, Easton Pa. (1990).

In one embodiment, pharmaceutical compositions and dosage forms comprise one or more excipients or carriers. Suitable excipients are known to those skilled in the art of pharmacy, and non-limiting examples of suitable excipients are provided herein. Whether a particular excipient is suitable for incorporation into a pharmaceutical composition or dosage form depends on a variety of factors known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, in one embodiment, provided are pharmaceutical compositions and dosage forms that contain little, if any, lactose or other mono- or di-saccharides. As used herein, the term "lactose-free" means that the amount of lactose present, if any, is insufficient to substantially increase the degradation rate of an active ingredient. Lactose-free compositions provided herein can comprise excipients which are known in the art and are listed in the *U.S. Pharmacopeia* (USP) 25-NF20 (2002), which is incorporated herein in its entirety.

Also provided are anhydrous pharmaceutical compositions and dosage forms comprising active ingredient(s), since water may facilitate the degradation of some compounds. Anhydrous pharmaceutical compositions and dosage forms can be prepared using anhydrous or low moisture containing ingredients and low moisture or low humidity conditions. An anhydrous pharmaceutical composition should be prepared and stored such that its anhydrous nature is maintained. Accordingly, in one embodiment, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise the active ingredient or solid form comprising 5-azacytidine and a coformer provided herein in an amount of from about 0.10 to about 10 mg, or from about 0.10 to about 5 mg. In other embodiments, dosage forms comprise a compound provided herein in an amount of about 0.1, 0.2, 0.3, 0.4, 0.5, 0.6, 0.7, 0.8, 0.9, 1, 2, 2.5, 3, 4, or 5 mg.

In other embodiments, dosage forms comprise a second active ingredient in an amount from about 1 mg to about 1000 mg, from about 5 mg to about 500 mg, from about 10 mg to about 350 mg, from about 5 mg to about 250 mg, from about 5 mg to about 100 mg, from about 10 mg to about 100 mg, from about 10 mg to about 50 mg, or from about 50 mg to about 200 mg. In one embodiment, the specific amount of the second active agent will depend on the specific agent used, the diseases or disorders being treated or managed, and the amount(s) of a compound provided herein, and any optional additional active agents concurrently administered to the patient.

In particular embodiments, provided herein is a pharmaceutical composition comprising a solid form comprising 5-azacytidine and a coformer provided herein and a pharmaceutically acceptable excipient or carrier. In particular embodiments, provided herein is a pharmaceutical composition comprising a cocrystal comprising 5-azacytidine and a coformer provided herein and a pharmaceutically acceptable excipient or carrier. In particular embodiments, provided herein is a pharmaceutical composition comprising an amorphous 5-azacytidine provided herein and a pharmaceutically acceptable excipient or carrier. Exemplary embodiments of formulations of 5-azacytidine are described in, for example, U.S. Pat. Nos. 5,635,517, 6,335,349, 6,316,471, 6,476,052, 7,041,680, and 7,709,502; and U.S. Patent Application Publication No. 2011/0045064; the entireties of which are incorporated herein by reference.

5.5.1 Oral Dosage Forms

Pharmaceutical compositions that are suitable for oral administration can be provided as discrete dosage forms, such as, but not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In one embodiment, such dosage forms contain predetermined amounts of active ingredients, and may be prepared by methods of pharmacy known to those skilled in the art. See generally, *Remington's Pharmaceutical Sciences,* 18th ed., Mack Publishing, Easton Pa. (1990). As used herein, oral administration also includes buccal, lingual, and sublingual administration.

In one embodiment, the oral dosage form provided herein is a tablet. In one embodiment, the oral dosage form provided herein is a capsule. In one embodiment, the oral dosage form provided herein is a caplet. In particular embodiments, In one embodiment, oral dosage forms provided herein are prepared by combining the active ingredients in an intimate admixture with one or more pharmaceutically acceptable carrier or excipient, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide, according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In specific embodiments, capsules comprising one or more solid forms comprising 5-azacytidine and a coformer provided herein can be used for oral administration. In one embodiment, the total amount of 5-azacytidine in the capsule is about 1 mg, about 2 mg, about 3 mg, about 4 mg, or about 5 mg. In one embodiment, the total amount of 5-azacytidine in the capsule is about 1 mg, about 2 mg, or about 4 mg. In one embodiment, the total amount of 5-azacytidine in the capsule is about 1 mg or about 2 mg. Each capsule can contain 5-azacytidine as the active ingredient and one or more of the following inactive ingredients: mannitol, pregelatinized starch and sodium stearyl fumarate. In specific embodiments, the 1 mg capsule shell can contain gelatin, titanium dioxide, FD&C blue 2, yellow iron oxide, white ink and black ink. In specific embodiments, the 2 mg capsule shell can contain gelatin, titanium dioxide, FD&C blue 2, yellow iron oxide, FD&C red 3 and white ink. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In certain embodiments, the dosage form is a tablet, wherein the tablet is manufactured using standard, art-recognized tablet processing procedures and equipment. In certain embodiments, the method for forming the tablets is direct compression of a powdered, crystalline and/or granular composition comprising a solid form provided herein, alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the dosage form is a capsule, wherein the capsules may be manufactured using standard, art-recognized capsule processing procedures and equipments. In certain embodiments, soft gelatin capsules may be prepared in which the capsules contain a mixture comprising a solid form provided herein and vegetable oil or non-aqueous, water miscible materials, such as, for example, polyethylene glycol and the like. In certain embodiments, hard gelatin capsules may be prepared containing granules of solid forms provided herein in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

Examples of excipients or carriers that can be used in oral dosage forms provided herein include, but are not limited to, diluents (bulking agents), lubricants, disintegrants, fillers, stabilizers, surfactants, preservatives, coloring agents, flavoring agents, binding agents (binders), excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, dosage forms provided herein comprise one or more binders. Binders may be used, e.g., to impart cohesive qualities to a tablet or a capsule, and thus ensure that the formulation remains intact after compression. Suitable binders include, but are not limited to, starch (including potato starch, corn starch, and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone (PVP), cellulosic polymers (including hydroxypropyl cellulose (HPC), hydroxypropylmethylcellulose (HPMC), methyl cellulose, ethyl cellulose, hydroxyethyl cellulose (HEC), carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, ceratonia, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein. In one embodiment, the binding agent can be, relative to the weight of the dosage form, in an amount of from about 50% to about 99% w/w. In certain embodiments, a suitable amount of a particular binder is determined by one of ordinary skill in the art.

Suitable forms of microcrystalline cellulose include, but are not limited to, the materials sold as AVICEL-PH-101, AVICEL-PH-103 AVICEL RC-581, AVICEL-PH-105 (FMC Corporation, Marcus Hook, Pa.), and mixtures thereof. In one embodiment, a specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in a pharmaceutical composition is, in one embodiment, present in from about 50 to about 99 weight percent of the pharmaceutical composition or dosage form.

In certain embodiments, dosage forms provided herein comprise one or more diluents. Diluents may be used, e.g., to increase bulk so that a practical size tablet or capsule is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule. The amount of a diluent in the pharmaceutical compositions provided herein varies upon the type of formulation, and is readily discernible to those of ordinary skill in the art.

Disintegrants may be used in the compositions to provide tablets or capsules that disintegrate when exposed to an aqueous environment. Dosage forms that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredient(s) may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

In one embodiment, a solid oral dosage form comprises a compound provided herein, and one or more excipients selector from anhydrous lactose, microcrystalline cellulose, polyvinylpyrrolidone, stearic acid, colloidal anhydrous silica, and gelatin. In one embodiment, capsules comprise one or more solid forms comprising 5-azacytidine and a coformer provided herein, and one or more of the following inactive ingredients: mannitol, pregelatinized starch, sodium stearyl fumarate, gelatin, titanium dioxide, FD&C blue 2, yellow iron oxide, white ink, black ink, FD&C red 3, and a combination thereof.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

6. EXAMPLES

Certain embodiments provided herein are illustrated by the following non-limiting examples.

In one embodiment, 5-azacytidine may be prepared using methods described in U.S. Pat. Nos. 6,943,249, 7,038,038, 7,858,774, and 8,058,424, all of which are incorporated herein in their entireties.

6.1 Preparation of Cocrystal Comprising 5-Azacytidine and a Coformer

Method A (Stoichiometric Slurry Experiments): Stoichiometric slurry experiments were carried out in glass vials. Each of the vials was charged with about 20 mg of 5-azacytidine, an approximately equimolar amount of coformer, and 500 µL of a saturated solution of the same coformer in the solvent used for that experiment. A magnetic stir bar was placed in each vial and the rack of vials was placed on a stir plate at room temperature for 24 hours. The solids were isolated by centrifugation.

Method B (Stoichiometric Wet Milling Experiments): For each experiment, A polyether ether ketone (PEEK) grinding cup was charged with about 20 mg of 5-azacytidine, an approximately equimolar amount of coformer, about 10 µL of a mixture of methanol and water (1:2), and one steel grinding ball. The cup was sealed and shaken on a Retsch mill for 20 min. The solid was collected.

Method C (Stoichiometric Flash Evaporation Experiments): All experiments were carried out using methanol:water (1:1) as solvent. The solvent was removed from solutions containing about 20 mg of 5-azacytidine and approximately equimolar amount of coformer on a rotary evaporator using a bath set at 80° C. If the residue was solid it was stored at 75% relative humidity for 1 day. If the residue was oil it was stored at 60° C. overnight. The resulting solids were collected.

In one embodiment, a cocrystal comprising 5-azacytidine and gallic acid was prepared by method A as described above using a solvent of methanol:water (1:2).

In one embodiment, a cocrystal comprising 5-azacytidine and maleic acid was prepared by method A as described above using a solvent of methanol:water (1:3). In another embodiment, a cocrystal comprising 5-azacytidine and maleic acid was prepared by method B as described above.

In one embodiment, a cocrystal comprising 5-azacytidine and nicotinamide was prepared by method A as described above using a solvent of methanol:water (1:2). In another embodiment, a cocrystal comprising 5-azacytidine and nicotinamide was prepared by method B as described above.

In one embodiment, a cocrystal comprising 5-azacytidine and ketoglutaric was prepared by method B as described above.

In one embodiment, a cocrystal comprising 5-azacytidine and mandelic acid was prepared by method B as described above.

In one embodiment, a cocrystal comprising 5-azacytidine and propyl gallate was prepared by method B as described above.

In one embodiment, a cocrystal comprising 5-azacytidine and cyclamic acid was prepared by method B as described above. In another embodiment, a cocrystal comprising 5-azacytidine and cyclamic acid was prepared by method C as described above.

In one embodiment, a cocrystal comprising 5-azacytidine and zinc chloride was prepared by method B as described above. In another embodiment, a cocrystal comprising 5-azacytidine and zinc chloride was prepared by method C as described above.

All of the samples generated were analyzed by X-ray powder diffraction (XRPD). The Rigaku Smart-Lab X-ray diffraction system was configured for reflection Bragg-Brentano geometry using a line source X-ray beam. The x-ray source was a Cu Long Fine Focus tube that was operated at 40 kV and 44 ma. That source provided an incident beam profile at the sample that changed from a narrow line at high angles to a broad rectangle at low angles. Beam conditioning slits were used on the line X-ray source to ensure that the maximum beam size was less than 10 mm both along the line and normal to the line. The Bragg-Brentano geometry was a para-focusing geometry controlled by passive divergence and receiving slits with the sample itself acting as the focusing component for the optics. The inherent resolution of Bragg-Brentano geometry was governed in part by the diffractometer radius and the width of the receiving slit used. Typically, the Rigaku Smart-Lab was operated to give peak widths of 0.1°2θ or less. The axial divergence of the X-ray beam was controlled by 5.0-degree Soller slits in both the incident and diffracted beam paths.

Powder samples were prepared in a low background Si holder using light manual pressure to keep the sample surfaces flat and level with the reference surface of the sample holder. The single-crystal, Si, low-background holder had a small circular recess (7 mm diameter and about 1 mm depth) that held between 5 and 10 mg of powdered material. Each sample was analyzed from 2 to 40°2θ using a continuous scan of 3°2θ per minute with an effective step size of 0.02°2θ.

DSC analyses were performed using a TA Instruments Q2000 DSC equipped with an autosampler tray. The instrument was cooled using a TA Instrument Refrigerated Cooling System (RCS) 90 chiller. The instrument temperature calibration was performed using indium. Each sample was weighed into a Tzero DSC pan, covered with a Tzero lid, and crimped. The sample pan was placed in the DSC autosampler tray for automated loading and analysis. An empty crimped Tzero pan was used as a reference and was also placed in the autosampler tray for automated loading. The DSC cell was kept under a nitrogen purge of about 50 mL per minute during each analysis. During analysis, the sample was heated from ambient temperature to about 350° C. at a rate of 10° C./minute. The instrument was controlled using Thermal Advantage Release 5.2.5 software and the data were analyzed using Universal Analysis 2000 for Windows version 4.5 A.

TGA analyses were performed using a TA Instruments Q50 TGA with external heat exchanger. The instrument balance was calibrated using class M weights and the temperature calibration was performed using alumel. The nitrogen purge was about 40 mL per minute at the balance and about 60 mL per minute at the furnace. Each sample was loaded into a pre-tared platinum TGA pan, which was then loaded onto the instrument. During analysis, the sample was heated from ambient temperature to about 350° C. at a rate of 10° C./minute. The instrument was controlled using Thermal Advantage Release 5.2.5 software and the data were analyzed using Universal Analysis 2000 for Windows version 4.5 A.

DVS analyses were carried out onusing a TA Instruments Q5000 Dynamic Vapor Sorption analyzer. The instrument was calibrated with standard weights and a sodium bromide standard for humidity. Samples were analyzed at 25° C. with a maximum equilibration time of 60 minutes in 10% relative humidity (RH) steps from 5 to 95% RH (adsorption cycle) and from 95 to 5% RH (desorption cycle).

Fourier transform (FT) Raman spectra were acquired on a Nicolet model 6700 spectrometer interfaced to a Nexus Raman accessory module. This instrument is configured with a Nd:YAG laser operating at 1024 nm, a CaF2 beamsplitter, and a indium gallium arsenide detector. OMNIC 8.1 software was used for control of data acquisition and processing of the spectra. Samples were packed into a 3-inch glass NMR tube for analysis.

The $^1$H NMR spectra were acquired on a Bruker DRX-500 spectrometer located at the Chemistry Department of Purdue University. Samples were prepared by dissolving material in DMSO-$d_6$. The solutions were filtered and placed into individual 5-mm NMR tubes for subsequent spectral acquisition. The temperature controlled (298K) $^1$H NMR spectra acquired on the DRX-500 utilized a 5-mm cryoprobe operating at an observing frequency Ion-selective Electrode (ISE) titrations were monitored using an Orion 9417B chloride electrode and an Orion 900200 reference electrode. A weighed amount of sample was dissolved in 60 mL of HPLC-grade water containing 5 mL of 10% nitric acid and 1.7 mL of Orion Ionplus® Ionic Strength Adjuster. The resulting solution was titrated with 0.025 M silver nitrate solution. Titration of a sodium chloride solution of known concentration was carried out to be sure the system was working properly.

Optical microscopy experiments were carried out on a Leica DM 2500 P compound microscope. Images were captured using a QImaging MicroPublisher 3.3 RTV camera.

A weighed amount of sample was dissolved in 60 mL of HPLC-grade water containing 5 mL of 10% nitric acid and 1.7 mL of Orion Ionplus® Ionic Strength Adjuster. The resulting solution was titrated with 0.025 M silver nitrate solution and monitored using an Orion 9417B chloride electrode and an Orion 900200 reference electrode. Titration of a sodium chloride solution of known concentration was carried out to be sure the system was working properly.

The general characterization methods described herein are non-limiting, and are intended merely as examples of parameters, methods and techniques which can be used to analyze certain embodiments provided herein. Other standard parameters, methods and techniques for chemical, biological, physiological and solid-state analysis are contemplated herein as means of characterizing various embodiments provided herein.

Solubility of 5-azacytidine in various solvents at ambient temperature was determined and is shown in Table 1. Solubility was estimated by treating a weighed sample of 5-azacytidine with measured aliquots of the test solvent at ambient temperature, with shaking and/or sonication between aliquots. Dissolution was determined by visual inspection. Solubility numbers were calculated by dividing the total amount of solvent used to dissolve the sample by the weight of the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than" if dissolution occurred on addition of the first solvent aliquot.

TABLE 1

| Solubility of 5-azacytidine | |
|---|---|
| Solvent | Solubility (mg/mL) |
| DMF | 1.7 |
| DMSO | 2.2 |
| 1:1 methanol/water | 2.8 |
| 1:2 methanol/water | 3.1 |
| 1:2 methanol/water | 4.6 |

6.1.1 Preparation of Azacytidine/Maleic Acid Cocrystal (Method A)

Figure 13A:
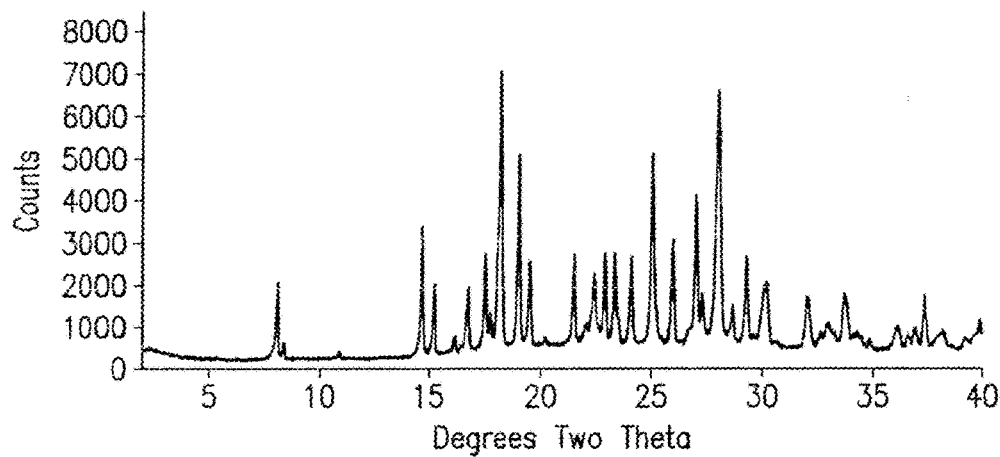

To 1.5 mL of a 1:3 (v:v) mixture of methanol and water was added maleic acid until solid persisted. The slurry was stirred at ambient temperature overnight and centrifuged. The liquid was decanted and treated with 84.1 mg (0.344 mmol) of azacytidine and 40.5 mg (0.349 mmol) of maleic acid. All of the solids dissolved, so additional azacytidine and maleic acid were added until solids of each persisted. The slurry was stirred at ambient temperature overnight and centrifuged. The liquid was decanted and treated with 81.8 mg (0.0.335 mmol) of azacytidine and 39.3 mg (0.339 mmol) of maleic acid. The slurry was stirred overnight at ambient temperature and centrifuged. The liquid was decanted and the solid was dried in a 60° C. oven to give afford the cocrystal. XRPD analysis shows that it was a mixture of the azacytidine/maleic acid cocrystal and uncomplexed maleic acid (FIG. 13A).

6.1.2 Preparation of 5-Azacytidine/Maleic Acid Cocrystal (Method B)

Figure 13B:
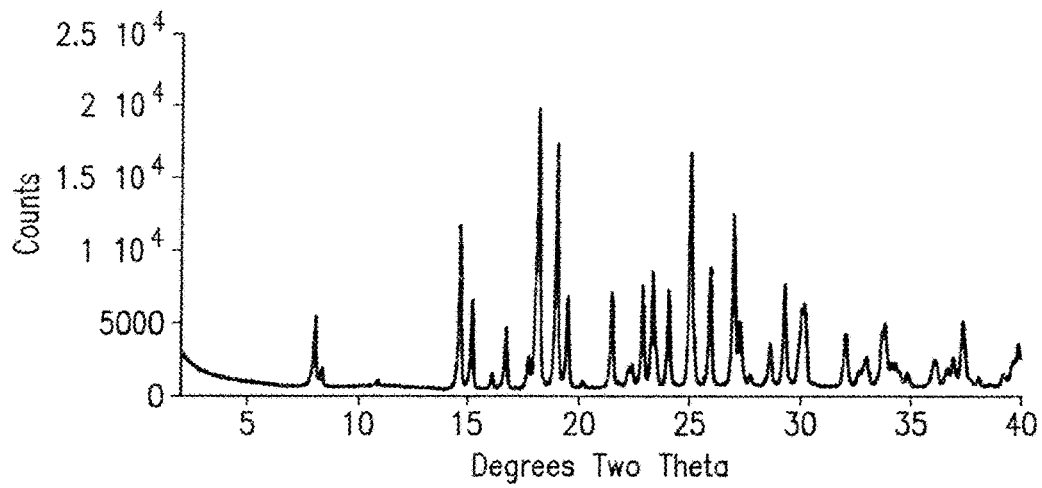
Figure 13C:
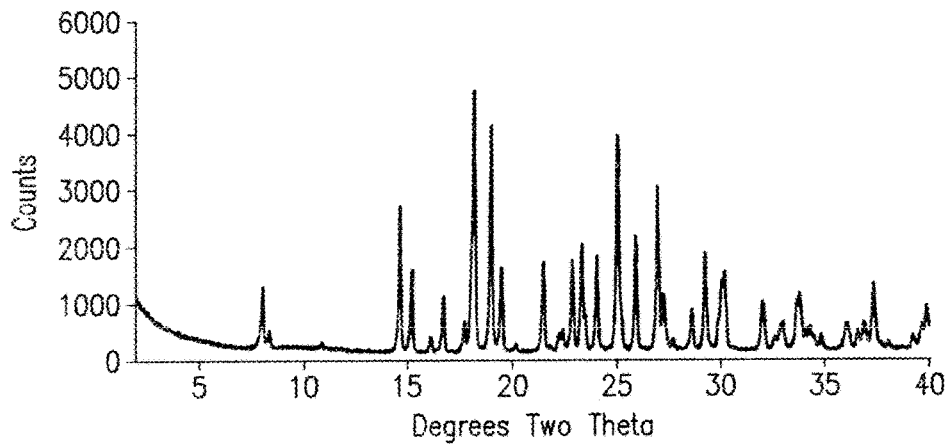
Figure 13D:
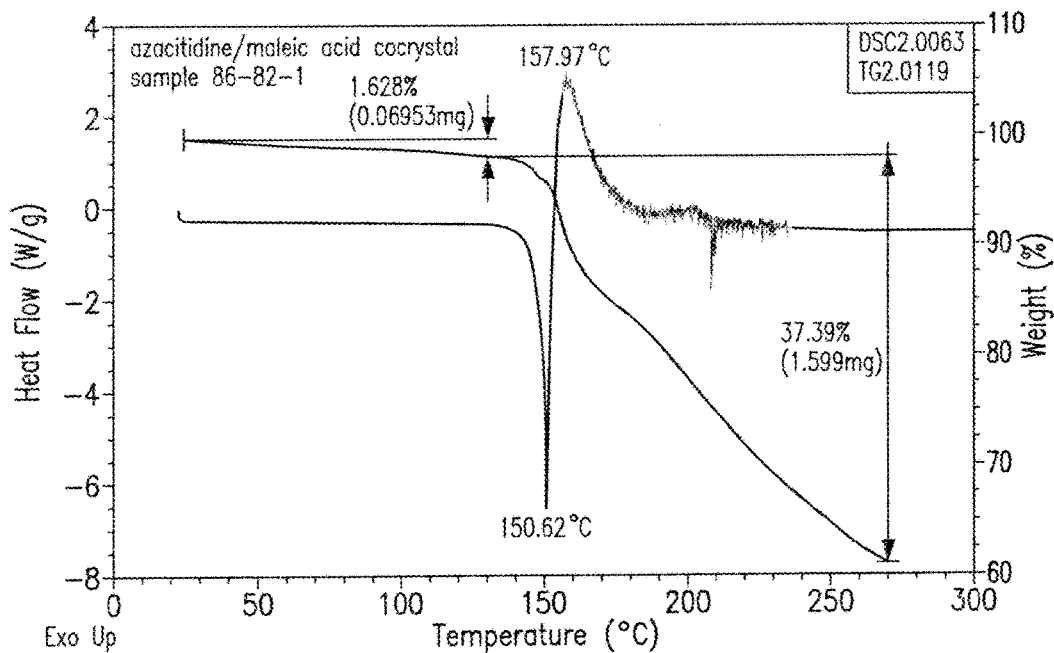
Figure 13E:
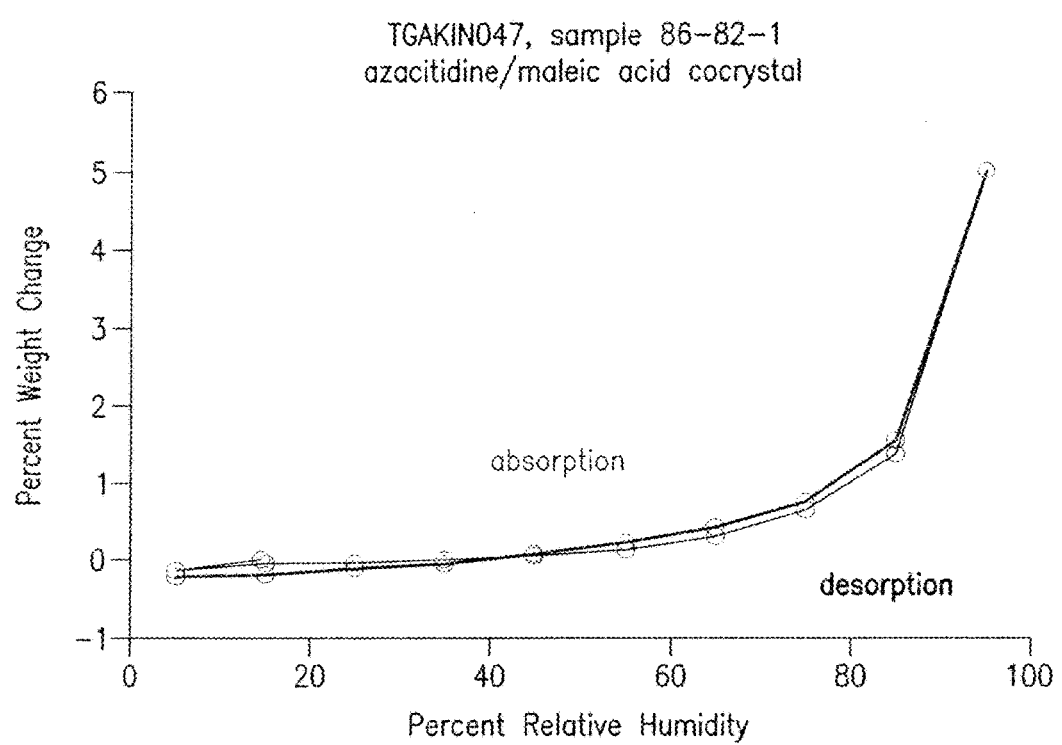

A mixture of 81.0 mg (0.332 mmol) of azacytidine, 38.9 mg (0.335 mmol) of maleic acid, 40 µL of a 1:2 (v:v) mixture of methanol and water, and one stainless steel grinding ball was placed in a polyether ether ketone (PEEK)

grinding cup. The cup was closed and agitated on a Retsch mill at 100% power for about 20 minutes. The grinding ball was removed and the contents of the cup were recovered to give 118.8 mg (99% yield) of pure azacytidine/maleic acid cocrystal. XRPD analysis of a pure sample of the azacytidine/maleic acid cocrystal is provided (FIG. 13B). DSC analysis shows endothermic event, likely melting, at about 151° C. and exothermic event at 158.0° C. TG analysis shows a 1.6% weight loss up to 130° C. and a 37.4% weight loss from 130-270° C., indicating that the cocrystal is essentially anhydrous (FIG. 13D). DVS analysis shows that the cocrystal is not very hygroscopic (FIG. 13E); furthermore, the crystalline form of the cocrystal did not change on exposure to elevated relative humidity, as evidenced by essentially identical XRPD patterns before and after DVS analysis (FIG. 13B-C). A $^1$H-NMR spectrum shown peaks from both azacitidine and maleic acid; integrations indicate the cocrystal contains a 1:1 molar ratio of those components.

6.1.3 Preparation of Azacytidine/Nicotinamide Cocrystal (Method B)

Figure 14A:
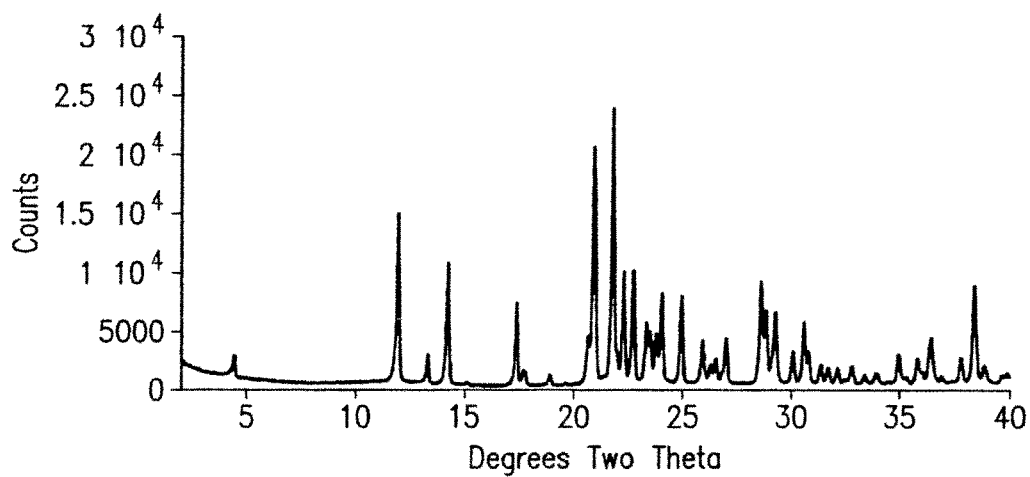
Figure 14B:
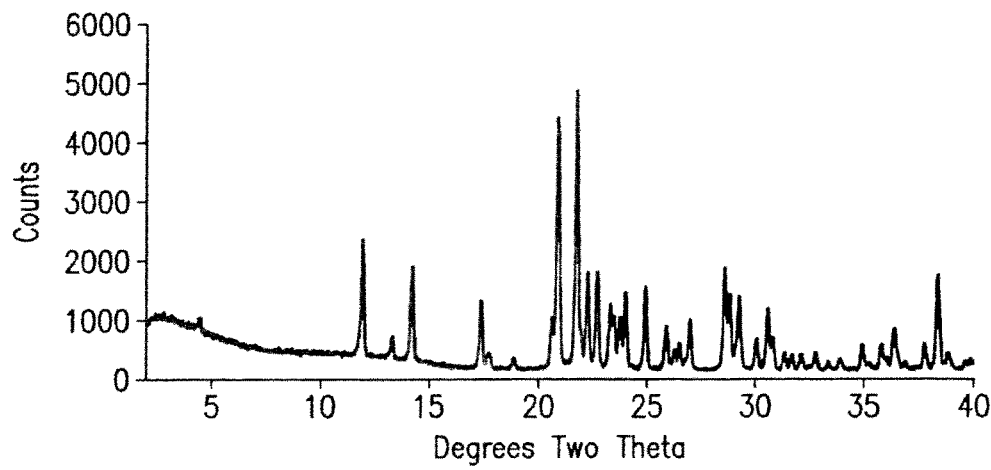
Figure 14C:
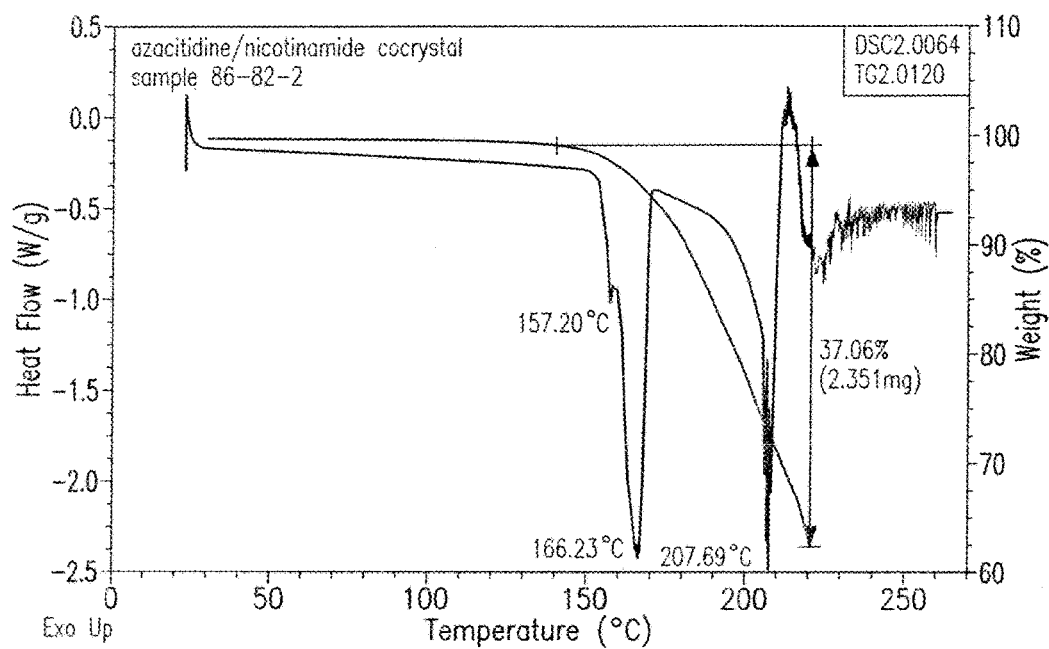
Figure 14D:
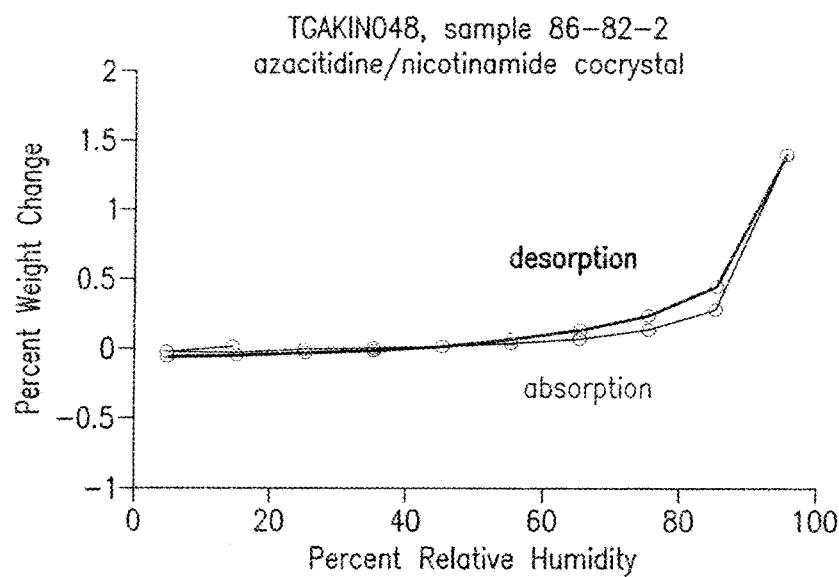

A mixture of 85.7 mg (0.351 mmol) of azacytidine, 42.4 mg (0.347 mmol) of nicotinamide, 40 µL of a 1:2 (v:v) mixture of methanol and water, and one stainless steel grinding ball was placed in a polyether ether ketone (PEEK) grinding cup. The cup was closed and agitated on a Retsch mill at 100% power for about 20 minutes. The grinding ball was removed and the contents of the cup were recovered to give 126.3 mg (99% yield) of pure azacytidine/nicotinamide cocrystal. XRPD analysis of a pure sample of the azacytidine/nicotinamide cocrystal is provided (FIG. 14A). DSC analysis shows endothermic event, likely melting, at about 166° C., other endothermic events at about 157° C. and 208° C. were also observed. The events at 157° C. and 166° C. may indicate a melt followed by a crystallization of another solid phase. TG analysis shows negligible weight loss up to 130° C. and a 37.1% weight loss from 140-220° C., indicating that the cocrystal is essentially anhydrous (FIG. 14C). DVS analysis shows that the cocrystal is not very hygroscopic (FIG. 14D); furthermore, the crystalline form of the cocrystal did not change on exposure to elevated relative humidity, as evidenced by essentially identical XRPD patterns before and after DVS analysis (FIG. 14A-B). A $^1$H-NMR spectrum shown peaks from both azacitidine and nicotinamide; integrations indicate the cocrystal contains a 1:1 molar ratio of those components.

6.1.4 Preparation of Azacytidine/Zinc Chloride Cocrystal (Method B)

Figure 15A:
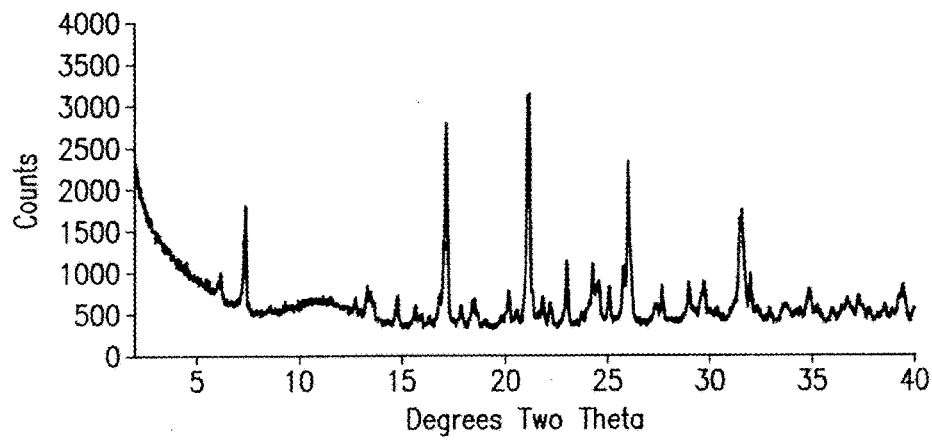
Figure 15B:
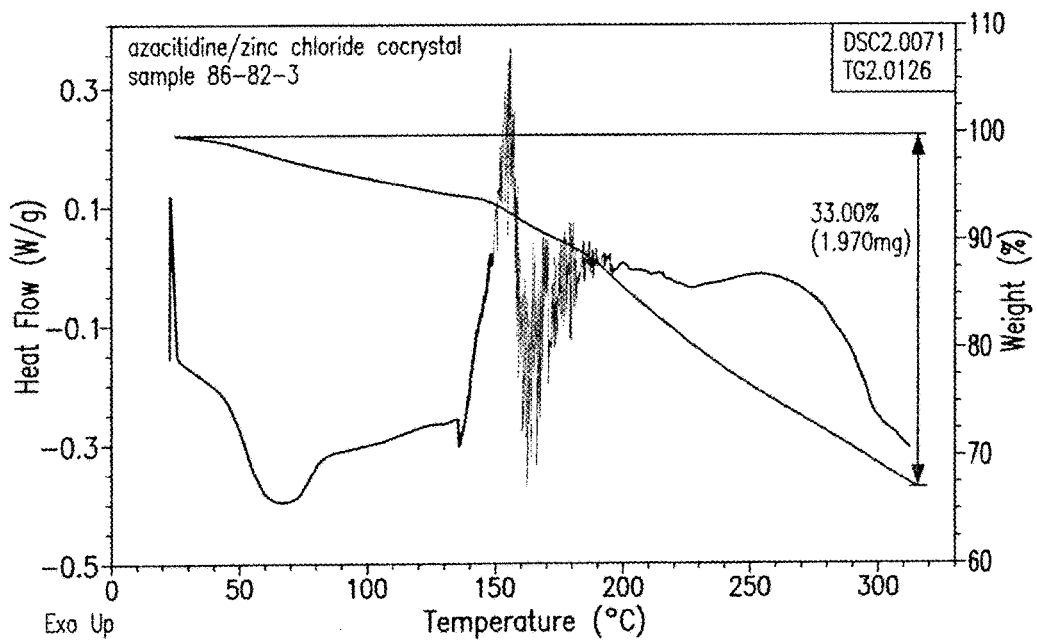
Figure 15C:
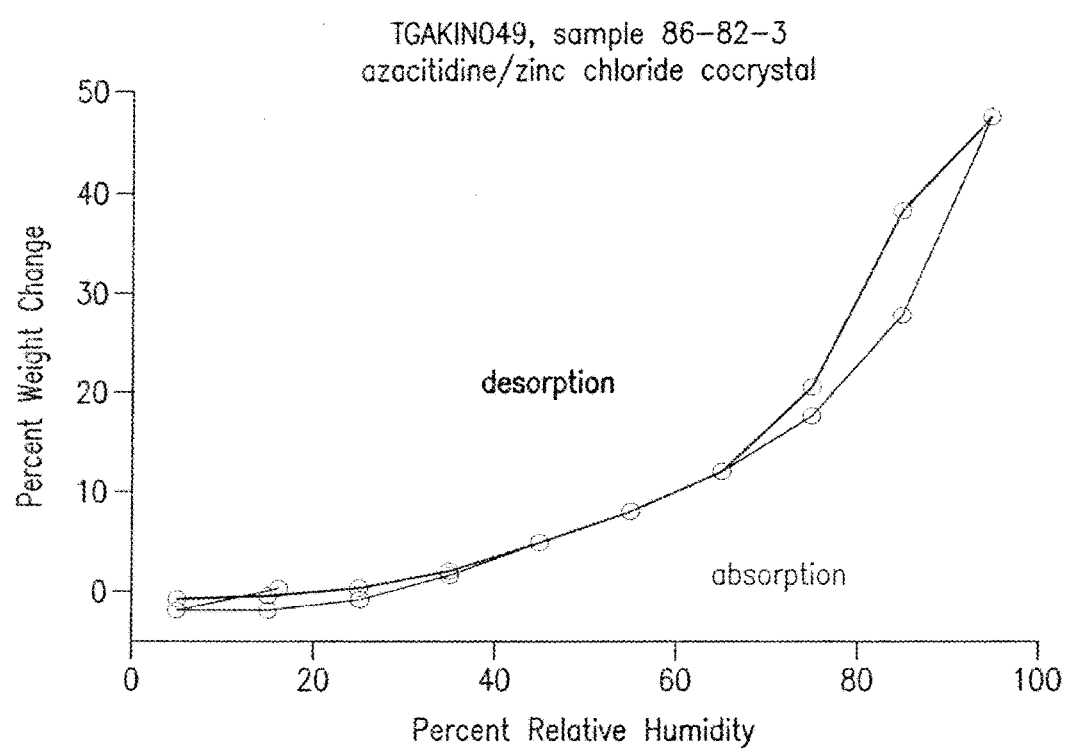
Figure 15D:
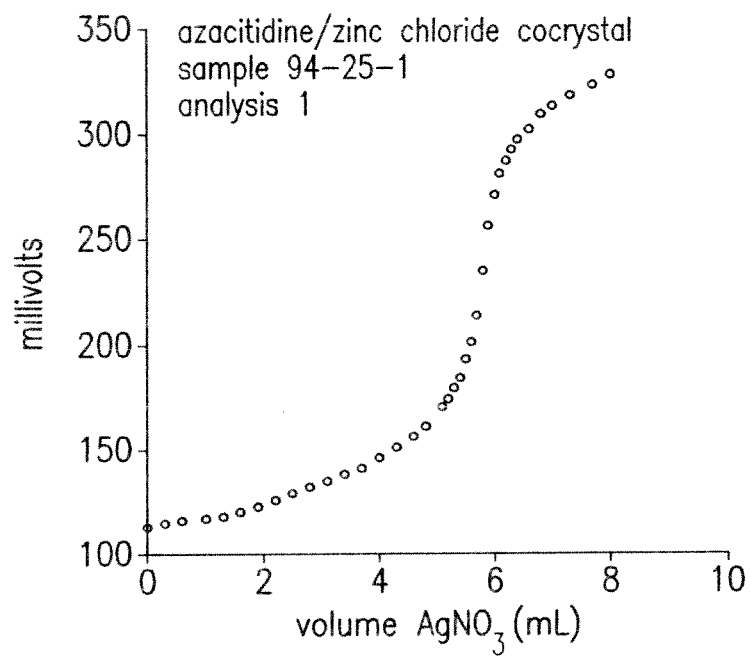
Figure 15D:
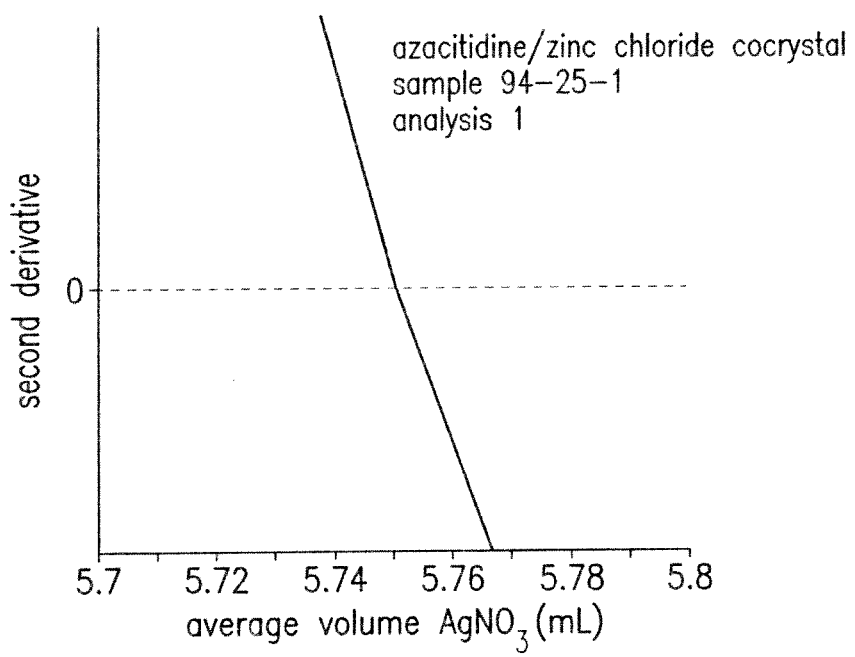
Figure 15D:
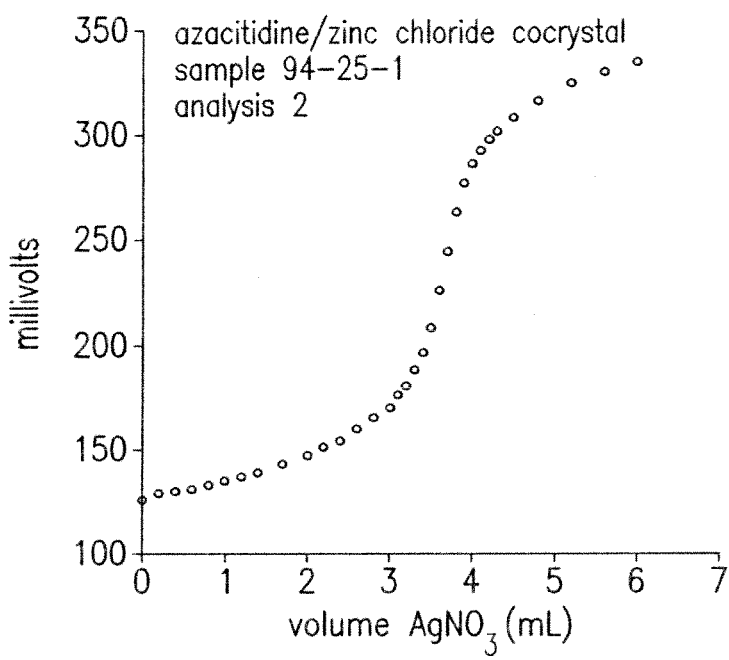
Figure 15D:
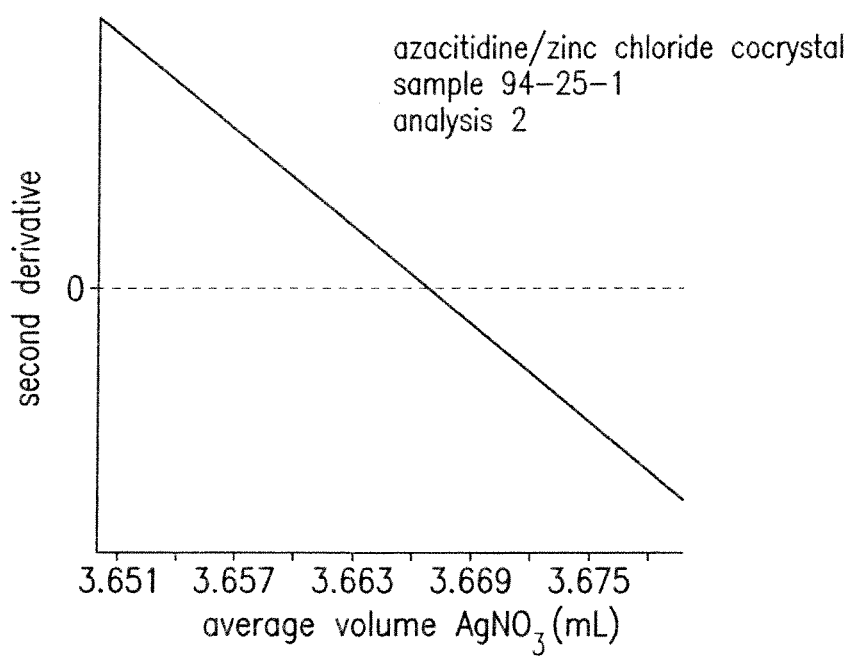

A mixture of 82.6 mg (0.338 mmol) of azacytidine, 46.6 mg (0.342 mmol) of zinc chloride, 40 µL of a 1:2 (v:v) mixture of methanol and water, and one stainless steel grinding ball was placed in a polyether ether ketone (PEEK) grinding cup. The cup was closed and agitated on a Retsch mill at 100% power for about 20 minutes. The grinding ball was removed and the contents of the cup were recovered to give 126.0 mg (98% yield) of the azacytidine/zinc chloride cocrystal. XRPD analysis of pure samples of the 5-azacytidine/zinc chloride cocrystal is provided (FIG. 15A-B).

It is difficult of ascertain the nature of the cocrystal obtained from the DSC and TG data obtained. DSC analysis shows a thermogram with no discrete event; a noisy appearance of the DSC thermogram around 150-200° C. suggests decomposition may be occurring. TG analysis shows constant weight loss from the start of the experiment, indicating that the cocrystal may be hydrated or solvated (FIG. 14C). DVS analysis shows that the cocrystal is very hygroscopic and likely deliquesces (FIG. 14D); the solid powder converted to a film during the experiment. The 5-azacytidine/zinc chloride cocrystals were further analyzed via ISE titrations. The results of duplicate analyses (16.6% and 16.9% chloride) are more consistent with the theoretical value for a 1:1 5-azacytidine:zinc chloride cocrystal (theoretical value 18.6%) than with either a 1:2 5-azacytidine:zinc chloride cocrystal (27.4%) or a 2:1 5-azacytidine:zinc chloride cocrystal (11.4%). The fact that the chloride content is lower than theoretical may be related to the volatile content of the sample suggested by TG analysis An NMR spectrum is consistent with the structure of azacitidine. Since zinc chloride is inactive in $^1$H NMR spectroscopy, the NMR data could not be used to infer cocrystal stoichiometry.

6.1.5 XRPD Overlay Data for Cocrystal Forms of 5-Azacytidine and a Coformer

Several of the solid forms had XRPD patterns that were suggestive of cocrystal formation. Those patterns contain peaks that do not appear to arise from any polymorph of 5-azacytidine or the relevant coformer. Plots containing those patterns are shown in FIGS. 16-23.

6.2 Assays 6.2.1 TNFα Inhibition Assay in PBMC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bioproducts, Woodland, Calif., USA), 2 mM L-glutamine, 100 U/ml penicillin, and 100 µg/ml streptomycin (Life Technologies).

PBMC ($2\times10^5$ cells) are plated in 96-well flat-bottom Costar tissue culture plates (Corning, N.Y., USA) in triplicate. Cells are stimulated with LPS (from Salmonella abortus equi, Sigma cat. no. L-1887, St. Louis, Mo., USA) at 1 ng/mL final in the absence or presence of compounds. Compounds provided herein are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% $CO_2$, and supernatants are then collected, diluted with culture medium and assayed for TNFα levels by ELISA (Endogen, Boston, Mass., USA). $IC_{50}$s are calculated using non-linear regression, sigmoidal dose-response, constraining the top to 100% and bottom to 0%, allowing variable slope (GraphPad Prism v3.02).

6.2.2 IL-2 and MIP-3α Production by T Cells

PBMC are depleted of adherent monocytes by placing $1\times10^8$ PBMC in 10 ml complete medium (RPMI 1640 supplemented with 10% heat-inactivated fetal bovine serum, 2 mM L-glutamine, 100 U/ml penicillin, and 100 µg/ml streptomycin) per 10 cm tissue culture dish, in 37° C., 5% $CO_2$ incubator for 30-60 minutes. The dish is rinsed with medium to remove all non-adherent PBMC. T cells are purified by negative selection using the following antibody (Pharmingen) and Dynabead (Dynal) mixture for every $1\times10^8$ non-adherent PBMC: 0.3 ml Sheep anti-mouse IgG beads, 15 µl anti-CD16, 15 µl anti-CD33, 15 µl anti-CD56, 0.23 ml anti-CD19 beads, 0.23 ml anti-HLA class II beads, and 56 µl anti-CD14 beads. The cells and bead/antibody mixture is rotated end-over-end for 30-60 minutes at 4° C. Purified T cells are removed from beads using a Dynal magnet. Typical yield is about 50% T cells, 87-95% $CD3^+$ by flow cytometry.

Tissue culture 96-well flat-bottom plates are coated with anti-CD3 antibody OKT3 at 5 µg/ml in PBS, 100 µl per well, incubated at 37° C. for 3-6 hours, then washed four times with complete medium 100 µl/well just before T cells are added. Compounds are diluted to 20 times of final in a round bottom tissue culture 96-well plate. Final concentrations are about 10 µM to about 0.00064 µM. A 10 mM stock of compounds provided herein is diluted 1:50 in complete for the first 20× dilution of 200 µM in 2% DMSO and serially diluted 1:5 into 2% DMSO. Compound is added at 10 µl per 200 µl culture, to give a final DMSO concentration of 0.1%. Cultures are incubated at 37° C., 5% $CO_2$ for 2-3 days, and supernatants analyzed for IL-2 and MIP-3α by ELISA (R&D Systems). IL-2 and MIP-3α levels are normalized to the amount produced in the presence of an amount of a compound provided herein, and $EC_{50}$s calculated using non-linear regression, sigmoidal dose-response, constraining the top to 100% and bottom to 0%, allowing variable slope (GraphPad Prism v3.02).

6.2.3 Cell Proliferation Assay

Cell lines Namalwa, MUTZ-5, and UT-7 are obtained from the Deutsche Sammlung von Mikroorganismen and Zellkulturen GmbH (Braunschweig, Germany). The cell line KG-1 is obtained from the American Type Culture Collection (Manassas, Va., USA). Cell proliferation as indicated by $^3$H-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 µM in a final concentration of about 0.25% DMSO in triplicate at 37° C. in a humidified incubator at 5% $CO_2$ for 72 hours. One microcurie of $^3$H-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 µl/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope. (GraphPad Prism v3.02).

6.2.4 Immunoprecipitation and Immunoblot

Namalwa cells are treated with DMSO or an amount of a compound provided herein for 1 hour, then stimulated with 10 U/ml of Epo (R&D Systems) for 30 minutes. Cell lysates are prepared and either immunoprecipitated with Epo receptor Ab or separated immediately by SDS-PAGE. Immunoblots are probed with Akt, phospo-Akt (Ser473 or Thr308), phospho-Gab1 (Y627), Gab1, IRS2, actin and IRF-1 Abs and analyzed on a Storm 860 Imager using ImageQuant software (Molecular Dynamics).

6.2.5 Cell Cycle Analysis

Cells are treated with DMSO or an amount of a compound provided herein overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

6.2.6 Apoptosis Analysis

Cells are treated with DMSO or an amount of a compound provided herein at various time points, then washed with annexin-V wash buffer (BD Biosciences). Cells are incubated with annexin-V binding protein and propidium iodide (BD Biosciences) for 10 minutes. Samples are analyzed using flow cytometry.

6.2.7 Luciferase Assay

Namalwa cells are transfected with 4 µg of AP 1-luciferase (Stratagene) per 1×10$^6$ cells and 3 µl Lipofectamine 2000 (Invitrogen) reagent according to manufacturer's instructions. Six hours post-transfection, cells are treated with DMSO or an amount of a compound provided herein. Luciferase activity is assayed using luciferase lysis buffer and substrate (Promega) and measured using a luminometer (Turner Designs).

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein in their entireties. Citation or identification of any reference in this application is not an admission that such reference is available as prior art. The full scope of the disclosure is better understood with reference to the appended claims.

What is claimed is:

1. A solid form comprising (a) 4-amino-1-β-D-ribofuranosyl-1,3,5-triazin-2(1H)-one, or a pharmaceutically acceptable salt, solvate, hydrate, stereoisomer, prodrug, or clathrate thereof; and (b) a conformer selected from the group consisting of glycine, propyl gallate, and nicotinamide.

2. The solid form of claim 1, wherein the molar ratio of 4-amino-1-β-D-ribofuranosyl-1,3,5-triazin-2(1H)-one to the coformer is from about 2:1 to 1:2.

3. The solid of claim 2, wherein the molar ratio of 4-amino-1-β-D-ribofuranosyl-1,3,5-triazin-2(1H)-one to the coformer is about 1:1.

4. The solid form of claim 1, which is crystalline.

5. The solid form of claim 1, which is a cocrystal.

6. The solid form of claim 1, which is greater than 80% by weight, greater than 90% by weight, greater than 95% by weight, greater than 97% by weight, or greater than 99% by weight a cocrystal.

7. The solid form of claim 1, which is physically pure.

8. The solid form of claim 1, which is free of other solid forms of 4-amino-1-β-D-ribofuranosyl-1,3,5-triazin-2(1H)-one.

9. The solid form of claim 1, which is free of solvent.

10. The solid form of claim 1, which is free of water.

11. The solid form of claim 1, further comprising amorphous 4-amino-1-β-D-ribofuranosyl-1,3,5-triazin-2(1H)-one.

12. The solid form of claim 1, which is stable.

13. The solid form of claim 1, which is crystalline and thermally stable.

14. A pharmaceutical composition comprising the solid form of claim 1.

15. The pharmaceutical composition of claim 14, further comprising a pharmaceutically acceptable excipient or carrier.

16. The pharmaceutical composition of claim 14, which is a single unit dosage form.

17. The pharmaceutical composition of claim 14, which is a tablet.

18. The pharmaceutical composition of claim 14, which is a capsule.

19. The pharmaceutical composition of claim 14, wherein the 5-azacytidine is in an amount of from about 0.1 to about 5 mg.

20. A method of treating a disease comprising administering the solid form of claim 1 or the pharmaceutical composition of claim 14 to a subject wherein the disease is selected from the group consisting of multiple myeloma, myeloproliferative disease, anemia, scleroderma, and amyloidosis.

21. The method of claim 20, further comprising administering a second active agent.

* * * * *

UNITED STATES PATENT AND TRADEMARK OFFICE
CERTIFICATE OF CORRECTION

PATENT NO. : 9,968,627 B2
APPLICATION NO. : 14/778553
DATED : May 15, 2018
INVENTOR(S) : G. Patrick Stahly et al.

Page 1 of 1

It is certified that error appears in the above-identified patent and that said Letters Patent is hereby corrected as shown below:

In the Claims

In Claim 1, at Column 66, Line 31, replace "conformer", with --- coformer ---

Signed and Sealed this
Thirty-first Day of July, 2018

Andrei Iancu
*Director of the United States Patent and Trademark Office*